(12) United States Patent
Lipp et al.

(10) Patent No.: US 8,992,983 B2
(45) Date of Patent: *Mar. 31, 2015

(54) RESPIRABLY DRY POWDER COMPRISING CALCIUM LACTATE, SODIUM CHLORIDE AND LEUCINE

(71) Applicant: Pulmatrix, Inc., Lexington, MA (US)

(72) Inventors: Michael M. Lipp, Framingham, MA (US); Jean C. Sung, Cambridge, MA (US)

(73) Assignee: Pulmatrix, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/284,880

(22) Filed: May 22, 2014

(65) Prior Publication Data

US 2015/0004233 A1 Jan. 1, 2015

Related U.S. Application Data

(63) Continuation of application No. 13/504,284, filed as application No. PCT/US2011/049333 on Aug. 26, 2011, now Pat. No. 8,758,824.

(60) Provisional application No. 61/378,146, filed on Aug. 30, 2010, provisional application No. 61/387,797, filed on Sep. 29, 2010, provisional application No. 61/431,205, filed on Jan. 10, 2011.

(51) Int. Cl.
| | |
|---|---|
| *A61K 33/14* | (2006.01) |
| *A61K 33/06* | (2006.01) |
| *A61K 31/198* | (2006.01) |

(Continued)

(52) U.S. Cl.
CPC ............... *A61K 33/14* (2013.01); *A61K 33/06* (2013.01); *A61K 31/198* (2013.01); *A61K 9/14* (2013.01); *A61K 9/0012* (2013.01); *A61K 45/06* (2013.01); *A61K 31/56* (2013.01); *A61K 31/138* (2013.01); *A61K 31/439* (2013.01);

(Continued)

(58) Field of Classification Search
None
See application file for complete search history.

(56) References Cited

U.S. PATENT DOCUMENTS

| | | | |
|---|---|---|---|
| 4,233,405 | A | 11/1980 | Neubeck |
| 4,637,815 | A | 1/1987 | Lemole |

(Continued)

FOREIGN PATENT DOCUMENTS

| | | |
|---|---|---|
| CN | 1240349 | 1/2000 |
| CN | 1446877 | 10/2003 |

(Continued)

OTHER PUBLICATIONS

Adi, et al., "Agglomerate strength and dispersion of pharmaceutical powders," Journal of Aerosol Science, 42:285-294, 2011.

(Continued)

*Primary Examiner* — Brian Gulledge
*Assistant Examiner* — Celeste A Roney
(74) *Attorney, Agent, or Firm* — McDermott Will & Emery LLP

(57) ABSTRACT

The present invention relates to respirable dry powders that contain respirable dry particles that comprise about 20%-37.5% (w/w) leucine, about 58.6-about 75% (w/w) calcium lactate, and about 3.9-about 5% (w/w) sodium chloride, and methods for treating a subject using the respirable dry powders.

19 Claims, 13 Drawing Sheets

(51) Int. Cl.
    *A61K 9/14* (2006.01)
    *A61K 9/00* (2006.01)
    *A61K 45/06* (2006.01)
    *A61K 31/56* (2006.01)
    *A61K 31/138* (2006.01)
    *A61K 31/5383* (2006.01)
    *A61K 31/137* (2006.01)
    *A61M 15/00* (2006.01)
    *A61K 31/439* (2006.01)

(52) U.S. Cl.
    CPC .......... *A61K 31/5383* (2013.01); *A61K 31/137* (2013.01); *A61M 15/00* (2013.01)
    USPC ........................................ 424/489; 424/680

(56) References Cited

U.S. PATENT DOCUMENTS

| | | | |
|---|---|---|---|
| 4,828,844 | A | 5/1989 | Rontgen-Odenthal et al. |
| 5,175,152 | A | 12/1992 | Singh |
| 5,230,884 | A | 7/1993 | Evans et al. |
| 5,466,680 | A | 11/1995 | Rudy |
| 5,571,535 | A | 11/1996 | Flowers et al. |
| 5,612,053 | A | 3/1997 | Baichwal et al. |
| 5,633,003 | A | 5/1997 | Cantor |
| 5,654,007 | A | 8/1997 | Johnson et al. |
| 5,709,202 | A | 1/1998 | Lloyd et al. |
| 5,785,049 | A | 7/1998 | Smith et al. |
| 5,817,028 | A | 10/1998 | Anderson |
| 5,898,037 | A | 4/1999 | Marx |
| 5,981,559 | A | 11/1999 | Nagaoka et al. |
| 5,985,309 | A | 11/1999 | Edwards et al. |
| 6,083,922 | A | 7/2000 | Montgomery |
| 6,165,463 | A | 12/2000 | Platz et al. |
| RE37,053 | E | 2/2001 | Hanes et al. |
| 6,214,536 | B1 | 4/2001 | Boucher |
| 6,254,854 | B1 | 7/2001 | Edwards et al. |
| 6,447,752 | B2 | 9/2002 | Edwards et al. |
| 6,451,352 | B1 | 9/2002 | Yvin et al. |
| 6,475,523 | B1 | 11/2002 | Staniforth |
| 5,582,728 | A1 | 6/2003 | Tayler et al. |
| 6,582,728 | B1 | 6/2003 | Platz et al. |
| 6,635,283 | B2 | 10/2003 | Edwards et al. |
| 6,669,959 | B1 | 12/2003 | Adjei et al. |
| 6,732,732 | B2 | 5/2004 | Edwards et al. |
| 6,749,835 | B1 | 6/2004 | Lipp et al. |
| 6,830,764 | B2 | 12/2004 | Inui et al. |
| 7,008,644 | B2 | 3/2006 | Batycky et al. |
| 7,112,572 | B2 | 9/2006 | Deadman et al. |
| 7,182,961 | B2 | 2/2007 | Batycky et al. |
| 7,192,919 | B2 | 3/2007 | Tzannis et al. |
| 7,306,787 | B2 | 12/2007 | Tarara et al. |
| 7,384,649 | B2 | 6/2008 | Batycky et al. |
| 7,556,798 | B2 | 7/2009 | Edwards et al. |
| 7,575,761 | B2 | 8/2009 | Bennett et al. |
| 7,838,532 | B2 | 11/2010 | Surber et al. |
| 7,879,358 | B2 | 2/2011 | Jackson et al. |
| 8,187,637 | B2 | 5/2012 | Edwards et al. |
| 2001/0008632 | A1 | 7/2001 | Freund et al. |
| 2001/0038858 | A1 | 11/2001 | Roser et al. |
| 2002/0177562 | A1 | 11/2002 | Weickert et al. |
| 2003/0129141 | A1 | 7/2003 | Platz et al. |
| 2003/0138403 | A1 | 7/2003 | Drustrup |
| 2003/0186894 | A1 | 10/2003 | Kuo et al. |
| 2004/0009128 | A1 | 1/2004 | Rabinowitz et al. |
| 2005/0004020 | A1 | 1/2005 | Yu et al. |
| 2005/0054682 | A1 | 3/2005 | Phillips |
| 2005/0211244 | A1 | 9/2005 | Nilsson et al. |
| 2005/0255049 | A1 | 11/2005 | Slowey et al. |
| 2005/0276845 | A1 | 12/2005 | Roser et al. |
| 2005/0281740 | A1 | 12/2005 | Gong et al. |
| 2006/0073173 | A1 | 4/2006 | Banach et al. |
| 2006/0142208 | A1 | 6/2006 | Boucher |
| 2006/0147520 | A1 | 7/2006 | Ruegg |
| 2007/0092535 | A1 | 4/2007 | Watts et al. |
| 2007/0202051 | A1 | 8/2007 | Schuschnig |
| 2007/0270502 | A1 | 11/2007 | Edwards et al. |
| 2007/0275091 | A1 | 11/2007 | King et al. |
| 2007/0292454 | A1 | 12/2007 | Bell et al. |
| 2008/0038207 | A1 | 2/2008 | Edwards et al. |
| 2008/0063722 | A1 | 3/2008 | Ward et al. |
| 2008/0152764 | A1 | 6/2008 | Kremer et al. |
| 2008/0190424 | A1 | 8/2008 | Lucking et al. |
| 2009/0208999 | A1 | 8/2009 | Groenendaal et al. |
| 2010/0159007 | A1 | 6/2010 | Staniforth |
| 2010/0285142 | A1 | 11/2010 | Staniforth et al. |
| 2004/0047810 | A1 | 3/2011 | Staniforth et al. |
| 2011/0192397 | A1 | 5/2011 | Saskar et al. |
| 2013/0004542 | A1 | 1/2013 | Martyn |

FOREIGN PATENT DOCUMENTS

| | | |
|---|---|---|
| CN | 101237853 | 3/2007 |
| CN | 101106975 | 1/2008 |
| EP | 0367723 | 5/1990 |
| EP | 0681833 | 11/1995 |
| EP | 1466610 | 10/2004 |
| JP | 05123398 | 5/1993 |
| JP | 2002510603 | 4/2002 |
| JP | 2002524579 | 4/2002 |
| JP | 2004/532217 | 10/2002 |
| JP | 2002543165 | 12/2002 |
| JP | 2005511628 | 5/2003 |
| JP | 2004-503482 | 2/2004 |
| JP | 2005531605 | 10/2005 |
| WO | 92/06695 | 4/1992 |
| WO | 96/12470 | 5/1996 |
| WO | 97/36574 | 10/1997 |
| WO | 97/44013 | 11/1997 |
| WO | 98/15205 | 4/1998 |
| WO | 99/51096 | 10/1999 |
| WO | 99/64014 | 12/1999 |
| WO | 00/13677 | 3/2000 |
| WO | 00/66206 | 11/2000 |
| WO | 01/13892 | 3/2001 |
| WO | 01/76610 | 10/2001 |
| WO | 01/85136 | 11/2001 |
| WO | 01/85137 | 11/2001 |
| WO | 01/95874 | 12/2001 |
| WO | 02/083079 | 10/2002 |
| WO | WO 03/043585 | 5/2003 |
| WO | 03/092654 | 11/2003 |
| WO | 03/103632 | 12/2003 |
| WO | 2004096204 | 11/2004 |
| WO | 2005/004852 | 1/2005 |
| WO | 2005004852 | 1/2005 |
| WO | 2005041921 | 5/2005 |
| WO | 2005041922 | 5/2005 |
| WO | 2005084638 | 9/2005 |
| WO | 2005092289 | 10/2005 |
| WO | 2005094869 | 10/2005 |
| WO | 2006029209 | 3/2006 |
| WO | 2006038070 | 4/2006 |
| WO | 2006084131 | 8/2006 |
| WO | 2006102438 | 9/2006 |
| WO | 2006125153 | 11/2006 |
| WO | 2008025560 | 3/2008 |
| WO | 2008065666 | 6/2008 |
| WO | 2009044141 | 4/2009 |
| WO | 2009130560 | 10/2009 |
| WO | 2010/111640 | 9/2010 |
| WO | 2010/111644 | 9/2010 |
| WO | 2010111640 | 9/2010 |
| WO | 2010111641 | 9/2010 |
| WO | 2010111644 | 9/2010 |
| WO | 2010111650 | 9/2010 |
| WO | 2010111680 | 9/2010 |
| WO | 2011006073 | 1/2011 |
| WO | 2011048379 | 4/2011 |
| WO | 2004/096204 | 11/2011 |

(56) References Cited

FOREIGN PATENT DOCUMENTS

| WO | 2012030647 | 3/2012 |
|---|---|---|
| WO | 2012030664 | 3/2012 |
| WO | 2012060645 | 3/2012 |

OTHER PUBLICATIONS

Adjei and Garren, "Pulmonary delivery of peptide drugs: effect of partical size on bioavailability of leuprolide acetate in healthy male volunteers", J.Pharm. Res., 7:565-569 (1990).
Aldrich Catalog pp. 1502 1998-1999.
Anderson, et al., "Effect of cystic fibrosis on inhaled aerosol boluses" Am. Rev. Respir. Dis. 40: 1317-1324 (1989).
Bergeron, et al., "Controlling droplet deposition with polymer additives" Nature. 405:772-775 (2000).
Boren, "The development of a molecular model of lung" Arch Intern Med 126(3):491-495 (1970).
Broadhead, et al., The Spray Drying of Pharmaceuticals, Drug Development and Industrial Pharmacy, 18 (11&12):1169-1206, 1992.
Chiou, et al, "A novel production method for inhalable cyclosporine A powders by confined liquid impinging jet precipitation," Journal of Aerosol Science, 39:500-509, 2008.
Bucca, C. and G. Rolla, "Nebulised magnesium in asthma: the right solution for an old remedy?" The Lancet, 361:2095-2096 (2003).
Burg, et al., "Cellular Response to Hyperosmotic Stresses," Am. Physiological Soc., 87:1441-1474 (2007).
Cataldo, et al. "Induced sputum: comparison between isotonic and hypertonic saline solution inhalation in patients with asthma" Chest, 120(6):1815-21 (2001).
Chan, H., "Spray Dried Powders and Powder Blends of Recombinant Human Deoxyribonuclease (rhDNase) for Aerosol Delivery," Pharmaceutical Research, 14(4): 431-437; 1997.
Choi, et al., "Inhalation delivery of proteins from ethanol suspensions" Proc. Natl. Acad, Sci. 98:11103-11107 (2001).
Clarke, et al., "Resistance to two-phase-gas-liquid flow in airways" J. Appl. Physiol.29(4):464-471 (1970).
Copp, et al., "Hypertonic Shock Inhibits Growth Factor Receptor Signaling, Induces Caspase-3 Activation, and Causes Reversible Fragmentation of the Mitocholdrial Network," Am. J. Physiol, 288. C403-C415 (2005).
Costello, B., et al., "Use of the Du Nouy Ring with a Rotational Rheometer to Measure Interfacial Rheology Properties", Annual Transactions of the Nordic Rheology Society. 2006, 14.
Crowder, et al., "2001: An Odyssey in Inhaler Formulation and Design," Pharmaceutical Technology, 99-113, Jul. 2001.
Davis, et al., "Charged Polymers Modulate Retrovirus Transduction via Membrane Charge Neutralization and Virus Aggregation", Biophys J,86:1234-1242 (2004).
Dawson, et al., "Enhanced viscoelasticity of human cystic fibrotic sputum correlates with increasing microheterogeneity in particle transport", J. of Biol. Chem., 278(50):50393-50401 (2003).
Denn, M.M., "Viscoelasticity", In Process Fluid Mechanics, Prentice-Hall, Englewood Cliffs, New Jersey, pp. 358-373 (1980).
Edvvards et al., "Inhaling to mitigate exhaled bioaerosols," PNAS (2004), vol. 101, pp. 17383-17388.
Edwards, "The macrotransport of aerosol particles in the lung: aerosol deposition phenomena" J. Aerosol Sci., 26:293-317 (1995).
Edwards, et al., "Novel Inhalents for Control and Protection Against Airborne Infections," Respiratory Drug Delivery, 2006, pp. 41-48.
Eng Pa, et al., "Short-term efficacy of ultrasonically nebulized hypertonic saline in cystic fibrosis," Pediatr. Pulmonol., 21:77-83 (1996).
Hawley's Condensed Chemical Dictionary. 14th edition John Wiley & Sons, 2001, pp. 161 and 977.
Im. et al., "In vivo determination of surface tension in the horse trachea and in vitro model studies", Respir. Physiol., 109:81-93 (1997).
Evrensel, et al., "Viscous airflow through a rigid tube with compliant lining. A simple model for the air-mucus interaction in pulmonary pathways", J.Biomech. Eng., 115:262-267 (1993).

Hsu, et al., "Role of Viscoelasticity in Tube Model of Airway Reopening. I. Nonnewtonian Sols.". J. Appl Physiol. 76 (6):2481-2489 (1994).
Ferguson, et al., "Transmission intensity and impact of control policies on the foot and mouth epidemic in Great Britain", Nature, 414(6861):329 (2001).
Fiegel et al., "Airborne Infectious Disease and the Suppression of Pulmonary Bioaerolsols," DDT, Jan. 2006, 11 (1/2), pp. 51-57.
Finlay, The Mechanics of Inhaled Pharmaceutical Aerosols, Academic Press, 143-149 (2001).
French, et al., "The influence of formulation on emission, deaggregation and deposition of dry powders for inhalation", J. Aerosol Sci., 27:769-783 (1996).
Friedmen, et al. "A Randomized, Prospective, Double-Blind Study on the Efficacy of Dead Sea Salt Nasal Irrigations," The Laryngoscope, 2006, pp. 878-882, 116.
Fuge, et al., "The geochemistry of iodine—a review", Environmental Geochemistry and Health, 8(2):31-54 (1986).
Gad-El-Hak, et al., "On the interaction of compliant coatings with boundary layer flows", J. Fluid Mech., 140:257-280 (1984).
Ganderton, "The generation of respirable clouds from coarse powder aggregates", Biopharmaceutical Sciences,3:101-105 (1992).
Geller, et al., "Development of a DPI Tobramycin Formulation using Pulmosphere Technology," J. of Aerosol Medicine and Pulmonary Drug Delivery, 24:175-182, 2011.
Goldberg, et al., "Mechanism of enhancement of microbial cell hydrophobicity by cationic polymers", J. Bacteriology, 172:5650-5654 (1990).
Gonda, "Aerosols for delivery of therapeutic and diagnostic agents to the respiratory tract", Critical Reviews in Therapeutic Drug Carrier Systems, 6:273-313 (1990).
Ghoroi, et al., "Dispersion of fine and ulirafine powders through surface modification and rapid expression." Chem Eng Sci., 85:11-24, 2013.
Hirschman, et al., "Inhibition of human immunodeficiency virus type 1 replication by nonionic block polymer surfactants" J. Med. Virol. 42(3):249-54 (1994).
Guo-Zhong Tao, et al., "Hyposmotic Stress Induces Cell Growth Arrest Via Proteasome Activation and Cyclin/Cyclin-Dependent Kinase Degradation," J. Biological Chemistry, 277(22): 19295-19303 (2002).
Heyder J., et al., "Deposition of particles in the human respiratory tract in the size range 0,005-15µm" J. Aerosol Sci., 17:811-825 (1986).
Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).
Intl Search Report, dated Dec. 1, 2011, from corres. PCT Application No. PCT/US2011/049333.
Otrisal Dosierspray Losung in Novaris Consumer health, Germany.
Riedler, J., et al. "Inhaled hypertonic saline increases sputum expectoration in cystic fibrosis," J. Pediatr Child Health, 32:48-50 (1996).
Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).
Rabbani, et al., "The Influence of formulation components on the aerosolisation properties of spray dried powders," J. of Controlled Release, 110:130-140, 2005.
Piret, et al., "Sodium lauryl sulfate, a microbicide effective against enveloped and nonenveloped viruses" Curr. Drug Targets. 3(1):17-30 (2002).
Perry's Chemical Engineers' Handbook, 7th ed., 1997, pp. 2-10, 2-11, 2-120, 2-121.
Paul, Fundamental Immunology, Raven Press, New York, pp. 699-716, 1984.
Patton and Platz, "Pulmonary delivery of peptides and proteins for systemic action", Adv. Drug Del. Rev., 8:179-196 (1992).
Papineni and Rosenthal, "The size distribution of droplets in the exhaled breath of healthy human subjects", J. Aerosol Med., 10(2): 105-116 (1997).

(56) References Cited

OTHER PUBLICATIONS

Jaffari, et al., "Rapid characterisation of the inherent dispersibility of respirable powders using dry dispersion laser diffraction," International Journal of Pharmaceuticals, 447:124-131, 2013.
Kaye, et al., "Simultaneously Manufactured Nano-In-Micro(SIMANIM) Particles for Dry-Powder Modified-ReleaseDelivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured pre-operative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal linin liquid increases upper airway patency in anaesthetised rabbits", J. Physiol. 547(Pt 2):603-11(2003).
Kulkarni, et al., "Formulation and Characterization of Nasal Sprays," Inhalation Magazine, 6(3):10-15 (2012).
Kurashima, et al., "A pilot study of surfactant inhalation for the treatment of asthmatic attack" Jpn J Aerogol 40 (2):160-3 (1991).
Oneda, et al., "The Effect of Formulation Variables on the Dissolution and Physical Properties of Spray-Dried Microspheres Containing Organic Salts," Powder Technology, 30:377-384, 2003.
Nannini, L.J., et al., "Magnesium Sulfate as a Vehicle for Nebulized Salbutamol in Acute Asthma", Am. J. Med., 108:193-197 (2000).
Morrison, F.A., "Introduction, How Much Do I Need to Learn about Rheology?" In Understanding Rheology. Oxford University Press, New York, pp. 1-11 (2001).
Modler, "Calcium as an Adjuvant for Spray-Drying Acid Whey," Journal of Dairy Science, 61:294-299, 1978.
Macosko, C.W., "Linear Viscoelasticity", in Rheology. Principles, Measurements, and Applications, Wiley-VCH, New York, pp. 109-133 (1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-267.
Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced bu Divalent Cations," Biorheology. 1979, pp. 331-337, vol. 16.
The Merck Index 12th edition, Merck &Co., Inc., Whitehouse Station, NJ, p. 1089. 1996, pp. 177 & 1614-1615.
Merck Manual Home Edition. "Asthma: Lung and Airway Disorders" accessed at www.merck.com/mmhe/print/sec04/ch044a/html accessed on May 5, 2010.
Merck Manual Home Edition "Chronic Obstructive Pulmonary Disease," accessed at www.merck.com/mmhe/print/sec04/ch045a/html accessed on Mar. 21, 2010.
Merck Manual Home Edition, "Acute Respiratory Distress Syndrome (ARDS)," accessed on Nov. 17, 2011 at www.merckmanuals.com/home/lung_and_airway_disorders/respiratory_filure_and_acute_respiratory_distress_syndrome/acute_respiratory_distress_syndrome_ards.html#v727948.
The Online Merck Manual Medical Second Home Edition article, entitled; "Influenza"—accessed on Feb. 22, 2010 at www.merck.com/mmhe/print/sec17/ch198/ch198d.html.
Miller, M.J., "Assessing the use of Pharmacokinetic Models in Risk Assessments on Inhaled Toxicants", School of Public Health Sciences, Environmental Health, and Toxicology (1992).
Robinson, M. et al., "Effect of hypertonic saline amiloride, and cough on mucociliary clearance in patients with cystic fibrosis," Am J. Respir. Crit. Care Med., 153:1503-1509 (1996).
Robinson, M., et al., "Effect of increasing doses of hypertonic saline on mucociliary clearance in patients with cystic fibrosis," Thorax, 52:900-903 (1997).
Robinson, M., et al., The effect of inhaled mannitol on bronchial mucus clearance in cystic fibrosis patients: a pilot study, Eur. Respir. J., 14:678-685 (1999).
Wright, et al., "Inhaled Cationic Salt Dry Powder Formulation PUR 118 Inhibits Rhinovirus-induced Inflammation and Exacerbation in a Mouse Model of Acute Allergic Asthma," ERS 2011 Meeting, Poster (Sep. 24, 2011).
Rosenblum, E. E. ("fish." Grolier Multimedia Encyclopedia, 2006, Grolier Online, accessed Nov. 21, 2006 (gme.grolier.com/cgi-bin/article?assetid=0106750-0).
Rote Liste Service, "Rote Liste 2002" (2002), Editor Cantor Verlag, Frankfurt/Main, XP002416908, par. [72087], par. [28005].
Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).
Sanders, et al., "Cystic fibrosis sputum: a barrier to the transport of nanospheres", Am J Respir Crit Care Med., 162:1905-1911 (2000).
Sarrell, et al., "Nebulized 3% Hypertonic Saline Solution Treatment in Ambulatory Children with Viral Bronchiolitis Decreases Symptoms," Chest, 2002, 122, pp. 2015-2020.
Schelling G., et al., Biophyiscal Journal, 66:134-140 (1994).
Schurch, et al., "Surfactant displaces particles toward the epithelium airways and alveoli", Respir Physiol., 80:17-32 (1990).
Serrano, P., et al., "New Data on Pharmacological Properties and Indications of Magnesium," In New Perspectives in Magnesium Research. Springher-Verglag, London, pp. 127-139 (2007).
Seville, et al., "Spray-Dried Powders for Pulmonary Drug Delivery," Crit. Rev. in Therapeutic Drug Carrier Systems, 24(4), 307-360, 2007.
Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.
Shur, et al., Cospray-Dried Unfractionated Heparin with L-Leucine as a Dry Powder Inhaler Mucolytic for Cystic Fibrosis Therapy, J. Pharmaceutical Sciences, 97:4857-4868, 2008.
Wright, et al., "Inhaled Calcium Based Dry Powder Inhibits Rhinovirus-induced Inflammation and Exacerbation in a Mouse Model of Allergic Airway Inflammation," ERS 2011 Meeting, Abstract (Sep. 24, 2011).
Suara, et al., "Effect of Zinc Salts on Respiratory Syncytial Virus Replication," Antimicrobial Agents and Chemotherapy, Mar. 2004, pp. 783-790, vol. 48 (3).
Tabata and Ikada, "Macrophage phagocytosis of biodegradable microspheres composed of L-lactic acid/glycolic acid homo- and copolymers", J. Biomed. Mater. Res., 22:837-858 (1988).
Takebayashi, et al., "Role of tachykinins in airway responses to ozone in rats" J Appl Physiol 85:442-450 (1998).
Tansey, "The challenges in the development of metered dose inhalation aerosols using ozone-friendly propellants" Spray Technol. Market. 4:26-29 (1994).
Tibby, et al., "Exogenous surfactant supplementation in infants with respiratory syncytial virus bronciolitis" Am J Respir Crit Care Med., 162(4 Pt 1):1251 (2000).
Timsina, et al., Drug Delivery to the respiratory tract using dry powder inhalers Int. J. Pharm., 101:1-13 (1995).
Tsurumi et al., "Effect of high salt treatment on influenza B viral protein synthesis in MDCK cells," Microbiology and immunology, 1983, 27(6), pp. 519-529 (Full document).
Tuberkuleza, Problemy 58(1): 40-41 (1980).
Ulcerative Colitis: Inflammatory bowel Disease (n.d.) retrieved from http://adam.about.com/reports/000069_1.htm.
Vehring, "Pharmaceutical Particle Engineering via Spray Drying" Pharma. Res., vol. 25, No. 5, May 2008.

(56) References Cited

OTHER PUBLICATIONS

Arold, et al., "A Novel Inhaled Dry Powder Delivery Platform; Efficacy of Fluticasone and Salmeterol during Allergic Asthma," ISAM 2011 Meeting, Poster (Apr. 6, 2011).
Vinnikov, et al., "Aerosol Inhalations of Calcium Chloride in Combination Therapy of Pulmonary Tuberculosis," Kazanskii Meditsinskii Zhurnal (1962), vol. 4, pp. 7-9 (translation included).
Visser, "Van der Waals and other cohesive forces affecting powder fluidization", Powder Technology, 58:1-10 (1989).
Vollenbroich, et al., "Mechanism of inactivation of enveloped viruses by the biosurfactin from *Bacillus subtilis*" Biologicals, 25(3):289-97 (1997).
Wade, C.E., "Hypertonic saline resuscitation in sepsis," Critical Care. Oct. 2002; 6(5), 397-398.
Wark, Rab, McDonald V. "Nebulized hypertonic saline for cystic fibrosis" (Cochrane Review). In: The Cochrane Library. Oxford, UK: Update Software, 2005.
Watanabe, et al., "Immunogenicity and protective efficacy of replication-incompetent influenza virus-like particles" Journal of Virology 76(2):767-773 (2002).
Arold, et al., "Efficacy of Fluticasone and Salmeterol in a Novel Dry Powder Delivery Platform," ATS 2011 Meeting, Abstract #C22 (May 15, 2011).
Hava, et al., "Inhaled Cationic Salts Inhibit Infection of Multiple Viral Pathogens and Prevent Influenza Infection In Vivo," ATS 2011 Meeting, Abstract #C60 (May 16, 2011).
Williams, "Portal to the interior: viral pathogenesis and natural compounds that restore mucosal immunity and modulate inflammation", Alternative Medicine Review. 8(4):395-409 (2003).
Hava, et al., "Inhaled Calcium Salts Reduce Acute Airway Inflammation Associated with Tobacco Smoke Exposure," ATS 2011 Meeting, Abstract #713 (May 16, 2011).
Zanen and Lamm, "The optimal particle size for parasymathicolytic aerosols in mild asthmatics", J. Int. J. Pharm., 114:111-115 (1995).
Hava, et al., "Inhaled Cationic Airway Lining Modulator (iCALM) Therapy, a Novel Aerosol Treatment for Respiratory Infections Reduces Clinical Symptoms and Transmission of Influenza A Infection," ATS 2010 Meeting, Abstract #A6846 (May 14, 2010).
Sung, et al., "iSPERSE™: Formulation and In Vitro Characterization of a Novel Dry Powder Drug Delivery Technology," RDD Europe 2011 Meeting, Abstract, (May 3, 2011).
Edwards. et al., "Novel Inhalants for Control and Protection Against Airborne Infections," RDD 2006 Meeting, Abstract, (Apr. 23, 2006).
Kenyon, et al,. "Late-breaking Abstract: Inhaled Calcium Salts Reduce Tobacco Smoke Induced Airway Inflammation and Improve Lung Pathology." ERS 2011 Meeting, Abstract (Sep. 24, 2011).
DeHaan, et al., "Inhaled Calcium Based Dry Powder Enhances Whole Lung Mucociliary Clearance in Sheep," ATS 2011 Meeting, Abstract (May 15, 2011).
Sung, "A Novel Platform for DP Inhalation Drugs," 2011 Manufacturing Chemist J article Nov. 7, 2011, accessed online on Jan. 11, 2013.
Wright, et al., "Cationic Salt Dry Powders Inhibit Inflammatory Responses in a Rhinovirus-induced Exacerbation Mouse Model of Allergic Airway Inflammation," ATS 2012 Meeting, Abstract (May 18, 2012).
Wright, et al., "Inhaled Calcium Salts Reduce Expression of Inflammatory Mediators Associated with Tobacco Smoke Exposure to Reduce Airway Inflammation." ERS 2012 Meeting, Poster (Sep. 1, 2012).
Arold, et al., "iSPERSE: A Novel Inhaled Dry Powder Delivery Platform for the Delivery of Large Molecule Drugs to the Lung for Local and Systemic Treatments," ATS 2012 Meeting, Abstract (May 18, 2012).
DeHaan, et al., "Inhaled calcium Based Dry Powder Enhances Whole Lung Mucociliary Clearance in Sheep," ATS 2012 Meeting, Abstract (May 18, 2012).
Nair, et al., "Inhaled Cationic Airway Lining Modulator (iCALM) attenuates allergen-induced eosinophilic bronchitis," ATS 2012 Meeting, Abstract (May 18, 2012).
Hava, et al., "Reduced Neutrophilic Airway Inflamation by Inhalation of Dry Powder Calcium Salts in a Mouse Model of Sub-Chronic Tobacco Smoke Exposure," ATS 2012 Meeting, Abstract (May 18, 2012).

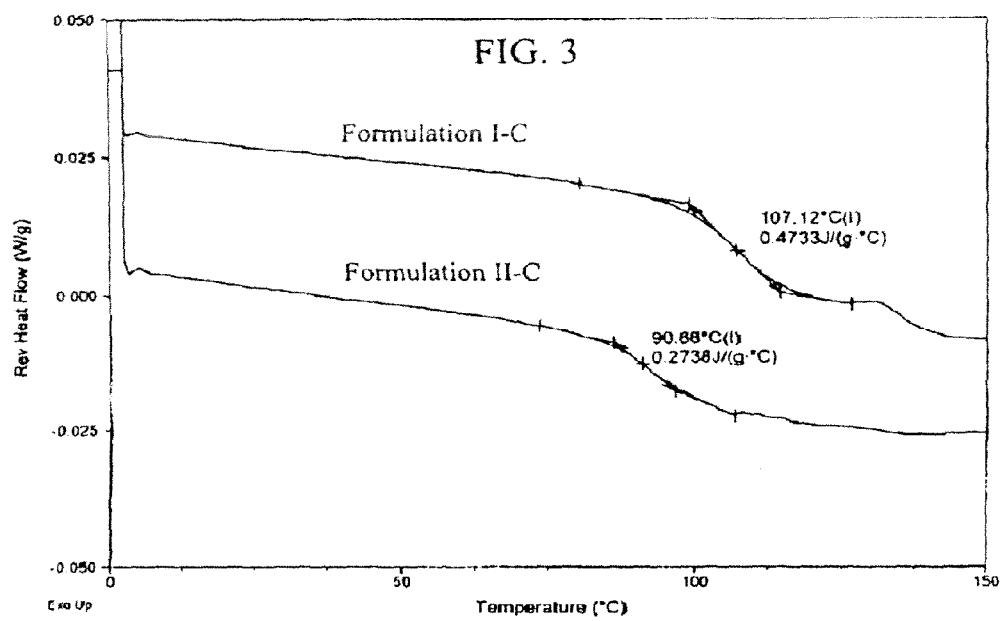
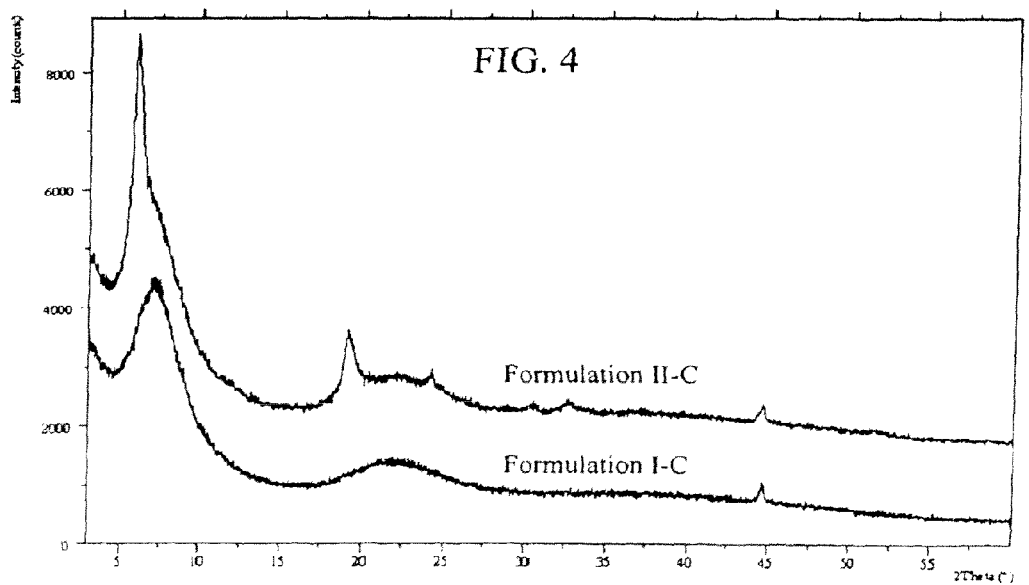

Ratio selection – Ferret influenza

RESPIRABLY DRY POWDER COMPRISING CALCIUM LACTATE, SODIUM CHLORIDE AND LEUCINE

RELATED APPLICATIONS

This application is a continuation of U.S. patent application Ser. No. 13/504,284, filed Apr. 26, 2012, which is the U.S. National Stage of International Application No. PCT/US2011/049333, filed Aug. 26, 2011, published in English, and claims the benefit of U.S. Patent Application No. 61/431,205, filed on Jan. 10, 2011, the benefit of U.S. Patent Application No. 61/387,797 filed on Sep. 29, 2010, and the benefit of U.S. Patent Application No. 61/378,146 filed on Aug. 30, 2010, the entire teachings of these applications are incorporated herein by reference.

BACKGROUND OF THE INVENTION

Pulmonary delivery of therapeutic agents can offer several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent. MDIs are reliable for drug delivery primarily to the upper and middle airways but are limited because they typically deliver only low doses per actuation. However, it is the bronchioles and alveoli that are often the site of manifestation of pulmonary diseases such as asthma and infections.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include (i) relatively large primary liquid aerosol droplet size often requiring impaction of the primary droplet onto a baffle to generate secondary splash droplets of respirable sizes, (ii) lack of liquid aerosol droplet size uniformity, (iii) significant recirculation of the bulk drug solution, and (iv) low densities of small respirable liquid aerosol droplets in the inhaled air.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved. However the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. No. 6,131,570; U.S. Pat. No. 5,724,957; and U.S. Pat. No. 6,098,620. Disadvantages of this approach include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 6,9216527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability, which considerably diminish dispersibility and the efficiency of dry powder-based inhalation therapies. For example, interparticular Van der Waals interactions and capillary condensation effects are known to contribute to aggregation of dry particles. See Hickey, A. et al., "Factors Influencing the Dispersion of Dry Powders as Aerosols", Pharmaceutical Technology, August, 1994. Maintaining the physicochemical properties of dry powder with the passage of time and long-term storage has been a challenge.

To overcome interparticle adhesive forces, Batycky et al. in U.S. Pat. No. 7,182,961 teach production of so called "aerodynamically light respirable particles," which have a volume median geometric diameter (VMGD) of greater than 5 microns (μm) as measured using a laser diffraction instrument such as a HELOS/RODOS system (manufactured by Sympatec, Princeton, N.J.). See Batycky et al., column 7, lines 42-65. Another approach to improve the dispersibility of respirable particles of average particle size of less than 10 μm, involves the addition of a water soluble polypeptide or other suitable excipients (including amino acid excipients such as leucine) in an amount of 50% to 99.9% by weight of the total composition. See Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols so produced typically include substantial quantities of inert carriers, solvents, emulsifiers, propellants, and other non-drug material. In general, the large quantities of non-drug material are required for effective formation of respirable dry particles small enough for alveolar delivery (e.g. less than 5 microns and preferably less than 3 microns). However, these amounts of non-drug material also serve to reduce the purity and amount of active drug substance that can be delivered. Thus, these methods remain substantially incapable of introducing large active drug dosages accurately to a patient for systemic delivery.

Therefore, there remains a need for the formation of small particle size aerosols that are highly dispersible. There is a need for dry powders that are dense in mass and in drug, in order to maximize the quanity of drug within a given delivery container. In addition, methods that produce aerosols comprising greater quantities of drug and lesser quantities of non-drug material are needed. There is also a need for dry powders that exhibit stable physicochemical properties over the passage of time. Finally, a method that allows a patient to administer a unit dosage rapidly with one or two, small volume breaths is needed.

SUMMARY OF THE INVENTION

The invention relates to respirable dry powders comprised of dry particles that contain calcium lactate, sodium chloride and leucine. The respirable dry powders comprise respirable dry particles that contain about 20% (w/w) to about 37.5% (w/w) leucine, about 58.6% (w/w) to about 75% (w/w) calcium lactate, and about 3.9% (w/w) to about 5% (w/w) sodium chloride. An exemplary dry powder can contain dry particles that comprise i) about 20% (w/w) leucine, ii) about 75% (w/w) calcium lactate, and iii) about 5% (w/w) sodium chloride. Another exemplary dry powder can contain dry particles that comprise i) about 37.5% (w/w) leucine, ii) about 58.6% (w/w) calcium lactate, and iii) about 3.9% (w/w) sodium chloride. The composition of the formulations disclosed herein are presented on a dry (anhydrous) basis, unless otherwise noted.

The invention also relates to respirable dry powders that comprise respirable dry particles that contain calcium lactate, sodium chloride, one or more additional therapeutic agent and optionally leucine, wherein the dry particles comprises on a dry basis:
A. about 60% to about 75% (w/w) calcium lactate, about 2% to about 5% (w/w) sodium chloride, about 15% to about 20% (w/w) leucine, and up to about 20% (w/w) of one or more additional therapeutic agents;
B. about 45.0% to about 58.6% (w/w) calcium lactate, about 1.9% to about 3.9% (w/w) sodium chloride, about 27.5% to about 37.5% (w/w) leucine, and up to about 20% (w/w) of one or more additional therapeutic agent;
C. about 75% (w/w) calcium lactate, about 5% (w/w) sodium chloride, about 0.01% to about 20% (w/w) of one or more additional therapeutic agents, and about 20% (w/w) or less leucine; or
D. about 58.6% (w/w) calcium lactate, about 3.9% (w/w) sodium chloride, about 0.01% to about 37.5% (w/w) of one or more additional therapeutic agents, and about 37.5% (w/w) or less leucine.

The respirable dry particles have a volume median geometric diameter (VMGD) of 5 microns or less as measured at the one bar dispersion setting on the HELOS/RODOS laser diffraction system. The respirable dry particles have a VMGD of less than 5 microns, such as between 1 and 3 microns, as measured at the one bar dispersion setting on the HELOS/RODOS laser diffraction system.

The respirable dry powders have a Hausner Ratio of at least 1.5, preferably at least 2.0. In some embodiments, the dry powders have a Hausner Ratio of at least 1.4. The respirable dry powders have a dispersibility ratio at 1 bar/4 bar of less than 1.5, such as between 1.0 and 1.2, as measured at the 1 bar and 4 bar dispersion settings on the HELOS/RODOS laser diffraction system. The respirable dry powders have a dispersibility ratio at 0.5 bar/4 bar of less than 1.5, such as between 1.0 and 1.3, as measured by laser diffraction (HELOS/RODOS system).

The respirable dry powders have a Fine Particle Fraction (FPF) of less than 3.4 microns of at least 20% or at least 30%. The respirable dry powders have a Fine Particle Fraction (FPF) of less than 5.6 microns of at least 30%, or at least 40%, or at least 50%.

The respirable dry powders are characterized by a high emitted dose. For example, a Capsule Emitted Powder Mass (CEPM) of at least about 80% of said respirable dry powder contained in a unit dose container that contains 50 mg of said dry powder, in a dry powder inhaler is achieved when a total inhalation energy of less than about 1 Joule is applied to said dry powder inhaler. Alternatively, a CEPM of at least about 80% of said respirable dry powder contained in a unit dose container that contains 40 mg of said dry powder, in a dry powder inhaler is achieved when a total inhalation energy of less than about 1 Joule is applied to said dry powder inhaler.

The respirable dry powders can contain amorphous and/or crystalline states. For example, calcium lactate can be amorphous and the sodium chloride and/or leucine can be crystalline, or calcium lactate and leucine can be amorphous. Alternatively, the calcium lactate and sodium chloride are substantially in the amorphous phase and the leucine is in either the crystalline and/or amorphous phase.

The respirable dry powders can further comprise an additional therapeutic agent.

The invention also relates to a method for treating a respiratory disease comprising administering to the respiratory tract of a patient in need thereof an effective amount of a respirable dry powder as described herein.

The invention also relates to a method for treating or preventing an acute exacerbation of a respiratory disease comprising administering to the respiratory tract of a patient in need thereof an effective amount of a respirable dry powder as described herein.

The invention also relates to a method for treating or preventing an infectious disease of the respiratory tract comprising administering to the respiratory tract of a patient in need thereof an effective amount of a respirable dry powder as described herein.

The invention also relates to a method for reducing inflammation comprising administering to the respiratory tract of a patient in need thereof an effective amount of a respirable dry powder as described herein.

The invention also relates to a dry powder as described herein for use in therapy of a disease as described herein.

BRIEF DESCRIPTION OF THE DRAWINGS

FIG. 3 shows reversible trace mDSC data for Formulations I-C and II-C. The $T_g$ of Formulation I-C was determined to be approximately 107° C. and Formulation II-C approximately 91° C.

FIG. 4 shows high resolution XRPD diffractograms of Formulations I-C and II-C. Peaks at approximately 6, 19, 24, 31 and 33° characteristic of leucine (not shown) can be seen in the diffractogram for Formulation II-C, indicating the presence of crystalline leucine in this powder (the peak at approximately 44° in each scan is due to the sample holder). There are no crystallinity peaks observed in the diffractograms for either Formulations I-C and II-C that are characteristic of either calcium lactate pentahydrate or sodium chloride.

DETAILED DESCRIPTION OF THE INVENTION

Figure 1:
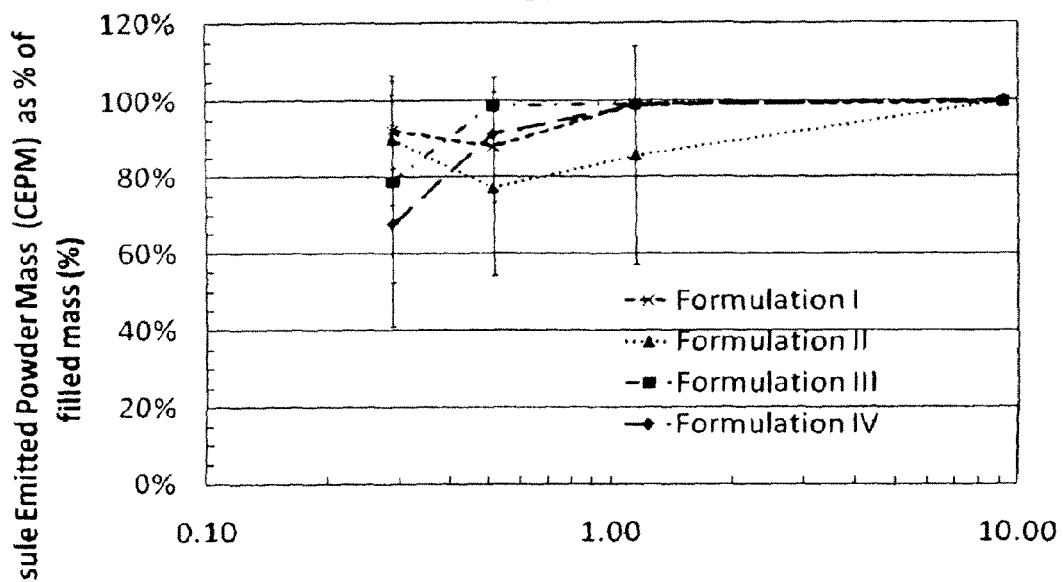
FIG. 1 is a graph showing mass emitted from a capsule for Formulations I, II, III, and IV at a capsule fill weight of 50 mg using a high resistance dry powder inhaler. All formulations had complete emission at 10 Joules. All formulation had greater than 80% emission at 1 Joule. All formulations had greater than 75% emission at 0.5 Joules. Inhaled energy was calculated from the inhaled flow rate (Q), volume (V) and inhaler resistance (R) using the formula Energy=R2Q2V.

This invention relates to respirable dry powders containing respirable dry particles that comprise about 20% (w/w) leucine, about 75% (w/w) calcium lactate and about 5% (w/w) sodium chloride. This invention also relates to respirable dry powders containing respirable dry particles that comprise about 37.5% (w/w) leucine, about 58.6% (w/w) calcium lactate, and about 3.9% (w/w) sodium chloride. The invention further relates to methods for treating a subject using the respirable dry powders, and to the respirable dry powders for use in treating a subject with a condition described herein.

Calcium lactate possesses sufficient aqueous solubility to allow for its processing into respirable dry powders via spray-drying and to facilitate dissolution upon deposition in the lungs, yet possesses a low enough hygroscopicity to allow for the production of dry powders with high calcium salt loads that are relatively physically stable upon exposure to normal and elevated humidity. Calcium lactate also has a significantly lower heat of solution than other calcium salts such as calcium chloride, which is beneficial for administration to the respiratory tract, and lactate ions are safe and acceptable for inclusion in pharmaceutical compositions.

The respirable dry particles may be large or small, e.g., the dry powders can have a geometric diameter (VMGD) between 0.5 microns and 30 microns. In preferred aspects, the respirable dry particles are small and dispersible. Preferably, the VMGD and/or mass median aerodynamic diameter (MMAD) of the dry powder or dry particles is between 0.5 and 10 microns, more preferably between 1 and 5 microns.

Respirable dry powders that contain small particles that are dispersible in air, and preferably dense (e.g., dense in active ingredient) are a departure from the conventional wisdom. It is well known that the propensity for particles to aggregate or agglomerate increases as particle size decreases, which reduces or eliminates dispersibility. See, e.g., Hickey, A. et al., "Factors Influencing the Dispersion of Dry Powders as Aerosols", Pharmaceutical Technology, August, 1994.

As described herein, the invention provides respirable dry powders that contain respirable particles that are small and dispersible in air without additional energy sources beyond the subject's inhalation. Thus, the respirable dry powders and respirable dry particles can be used therapeutically, without including large amounts of non-active components (e.g., excipients, carrier particles) in the particles or powders, or by using devices that apply mechanical forces to disrupt aggregated or agglomerated particles during or just prior to administration. Rather, the invention provides respirable dry powders that contain respirable particles which are dispersible even with a passive dry powder inhaler.

The respirable dry powders and respirable particles of the invention are also, generally, dense in active ingredient(s), i.e., calcium cations (e.g., in the form of calcium lactate). For example, as described herein, when an excipient is included in the respirable dry powder or particles, the excipient is a minor component of less than 40% by weight. Accordingly, a smaller amount of powder will need to be administered in order to deliver the desired dose of calcium in comparision to other types of powders. For example, the desired dose of calcium may be delivered with one or two inhalations from a capsule-type or blister-type inhaler.

DEFINITIONS

As used herein, the terms "administration" or "administering" of respirable dry particles refers to introducing respirable dry particles to the respiratory tract of a subject.

The term "capsule emitted powder mass" or "CEPM" as used herein, refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "dispersible" is a term of art that describes the characteristic of a dry powder or dry particles to be dispelled into a respirable aerosol. Dispersibility of a dry powder or dry particles is expressed herein as the quotient of the VMGD measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "1 bar/4 bar," and "0.5 bar/4 bar," respectively, and dispersibility correlates with a low quotient. For example, 1 bar/4 bar refers to the VMGD of respirable dry particles or powders emitted from the orifice of a RODOS dry powder disperser (or equivalent technique) at about 1 bar, as measured by a HELOS or other laser diffraction system, divided by the VMGD of the same respirable dry particles or powders measured at 4 bar by HELOS/RODOS. Thus, a highly dispersible dry powder or dry particles will have a 1 bar/4 bar or 0.5 bar/4 bar ratio that is close to 1.0. Highly dispersible powders have a low tendency to agglomerate, aggregate or clump together and/or, if agglomerated, aggregated or clumped together, are easily dispersed or deagglomerated as they emit from an inhaler and are breathed in by a subject. Dispersibility can also be assessed by measuring the size emitted from an inhaler as a function of flowrate. As the flow rate through the inhaler decreases, the amount of energy in the airflow available to be transferred to the powder to disperse it decreases. A highly dispersible powder will have its size distribution as characterized aerodynamically by its mass median aerodynamic diameter (MMAD) or geometrically by its VMGD, not substantially increase over a range of flow rates typical of inhalation by humans, such as about 15 to 60 LPM.

The term "dry particles" as used herein refers to respirable particles that may contain up to about 25%, up to about 20%, or up to about 15% water or other solvent, or be substantially free of water or other solvent, or be anhydrous.

The term "dry powder" as used herein refers to a composition that contains finely dispersed respirable dry particles that are capable of being dispersed in an inhalation device and subsequently inhaled by a subject. Such a dry powder or dry particle may contain up to about 25%, up to about 20%, or up to about 15% water or other solvent, or be substantially free of water or other solvent, or be anhydrous.

The term "effective amount," as used herein, refers to the amount of agent needed to achieve the desired effect, such as an amount that is sufficient to increase surface and/or bulk viscoelastic of the respiratory tract mucus (e.g., airway lining fluid), increase gelation of the respiratory tract mucus (e.g., at the surface and/or bulk gelation), increase surface tension of the respiratory tract mucus, increase elasticity of the respiratory tract mucus (e.g., surface elasticity and/or bulk elasticity), increase surface viscosity of the respiratory tract mucus (e.g., surface viscosity and/or bulk viscosity), reduce the amount of exhaled particles, reduce pathogen (e.g., bacteria, virus) uptake or pathogen burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second FEV1 and/or forced expiratory volume in 1 second FEV1 as a proportion of forced vital capacity FEV1/FVC) or stimulate innate immunity of airway epithelium. The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopia convention, Rockville, Md., 13$^{th}$ Revision, 222-225, 2007. This method utilizes an in vitro device set up to mimic patient dosing.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage two and on the final collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACI. The eight-stage ACI cutoffs are different at the standard 60 L/min flowrate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPD(<4.4)", 'FPD<4.4 µm", FPD(<4.4 microns)" and "fine particle dose of less than 4.4 microns" as used herein, refer to the mass of respirable dry powder particles that have an aerodynamic diameter of less than 4.4 micrometers. For example, FPD<4.4 µm can be determined by using an eight-stage ACI at the standard 60 L/min flowrate and summing the mass deposited on the final collection filter, and stages 6, 5, 4, 3, and 2 for a single dose of powder actuated into the ACI.

The terms "FPF (<5.0)", "FPF<5 µm", "FPF (<5.0 microns)," and "fine particle fraction of less than 5.0 microns" as used herein, refer to the fraction of a mass of respirable dry particles that have an aerodynamic diameter of less than 5.0 micrometers. For example, FPF (<5.0) can be determined by using an eight-stage ACI at the standard 60 L/min flow rate by extrapolating from the eight-stage complete data set. This parameter may also be identified as "FPF_TD(<5.0)," where TD means total dose. When used in conjunction with a geometric size distribution such as those given by a Malvern Spraytec, Malvern Mastersizer or Sympatec Helos particle sizer, "FPF (<5.0)" refers to the fraction of a mass of respirable dry particles that have a geometric diameter of less than 5.0 micrometers.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the final collection filter of a two-stage collapsed ACI by the total mass of respirable dry particles weighed into a capsule for delivery to the instrument. This parameter may also be identified as "FPF_TD (<3.4)," where TD means total dose. A similar measurement can be conducted using an eight-stage ACI. The eight-stage ACI result can also be calculated by the USP method of using the dose collected in the ACI instead of what was in the capsule to determine FPF.

"Hausner ratio" is a term of art that referrs to the tap density divided by the bulk density and typically correlates with bulk powder flowability (i.e., an increase in the Hausner ratio typically corresponds to a decrease in powder flowability.)

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

As used herein, the term "respiratory tract" includes the upper respiratory tract (e.g., nasal passages, nasal cavity, throat, pharynx), respiratory airways (e.g., larynx, tranchea, bronchi, bronchioles) and lungs (e.g., respiratory bronchioles, alveolar ducts, alveolar sacs, alveoli).

The term "small" as used herein to describe respirable dry particles refers to particles that have a volume median geometric diameter (VMGD) of about 10 microns or less, preferably about 5 microns or less.

Dry Powders and Dry Particles

The invention relates to respirable dry powders and respirable dry particles that contain calcium as an active ingredient. The calcium is generally present in the dry powders and dry particles in the form of calcium lactate. In particular, the respirable dry powders comprise respirable dry particles that contain about 20% (w/w) to about 37.5% (w/w) leucine, about 58.6% (w/w) to about 75% (w/w) calcium lactate, and about 3.9% (w/w) to about 5% (w/w) sodium chloride. The weight percentages are on a dry basis and the ratio of $Ca^{2+}$ to $Na^+$ in the particles is about 4:1 (mole:mole). For example, the invention provides respirable dry powders referred to as Formulation I and Formulation II.

Formulation I contains respirable dry particles that contain i) about 20% (w/w) leucine, ii) about 75% (w/w) calcium lactate, and iii) about 5% (w/w) sodium chloride.

Formulation II contains respirable dry particles that contain i) about 37.5% (w/w) leucine, ii) about 58.6% (w/w) calcium lactate, and iii) about 3.9% (w/w) sodium chloride. The weight percentages are on a dry basis.

In Formulations I and II, the dry particles are preferably small and dispersible. These dry particles are also calcium dense. The dry particles contain a high concentration of calcium salt (i.e., about 40% or more (w/w)) and are thus considered calcium salt dense. Preferably, the dry particles of the invention have a VMGD, when measured at a dispersion (i.e., regulator) pressure setting of 1 bar, of about 5 microns or less, as measured by laser diffraction using a Spraytec system (particle size analysis instrument, Malvern Instruments) or using a HELOS/RODOS system (laser diffraction sensor with dry dispensing unit, Sympatec GmbH).

Preferably, the respirable dry particles of Formulations I and II have a VMGD as measured by laser diffraction at the dispersion pressure setting of 1.0 bar using a HELOS/RODOS system of about 5 microns or less (e.g., about 0.1 µm to about 5 µm), about 4 µm or less (e.g., about 0.1 µm to about 4 µm), about 3 µm or less (e.g., about 0.1 µm to about 3 µm), about 1 µm to about 5 µm, about 1 µm to about 4 µm, about 1.5 µm to about 3.5 µm, about 2 µm to about 5 µm, about 2 µm to about 4 µm, or about 2 µm to about 3 µm.

If desired, the respirable dry particles of Formulations I and II can be large and dispersible, and preferably calcium dense. For example, the respirable dry particles can have a VMGD as measured by HELOS/RODOS at the dispersion pressure setting of 1.0 bar of up to about 30 µm.

Surprisingly, respirable dry powders of Formulation I and Formulation II have poor flow properties, yet, are highly dispersible. This is surprising because flow properties and dispersibility are both known to be negatively effected by particle agglomeration or aggregation. Thus, it is unexpected that particles that have poor flow characteristics would be highly dispersible.

In particular, the respirable dry powders of Formulation I and Formulation II have a Hausner Ratio that is greater than 1.5, and can be 1.6 or higher, 1.7 or higher, 1.8 or higher, 1.9 or higher, 2 or higher, 2.1 or higher, 2.2 or higher, 2.3 or higher, 2.4 or higher, 2.5 or higher, 2.6 or higher or 2.7 or higher, between 2.2 and 2.9, between 2.2 and 2.8, between 2.2 and 2.7, between 2.2 and 2.6, between 2.2 and 2.5, between 2.3 and 2.5, between 2.6 and 2.8, about 2.7, or about 2.4. In some preferred embodiments, the respirable dry powders of Formulation I and Formulation II have a Hausner Ratio that is 1.4 or higher.

In addition to any of the features and properties described herein, in any combination, the respirable dry powders and respirable dry particles can have a heat of solution that is not highly exothermic. Preferably, the heat of solution is determined using the ionic liquid of a simulated lung fluid (e.g. as described in Moss, O.R. 1979. Simulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol Physiol. 281, L807-L815) at pH 7.4 and 37° C. in an isothermal calorimeter. For example, the respirable dry powders or respirable dry particles can have a heat of solution that is less exothermic than the heat of solution of calcium chloride dihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol, about −10 kcal/mol to about 10 kcal/mol, about −8 kcal/mol to about 8 kcal/mol, or about −6 kcal/mol to about 6 kcal/mol. In a preferred aspect of the invention, the heat of solution is between about −7 kcal/mol to about 7 kcal/mol, between about −6 kcal/mol to about 6 kcal/mol, or between about −5 kcal/mol to about 5 kcal/mol.

The respirable dry particles of Formulations I and II are dispersible, and have 1 bar/4 bar and/or 0.5 bar/4 bar ratio of about 1.5 or less (e.g., about 1.0 to about 1.5). Preferably, the dry particles of Formulations I and II have 1 bar/4 bar and/or 0.5 bar/4 bar of about 1.0 to about 1.2, and/or about 1.0 to about 1.1.

The respirable dry particles of Formulations I and II have an MMAD of about 10 microns or less, such as an MMAD of about 0.5 micron to about 10 microns. Preferably, the dry particles of the invention have an MMAD of about 7 microns or less (e.g., about 0.5 micron to about 7 microns), preferably about 1 micron to about 7 microns, or about 2 microns to about 7 microns, or about 3 microns to about 7 microns, or about 4 microns to about 7 microns, about 5 microns to about 7 microns, about 1 micron to about 6 microns, about 1 micron to about 5 microns, about 2 microns to about 5 microns, about 2 microns to about 4 microns, or about 3 microns.

The Formulation I and Formulation II respirable dry powders have an FPF of less than about 5.6 microns (FPF<5.6 μm) of the total dose of at least about 38%, preferably at least about 40%, or between about 40% and about 50%, at least 50%, or between about 50% and about 60%, or at least 60%.

The Formulation I and Formulation II respirable dry powders have a FPF of less than about 3.4 microns (FPF<3.4 μm) of the total dose of at least about 20%, preferably at least about 25%, or between about 20% and about 30%, or at least 30%, or between about 30% and about 40%, or at least 40%.

The Formulation I and Formulation II respirable dry powders and dry particles preferably have a tap density of about 0.5 g/cm$^3$ to about 1.2 g/cm$^3$. For example, the small and dispersible dry particles of Formulation I and Formulation II can have a tap density of about 0.6 g/cm$^3$ to about 1.0 g/cm$^3$, about 0.7 g/cm$^3$ to about 1.0 g/cm$^3$, or about 0.8 g/cm$^3$ to about 1.0 g/cm$^3$. If desired, powders and particles that have a tap density that is less than about 0.4 g/cc can be prepared.

The respirable dry powders and dry particles of Formulation I and Formulation II can have a water or solvent content of less than about 25%, less than about 20%, or less than about 15% by weight of the respirable dry powder or particle. For example, the respirable dry particles of the invention can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the invention can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5%, or about 5%.

The respirable dry powders and dry particles of Formulation I and Formulation II contain a high percentage of calcium in the composition, and are calcium dense. The respirable dry particles contain at least 10% calcium by weight of the dry powder (wt calcium/wt dry powder), at least 11% calcium by weight of the dry powder, at least 12% calcium by weight of the dry powder; at least 13% calcium by weight of the dry powder, at least 14% calcium by weight of the dry powder, between 10% and 12% calcium by weight of the dry powder, between 12% and 14% calcium by weight of the dry powder, about 11% or about 13% calcium by weight of the dry powder. Additionally, the respirable dry powder and dry particles of Formulation I and Formulation II contain a high percentage of calcium salt in the composition, and are calcium salt dense. The respirable dry particles contain at least 40% calcium salt by weight of the dry powder (wt calcium salt/wt dry powder), at least 50% calcium salt by weight of the dry powder, at least 55% calcium salt by weight of the dry powder; at least 60% calcium salt by weight of the dry powder, at least 70% calcium salt by weight of the dry powder, between 40% and 90% calcium salt by weight of the dry powder, between 50% and 85% calcium salt by weight of the dry powder, about 55% or about 80% calcium salt by weight of the dry powder.

The respirable dry powders and dry particles of Formulation I and Formulation II contain a low percentage of sodium in the composition. The respirable dry particles contain less than 4% sodium by weight of the dry powder (wt sodium/wt dry powder), preferably 3% or less sodium by weight of the dry powder, or 2% or less sodium by weight of the dry powder.

The respirable dry particles of Formulations I and II are characterized by the crystalline and amorphous content of the particles. The respirable dry particles can comprise a mixture of amorphous and crystalline content, for example, calcium lactate can be substantially in the amorphous phase while sodium chloride or leucine can be substantially in the crystalline phase. This provides several advantages. For example, the crystalline phase (e.g., crystalline sodium chloride and/or crystalline leucine) can contribute to the stability of the dry particles in the dry state and to the dispersibility characteristics, whereas the amorphous phase (e.g., amorphous calcium salt) can facilitate rapid water uptake and dissolution of the particle upon deposition in the respiratory tract.

The highly dispersible dry powders of Formulation I and Formulation II can be administered with low inhalation energy. In order to relate the dispersion of powder at different inhalation flow rates, volumes, and from inhalers of different resistances, the energy required to perform the inhalation maneuver can be calculated. Inhalation energy can be calculated from the equation E=$R^2Q^2V$ where E is the inhalation energy in Joules, R is the inhaler resistance in kPa$^{1/2}$/LPM, Q is the steady flow rate in L/min and V is the inhaled air volume in L.

The respirable dry powders and dry particles of Formulation I and Formulation II are characterized by a high emitted dose (e.g., CEPM of at least 75%, at least 80%, at least 85%, at least 90%, at least 95%) from a dry powder inhaler when a total inhalation energy of less than about 2 Joules or less than about 1 Joule, or less than about 0.8 Joule, or less than about 0.5 Joule, or less than about 0.3 Joule is applied to the dry powder inhaler. For example, an emitted dose of at least 75%, at least 80%, at least 85%, at least 90%, at least 95% CEPM of Formulation I or Formulation II contained in a unit dose container, containing about 50 mg or about 40 mg of the appropriate formulation, in a dry powder inhaler can be achieved when a total inhalation energy of less than about 1 Joule (e.g., less than about 0.8 Joule, less than about 0.5 Joule, less than about 0.3 Joule) is applied to the dry powder inhaler. An emitted dose of at least about 70% CEPM of respirable dry powder contained in a unit dose container, containing about 50 mg or about 40 mg of the respirable dry powder, in a dry powder inhaler can be achieved when a total inhalation energy of less than about 0.28 Joule is applied to the dry powder inhaler. The dry powder can fill the unit dose container, or the unit dose container can be at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 µl, 770 µl, 680 µl, 480 µl, 360 µl, 270 µl, and 200 µl). Alternatively, the unit dose container can be a blister. The blister can be packaged as a single blister, or as part of a set of blisters, for example, 7 blisters, 14 blisters, 28 blisters, or 30 blisters.

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p.780-'783, 2001) was used to predict maximum and minimum achievable PIFR through 2 dry powder inhalers of resistances 0.021 and 0.032 kPa1/2/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention. For example, a 50 mg dose of Formulation I or Formulation II was found to require only 0.28 Joules to empty more than 70% of the fill weight in a single inhalation. All the adult patient populations listed above were calculated to be able to achieve greater than 2 Joules, 7 times more than the inhalational energy required.

An advantage of the invention is the production of powders that disperse well across a wide range of flowrates and are relatively flowrate independent. The dry particles and powders of the invention enable the use of a simple, passive DPI for a wide patient population.

In particular aspects, the invention is a respirable dry powder containing respirable dry particles of Formulation I, that comprise i) about 20% (w/w) leucine, ii) about 75% (w/w) calcium lactate, and iii) about 5% (w/w) sodium chloride. The respirable dry powder or dry particles of Formulation I are characterized by:

1. VMGD at 1 bar as measured using a HELOS/RODOS system between 1 micron and 3 microns, preferably between 1.5 microns and 2.5 microns or between 2 microns and 3 microns;

2. Hausner Ratio of 2.0 or higher, preferably between 2.0 and 3.2, and more preferably between 2.4 and 3.0;

3. 1 bar/4 bar of 1.5 or less, preferably between 1.0 and 1.2;

4. 0.5 bar/4 bar of 1.5 or less, preferably between 1.0 and 1.3;

5. FPF<5.6 of at least 38%, preferably at least 40% and more preferably at least 50%;

6. FPF<3.4 of at least 20%, preferably at least 30%; and/or 7. tap density of about 0.5 $g/cm^3$ to about 1.2 $g/cm^3$, preferably between about 0.7 $g/cm^3$ and about 1.0 $g/cm^3$.

The respirable dry powder or dry particles of Formulation I can be further characterized by a water content of less then 25% by weight, preferably less than 15% or less than 10% by weight, or less than 5% by weight, and by the presence of a mixture of amorphous and crystalline content, with calcium lactate substantially in the amorphous phase and sodium chloride and/or leucine substantially in the crystalline phase. Alternatively, the calcium lactate and sodium chloride are substantially in the amorphous phase and the leucine is in either the crystalline and/or amorphous phase. In addition, the respirable dry powder or dry particles of Formulation I can be further characterized by an emitted dose of at least about 80% of Formulation I contained in a unit dose container that contains 40 mg or more, or 50 mg or more, of Formulation I, in a dry powder inhaler, when a total inhalation energy of less than about 0.5 Joule is applied to the dry powder inhaler; by an emitted dose of at least about 90% of Formulation I contained in a unit dose container that contains 40 mg or more, or 50 mg or more, of Formulation I, in a dry powder inhaler, when a total inhalation energy of less than about 0.5 Joule is applied to the dry powder inhaler; or by an emitted dose of at least about 95% of Formulation I contained in a unit dose container containing 40 mg or more, or 50 mg or more of Formulation I, in a dry powder inhaler, when a total inhalation energy of less than about 1 Joule is applied to the dry powder inhaler.

In other particular aspects, the invention is a respirable dry powder containing respirable dry particles of Formulation I, that comprise i) about 20% (w/w) leucine, ii) about 75% (w/w) calcium lactate, and iii) about 5% (w/w) sodium chloride, and are characterized by:

1. VMGD at 1 bar as measured using a HELOS/RODOS system between 1 micron and 3 microns, preferably between 1.5 microns and 2.5 microns or between 2 microns and 3 microns;

2. Hausner Ratio of 1.4 or higher;

3. 1 bar/4 bar of 1.5 or less, preferably between 1.0 and 1.2;

4. 0.5 bar/4 bar of 1.5 or less, preferably between 1.0 and 1.3;

5. FPF<5.6 of at least 38%, preferably at least 40% and more preferably at least 50%;

6. FPF<3.4 of at least 20%, preferably at least 30%;

7. tap density of about 0.5 $g/cm^3$ to about 1.2 $g/cm^3$, preferably between about 0.7 $g/cm^3$ and about 1.0 $g/cm^3$; and/or 8. heat of solution of about −6 kcal to about 6 kcal/mol.

In other particular aspects, the invention is a respirable dry powder containing respirable dry particles of Formulation II, that comprise i) about 37.5% (w/w) leucine, ii) about 58.6% (w/w) calcium lactate, and iii) about 3.9% (w/w) sodium chloride.

The respirable dry powder or dry particles of Formulation II are characterized by:

1. VMGD at 1 bar as measured using a HELOS/RODOS system between 1.5 microns and 3 microns, preferably between 2 microns and 3 microns;

2. Hausner Ratio of 1.9 or higher, preferably between 2.0 and 3.0, and more preferably between 2.2 and 2.6;

3. 1 bar/4 bar of 1.5 or less, preferably between 1.0 and 1.2;

4. 0.5 bar/4 bar of 1.5 or less, preferably between 1.0 and 1.3;

5. FPF<5.6 of at least 40%, preferably at least 50%;

6. FPF<3.4 of at least 20%, preferably at least 30%; and/or 7. tap density of about 0.5 g/cm$^3$ to about 1.0 g/cm$^3$, preferably between about 0.6 g/cm$^3$ and about 1.0 g/cm$^3$, or between about 0.7 g/cm$^3$ and about 1.0 g/cm$^3$.

The respirable dry powder or dry particles of Formulation II can be further characterized by a water content of less then 25% by weight, preferably less than 15% or less than 10% by weight, or less than 5% by weight, or less than 2% by weight, and by the presence of a mixture of amorphous and crystalline content, with calcium lactate substantially in the amorphous phase and sodium chloride and/or leucine substantially in the crystalline phase. Alternatively, the calcium lactate and sodium chloride are substantially in the amorphous phase and the leucine is in either the crystalline and/or amorphous phase. In addition, the respirable dry powder or dry particles of Formulation II can be further characterized by an emitted dose of at least about 70% of Formulation II contained in a unit dose container that contains 50 mg or more of Formulation II, in a dry powder inhaler is achieved when a total inhalation energy of less than about 0.5 Joule is applied to the dry powder inhaler; or by an emitted dose of at least about 80% of Formulation II contained in a unit dose containing 50 mg or more of Formulation II, in a dry powder inhaler is achieved when a total inhalation energy of less than about 1 Joule is applied to the dry powder inhaler.

The respirable dry particles and dry powders described herein are suitable for inhalation therapies. The respirable dry particles may be fabricated with the appropriate surface roughness, diameter and tap density for localized delivery to selected regions of the respiratory system such as the deep lung or upper or central airways.

If desired, the respirable dry powders and/or dry particles of Formulations I and II can include one or more additional agents, such as mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). The additional agent can be blended with a dry powder of Formulation I or II or co-spray dried as desired.

In some embodiments, the salt formulation can contain an agents that disrupt and/or disperse biofilms. Suitable examples of agents to promote disruption and/or dispersion of biofilms include specific amino acid stereoisomers, e.g. D-leucine, D-methionine, D-tyrosine, D-tryptophan, and the like. (Kolodkin-Gal, I., D. Romero, et al. "D-amino acids trigger biofilm disassembly." Science 328(5978): 627-629.) For example, all or a portion of the leucine in the dry powders described herein (e.g., Formulation I, Formulation II and formultions based on Formulation I or II) can be D-leucine.

Examples of suitable mucoactive or mucolytic agents include MUC5AC and MUC5B mucins, DNA-ase, N-acetylcysteine (NAC), cysteine, nacystelyn, dornase alfa, gelsolin, heparin, heparin sulfate, P2Y2 agonists (e.g. UTP, INS365), nedocromil sodium, hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the salt formulation can contain an antibiotic. The antibiotic can be suitable for treating any desired bacterial infection, and salt formulations that contain an antibiotic can be used to reduce the spread of infection, either within a patient or from patient to patient. For example, salt formulations for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-*mycobacterium* antibiotics and the like.

If desired, the salt formulation can contain an agent for treating infections with mycobacteria, such as *Mycobacterium tuberculosis*. Suitable agents for treating infections with mycobacteria (e.g., *M. tuberculosis*) include an aminoglycoside (e.g. capreomycin, kanamycin, streptomycin), a fluoroquinolone (e.g. ciprofloxacin, levofloxacin, moxifloxacin), isozianid and isozianid analogs (e.g. ethionamide), aminosalicylate, cycloserine, diarylquinoline, ethambutol, pyrazinamide, protionamide, rifampin, and the like.

If desired, the salt formulation can contain a suitable antiviral agent, such as oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, and acyclovir. The salt formulation can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting beta$_2$ agonists, long-acting beta$_2$ agonists (LABA), long-acting muscarinic antagonists (LAMA), combinations of LABAs and LAMAs, methylxanthines, short-acting anticholinergic agents (may also be referred to as short acting anti-muscarinic), and the like.

Suitable short-acting beta$_2$ agonists include albuterol, epinephrine, pirbuterol, levalbuterol, metaproteronol, maxair, and the like.

Examples of albuterol sulfate formulations (also called salbutamol) include Inspiryl (AstraZeneca Plc), Salbutamol SANDOZ (Sanofi-Aventis), Asmasal clickhaler (Vectura Group Plc.), Ventolin® (GlaxoSmithKline Plc), Salbutamol GLAND (GlaxoSmithKline Plc), Airomir® (Teva Pharmaceutical Industries Ltd.), ProAir HFA (Teva Pharmaceutical Industries Ltd.), Salamol (Teva Pharmaceutical Industries Ltd.), Ipramol (Teva Pharmaceutical Industries Ltd), Albuterol sulfate TEVA (Teva Pharmaceutical Industries Ltd), and the like. Examples of epinephrine include Epinephine Mist KING (King Pharmaceuticals, Inc.), and the like. Examples of pirbuterol as pirbuterol acetate include Maxair® (Teva Pharmaceutical Industries Ltd.), and the like. Examples of levalbuterol include Xopenex® (Sepracor), and the like. Examples of metaproterenol formulations as metaproterenol sulfate include Alupent® (Boehringer Ingelheim GmbH), and the like.

Suitable LABAs include salmeterol, formoterol and isomers thereof (e.g. arformoterol), clenbuterol, tulobuterol, vilanterol (Revolair™), indacaterol, carmoterol, isoproterenol, procaterol, bambuterol, milveterol, olodaterol and the like.

Examples of salmeterol formulations include salmeterol xinafoate as Serevent® (GlaxoSmithKline Plc), salmeterol as Inaspir (Laboratorios Almirall, S.A.), Advair® HFA (GlaxoSmithKline PLC), Advair Diskus® (GlaxoSmithKline PLC, Theravance Inc), Plusvent (Laboratorios Almirall, S.A.), VR315 (Novartis, Vectura Group PLC) and the like. Examples of formoterol and isomers formulations (e.g., arformoterol) include Foster (Chiesi Farmaceutici S.p.A), Atimos (Chiesi Farmaceutici S.p.A, Nycomed Internaional Management), Flutiform® (Abbott Laboratories, SkyePharma PLC), MFF258 (Novartis AG), Formoterol clickhaler (Vectura Group PLC), Formoterol HFA (SkyePharma PLC), Oxis® (Astrazeneca PLC), Oxis pMDI (Astrazeneca), Foradil® Aerolizer (Novartis, Schering-Plough Corp, Merck), Foradil® Certihaler (Novartis, SkyePharma PLC), Symbicort® (AstraZeneca), VR632 (Novartis AG, Sandoz International GmbH), MFF258 (Merck & Co Inc, Novartis AG), Alvesco® Combo (Nycomed International Management GmbH, Sanofi-Aventis, Sepracor Inc), Mometasone furoate (Schering-Plough Corp), and the like. Examples of clenbuterol formulations include Ventipulmin® (Boehringer Ingelheim), and the like. Examples of tulobuterol formulations include Hokunalin Tape (Abbott Japan Co., Ltd., Maruho Co., Ltd.), and the like. Examples of vilanterol formulations include Revolair™ (GlaxoSmithKline PLC), GSK64244 (GlaxoSmithKline PLC), and the like. Examples of indacaterol formulations include QAB 149 (Novartis AG, SkyePharma PLC), QMF149 (Merck & Co Inc) and the like. Examples of carmoterol formulations include CHF4226 (Chiese Farmaceutici S.p.A., Mitsubishi Tanabe Pharma Corporation), CHF5188 (Chiesi Farmaceutici S.p.A), and the like. Examples of isoproterenol sulfate formulations include Aludrin (Boehringer Ingelheim GmbH) and the like. Examples of procaterol formulations include Meptin clickhaler (Vectura Group PLC), and the like. Examples of bambuterol formulations include Bambec (AstraZeneca PLC), and the like. Examples of milveterol formulations include GSK159797C (GlaxoSmithKline PLC), TD3327 (Theravance Inc), and the like. Examples of olodaterol formulations include BI1744CL (Boehringer Ingelheim GmbH) and the like.

Examples of LAMAs include tiotroprium, trospium chloride, glycopyrrolate, aclidinium, ipratropium and the like.

Examples of tiotroprium formulations include Spiriva® (Boehringer-Ingleheim, Pfizer), and the like. Examples of glycopyrrolate formulations include Robinul® (Wyeth-Ayerst), Robinul Forte (Wyeth-Ayerst), NVA237 (Novartis), and the like. Examples of aclidinium formulations include Eklira® (Forest Labaoratories, Almirall), and the like.

Examples of combinations of LABAs and LAMAs include indacaterol with glycopyrrolate, formoterol with glycopyrrolate, indacaterol with tiotropium, olodaterol and tiotropium, vilanterol with a LAMA, and the like.

Examples of combinations of indacaterol with glycopyrrolate include QVA149A (Novartis), and the like. Examples of combinations of formoterol with glycopyrrolate include PT003 (Pearl Therapeutics) and the like. Examples of combinations of olodaterol with tiotropium include BI1744 with Spiriva (Boehringer Ingelheim) and the like. Examples of combinations of vilanterol with a LAMA include GSK573719 with GSK642444 (GlaxoSmithKline PLC), and the like.

Examples of methylxanthines include aminophylline, ephedrine, theophylline, oxtriphylline, and the like.

Examples of aminophylline formulations include Aminophylline BOEHRINGER (Boehringer Ingelheim GmbH) and the like. Examples of ephedrine formulations include Bronkaid® (Bayer AG), Broncholate (Sanofi-Aventis), Primatene® (Wyeth), Tedral SA®, Marax (Pfizer Inc) and the like. Examples of theophylline formulations include Euphyllin (Nycomed International Management GmbH), Theo-dur (Pfizer Inc, Teva Pharmacetuical Industries Ltd) and the like. Examples of oxtriphylline formulations include Choledyl SA (Pfizer Inc) and the like.

Examples of short-acting anticholinergic agents include ipratropium bromide, oxitropium bromide, and tiotropium (Spiriva).

Examples of ipratropium bromide formulations include Atrovent®/Apovent/Inpratropio (Boehringer Ingelheim GmbH), Ipramol (Teva Pharmaceutical Industries Ltd) and the like. Examples of oxitropium bromide include Oxivent (Boehringer Ingelheim GmbH), and the like.

Suitable anti-inflammatory agents include leukotriene inhibitors, phosphodiesterase 4 (PDE4) inhibitors, other anti-inflammatory agents, and the like.

Suitable leukotriene inhibitors include montelukast (cystinyl leukotriene inhibitors), masilukast, zafirleukast (leukotriene D4 and E4 receptor inhibitors), pranlukast, zileuton (5-lipoxygenase inhibitors), and the like.

Examples of montelukast formulations (cystinyl leukotriene inhibitor) include Singulair® (Merck & Co Inc), Loratadine, montelukast sodium SCHERING (Schering-Plough Corp), MK0476C (Merck & Co Inc), and the like. Examples of masilukast formulations include MCC847 (AstraZeneca PLC), and the like. Examples of zafirlukast formulations (leukotriene D4 and E4 receptor inhibitor) include Accolate® (AstraZeneca PLC), and the like. Examples of pranlukast formulations include Azlaire (Schering-Plough Corp). Examples of zileuton (5-LO) formulations include Zyflo® (Abbott Laboratories), Zyflo CR® (Abbott Laboratories, SkyePharma PLC), Zileuton ABBOTT LABS (Abbott Laboratories), and the like. Suitable PDE4 inhibitors include cilomilast, roflumilast, oglemilast, tofimilast, and the like.

Examples of cilomilast formulations include Ariflo (GlaxoSmithKline PLC), and the like. Examples of roflumilast include Daxas® (Nycomed International Management GmbH, Pfizer Inc), APTA2217 (Mitsubishi Tanabe Pharma Corporation), and the like. Examples of oglemilast formulations include GRC3886 (Forest Laboratories Inc), and the like. Examples of tofimilast formulations include Tofimilast PFIZER INC (Pfizer Inc), and the like.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor formulations such as AZD9668 (neutrophil elastase inhibitor, from AstraZeneca), GW856553X Losmapimod (P38 kinase inhibitor, GlaxoSmithKline PLC), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), Corus (inhaled lidocaine to decrease eosinophils, Gilead Sciences Inc), Prograf® (IL-2-mediated T-cell activation inhibitor, Astellas Pharma), Bimosiamose PFIZER INC (selectin inhibitor, Pfizer Inc), R411 (α4 β1/α4 β7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-C5, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol (β2-adrenoceptor antagonist) and tiotropium, Boehringer Ingelheim GmbH), NFκ-B inhibitors, CXR2 antagaonists, HLE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-α, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), growth factors (e.g., GM-CSF, NGF, SCF, TGF-β, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNFα, Centocor, Inc, Johnson & Johnson, Schering-Plough Corp); Canakinumab (IL-1β, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENETECH (Genetech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like.

Suitable steroids include corticosteroids, combinations of corticosteroids and LABAs, combinations of corticosteroids and LAMAs, combinations of corticosteroids with LABAs and LAMAs, and the like.

Suitable corticosteroids include budesonide, fluticasone, flunisolide, triamcinolone, beclomethasone, mometasone, ciclesonide, dexamethasone, and the like.

Examples of budesonide formulations include Captisol-Enabled Budesonide Solution for Nebulization (AstraZeneca PLC), Pulmicort® (AstraZeneca PLC), Pulmicort® Flexhaler (AstraZeneca Plc), Pulmicort® HFA-MDI (AstraZeneca PLC), Pulmicort Respules® (AstraZeneca PLC), Inflammide (Boehringer Ingelheim GmbH), Pulmicort® HFA-MDI (SkyePharma PLC), Unit Dose Budesonide ASTRAZENECA (AstraZeneca PLC), Budesonide Modulite (Chiesi Farmaceutici S.p.A), CHF5188 (Chiesi Farmaceutici S.p.A), Budesonide ABBOTT LABS (Abbott Laboratories), Budesonide clickhaler (Vestura Group PLC), Miflonide (Novartis AG), Xavin (Teva Pharmaceutical Industries Ltd.), Budesonide TEVA (Teva Pharmaceutical Industries Ltd.), Symbicort® (AstraZeneca K.K., AstraZeneca PLC), VR632 (Novartis AG, Sandoz International GmbH), and the like.

Examples of fluticasone propionate formulations include Flixotide Evohaler (GlaxoSmithKline PLC), Flixotide Nebules (GlaxoSmithKline Plc), Flovent® (GlaxoSmithKline Plc), Flovent® Diskus (GlaxoSmithKline PLC), Flovent® HFA (GlaxoSmithKline PLC), Flovent® Rotadisk (GlaxoSmithKline PLC), Advair® HFA (GlaxoSmithKline PLC, Theravance Inc), Advair Diskus® (GlaxoSmithKline PLC, Theravance Inc.), VR315 (Novartis AG, Vectura Group PLC, Sandoz International GmbH), and the like. Other formulations of fluticasone include fluticasone as Flusonal (Laboratorios Almirall, S.A.), fluticasone furoate as GW685698 (GlaxoSmithKline PLC, Thervance Inc.), Plusvent (Laboratorios Almirall, S.A.), Flutiform® (Abbott Laboratories, SkyePharma PLC), and the like.

Examples of flunisolide formulations include Aerobid® (Forest Laboratories Inc), Aerospan® (Forest Laboratories Inc), and the like. Examples of triamcinolone formulations include Triamcinolone ABBOTT LABS (Abbott Laboratories), Azmacort® (Abbott Laboratories, Sanofi-Aventis), and the like. Examples of beclomethasone dipropionate formulations include Beclovent (GlaxoSmithKline PLC), QVAR® (Johnson & Johnson, Schering-Plough Corp, Teva Pharmacetucial Industries Ltd), Asmabec clickhaler (Vectura Group PLC), Beclomethasone TEVA (Teva Pharmaceutical Industries Ltd), Vanceril (Schering-Plough Corp), BDP Modulite (Chiesi Farmaceutici S.p.A.), Clenil (Chiesi Farmaceutici S.p.A), Beclomethasone dipropionate TEVA (Teva Pharmaceutical Industries Ltd), and the like. Examples of mometasone include QAB 149 Mometasone furoate (Schering-Plough Corp), QMF149 (Novartis AG), Fomoterol fumarate, mometoasone furoate (Schering-Plough Corp), MFF258 (Novartis AG, Merck & Co Inc), Asmanex® Twisthaler (Schering-Plough Corp), and the like. Examples of cirlesonide formulations include Alvesco® (Nycomed International Management GmbH, Sepracor, Sanofi-Aventis, Tejin Pharma Limited), Alvesco® Combo (Nycomed International Management GmbH, Sanofi-Aventis), Alvesco® HFA (Nycomed Intenational Management GmbH, Sepracor Inc), and the like. Examples of dexamethasone formulations include DexPak® (Merck), Decadron® (Merck), Adrenocot, CPC-Cort-D, Decaject-10, Solurex and the like. Other corticosteroids include Etiprednol dicloacetate TEVA (Teva Pharmaceutical Industries Ltd), and the like.

Combinations of corticosteroids and LABAs include salmeterol with fluticasone, formoterol with budesonide, formoterol with fluticasone, formoterol with mometasone, indacaterol with mometasone, and the like.

Examples of salmeterol with fluticasone include Plusvent (Laboratorios Almirall, S.A.), Advair® HFA (GlaxoSmithKline PLC), Advair® Diskus (GlaxoSmithKline PLV, Theravance Inc), VR315 (Novartis AG, Vectura Group PLC, Sandoz International GmbH) and the like. Examples of vilanterol with fluticasone include GSK642444 with fluticasone and the like. Examples of formoterol with budesonide include Symbicort® (AstraZeneca PLC), VR632 (Novartis AG, Vectura Group PLC), and the like. Examples of formoterol with fluticasone include Flutiform® (Abbott Laboratories, SkyePharma PLC), and the like. Examples of formoterol with mometasone include Dulera®/MFF258 (Novartis AG, Merck & Co Inc), and the like. Examples of indacaterol with mometasone include QAB 149 Mometasone furoate (Schering-Plough Corp), QMF149 (Novartis AG), and the like. Combinations of corticosteroids with LAMAs include fluticasone with tiotropium, budesonide with tiotropium, mometasone with tiotropium, salmeterol with tiotropium, formoterol with tiotropium, indacaterol with tiotropium, vilanterol with tiotropium, and the like. Combinations of corticosteroids with LAMAs and LABAs include fluticasone with salmeterol and tiotropium.

Other anti-asthma molecules include: ARD111421 (VIP agonist, AstraZeneca PLC), AVE0547 (anti-inflammatory, Sanofi-Aventis), AVE0675 (TLR agonist, Pfizer, Sanofi-Aventis), AVE0950 (Syk inhibitor, Sanofi-Aventis), AVE5883 (NK1/NK2 antagonist, Sanofi-Aventis), AVE8923 (tryptase beta inhibitor, Sanofi-Aventis), CGS21680 (adenosine A2A receptor agonist, Novartis AG), ATL844 (A2B receptor antagonist, Novartis AG), BAY443428 (tryptase inhibitor, Bayer AG), CHF5407 (M3 receptor inhibitor, Chiesi Farmaceutici S.p.A.), CPLA2 Inhibitor WYETH (CPLA2 inhibitor, Wyeth), IMA-638 (IL-13 antagonist, Wyeth), LAS100977 (LABA, Laboratorios Almirall, S.A.), MABA (M3 and β2 receptor antagonist, Chiesi Farmaceutici S.p.A), R1671 (mAb, Roche Holding Ltd), CS003 (Neurokinin receptor antagonist, Daiichi Sankyo Company, Limited), DPC168 (CCR antagonist, Bristol-Myers Squibb), E26 (anti-IgE, Genentech Inc), HAE1 (Genentech), IgE inhibitor AMGEN (Amgen Inc), AMG853 (CRTH2 and D2 receptor antagonist, Amgen), IPL576092 (LSAID, Sanofi-Aventis), EPI2010 (antisense adenosine 1, Chiesi Farmaceutici S.p.A.), CHF5480 (PDE-4 inhibitor, Chiesi Farmaceutici S.p.A.), KI04204 (corticosteroid, Abbott Laboratories), SVT47060 (Laboratorios Salvat, S.A.), VML530 (leukotriene synthesis inhibitor, Abbott Laboratories), LAS35201 (M3 receptor antagonist, Laboratorios Almirall, S.A.), MCC847 (D4 receptor antagonist, Mitsubishi Tanabe Pharma Corporation), MEM1414 (PDE-4 inhibitor, Roche), TA270 (5-LO inhibitor, Chugai Pharmaceutical Co Ltd), TAK661 (eosinophil chemotaxis inhibitor, Takeda Pharmaceutical Company Limited), TBC4746 (VLA-4 antagonist, Schering-Plough Corp), VR694 (Vectura Group PLC), PLD177 (steroid, Vectura Group PLC), KI03219 (corticosteroid+LABA, Abbott Laboratories), AMG009 (Amgen Inc), AMG853 (D2 receptor antagonist, Amgen Inc);

AstraZeneca PLC: AZD1744 (CCR3/histamine-1 receptor antagonist, AZD1419 (TLR9 agonist), Mast Cell inhibitor ASTRAZENECA, AZD3778 (CCR antagonist), DSP3025 (TLR7 agonist), AZD1981 (CRTh2 receptor antagonist), AZD5985 (CRTh2 antagonist), AZD8075 (CRTh2 antagonist), AZD1678, AZD2098, AZD2392, AZD3825 AZD8848, AZD9215, ZD2138 (5-LO inhibitor), AZD3199 (LABA);

GlaxoSmithKline PLC: GW328267 (adenosine A2 receptor agonist), GW559090 (a4 integrin antagonist), GSK679586 (mAb), GSK597901 (adrenergic β2 agonist), AM103 (5-LO inhibitor), GSK256006 (PDE4 inhibitor), GW842470 (PDE-4 inhibitor), GSK870086 (glucocorticoid agonist), GSK159802 (LABA), GSK256066 (PDE-4 inhibitor), GSK642444 (LABA, adrenergic β2 agonist), GSK64244 and Revolair (fluticasone/vilanterol), GSK799943 (corticosteroid), GSK573719 (mAchR antagonist), and GSK573719.

Pfizer Inc: PF3526299, PF3893787, PF4191834 (FLAP antagonist), PF610355 (adrenergic β2 agonist), CP664511 (α4β1/VCAM-1 interaction inhibitor), CP609643 (inhibitor of α4β1/VCAM-1 interactions), CP690550 (JAK3 inhibitor), SAR21609 (TLR9 agonist), AVE7279 (Th1 switching), TBC4746 (VLA-4 antagonist); R343 (IgE receptor signaling inhibitor), SEP42960 (adenosine A3 antagonist);

Sanofi-Aventis: MLN6095 (CrTH2 inhibitor), SAR137272 (A3 antagonist), SAR21609 (TLR9 agonist), SAR389644 (DP1 receptor antagonist), SAR398171 (CRTH2 antagonist), SSR161421 (adenosine A3 receptor antagonist);

Merck & Co Inc: MK0633, MK0633, MK0591 (5-LO inhibitor), MK886 (leukotriene inhibitor), BI01211 (VLA-4 antagonist); Novartis AG: QAE397 (long-acting corticosteroid), QAK423, QAN747, QAP642 (CCR3 antagonist), QAX935 (TLR9 agonist), NVA237 (LAMA).

Suitable expectorants include guaifenesin, guaiacolculfonate, ammonium chloride, potassium iodide, tyloxapol, antimony pentasulfide and the like.

Suitable vaccines include nasally inhaled influenza vaccines and the like.

Suitable macromolecules include proteins and large peptides, polysaccharides and oligosaccharides, and DNA and RNA nucleic acid molecules and their analogs having therapeutic, prophylactic or diagnostic activities. Proteins can include antibodies such as monoclonal antibodies. Nucleic acid molecules include genes, antisense molecules such as siRNAs that bind to complementary DNA, RNAi, shRNA, microRNA, RNA, or ribosomes to inhibit transcription or translation. Preferred macromolecules have a molecular weight of at least 800 Da, at least 3000 Da or at least 5000 Da.

Selected macromolecule drugs for systemic applications: Ventavis® (Iloprost), Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, Interferon Alpha, Interferon Beta, Interferon Gamma, Luteinizing Hormone Releasing Hormone (LHRH), follicle stimulating hormone (FSH), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclease (DNase), Heparin, Bactericidal/Permeability Increasing Protein (BPI), Anti-Cytomegalovirus (CMV) Antibody, Interleukin-1 Receptor Antagonist, and the like. GLP-1 analogs (liraglutide, exenatide, etc.), Domain antibodies (dAbs), Pramlintide acetate (Symlin), Leptin analogs, Synagis (palivizumab, MedImmune) and cisplatin.

Selected therapeutics helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, aztreonam and the like. Another exemplary antibiotic/macrolide is levofloxacin. Suitable examples of bronchodilators include inhaled short-acting beta$_2$ agonists such as albuterol, and the like. Suitable examples of inhaled LABAs include salmeterol, formoterol, and the like. Suitable examples of agents to promote airway secretion clearance include Pulmozyme (dornase alfa, Genetech), hypertonic saline, DNase, heparin and the like. Selected therapeutics helpful for the prevention and/or treatment of CF include VX-770 (Vertex Pharmaceuticals) and amiloride.

Selected therapeutics helpful for the treatment of idiopathic pulmonary fibrosis include Metelimumab (CAT-192) (TGF-β1 mAb inhibitor, Genzyme), Aerovant™ (AER001, pitrakinra) (Dual IL-13, IL-4 protein antagonist, Aerovance), Aeroderm™ (PEGylated Aerovant, Aerovance), microRNA, RNAi, and the like.

In preferred embodiments, the respirable dry powder or respirable dry particle comprises an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-*mycobacterium* antibiotics, tobramycin, azithromycin, ciprofloxacin, colistin, and the like. In a further preferred embodiment, the respirable dry powder or respirable dry particle comprises levofloxacin. In a further preferred embodiment, the respirable dry powder or respirable dry particle comprises Cayston®. In a further preferred embodiment, the respirable dry powder or respirable dry particle does not comprise tobramycin. In a further preferred embodiment, the respirable dry powder or respirable dry particle does not comprise levofloxacin. In a further preferred embodiment, the respirable dry powder or respirable dry particle does not comprise Cayston®.

In preferred embodiments, the respirable dry powder or respirable dry particle comprises a LABA, such as salmeterol, formoterol and isomers thereof (e.g., arformoterol), clenbuterol, tulobuterol, vilanterol (Revolair™), indacaterol, carmoterol, isoproterenol, procaterol, bambuterol, milveterol, and the like. In a further preferred embodiment, the respirable dry powder or respirable dry particle comprises formoterol. In a further preferred embodiment, the respirable dry powder or respirable dry particle comprises salmeterol.

In preferred embodiments, the respirable dry powder or respirable dry particle comprises a LAMA, such as tiotroprium, glycopyrrolate, aclidinium, ipratropium and the like.

In a further preferred embodiment, the respirable dry powder or respirable dry particle comprises tiotropium.

In preferred embodiments, the respirable dry powder or respirable dry particle comprises a corticosteroid, such as budesonide, fluticasone, flunisolide, triamcinolone, beclomethasone, mometasone, ciclesonide, dexamethasone, and the like. In a further preferred embodiment, the respirable dry powder or respirable dry particle comprises fluticasone.

In preferred embodiments, the respirable dry powder or respirable dry particle comprises a combination of two or more of the following; a LABA, a LAMA, and a corticosteroid. In a further preferred embodiment, the respirable dry powder or respirable dry particle comprises fluticasone and salmeterol. In a further preferred embodiment, the respirable dry powder or respirable dry particle comprises fluticasone, salmeterol, and tiotropium.

When an additional therapeutic agent is administered to a patient with Formulation I or II, the agent and the Formulation can be administered to provide substantial overlap of pharmacological activity, and the additional therapeutic agent can be administered to the patient before, substantially at the same time, or after Formulation I or II. For example a LABA such as formoterol, or a short-acting beta agonist such as albuterol can be administered to the patient before Formulation I or II, or a dry powder based on Formulation I or II, is administered. A dry powder of the invention (e.g., Formulation I or II) and an additional therapeutic agent can be administered at substantially the same time as two or more separate formulations or as a single formulation (e.g., a blended dry powder, a dry powder formed by co-spraydrying the components of Formulation I and II with an additional therapeutic agent).

In preferred embodiments, the respirable dry powder or respirable dry particle does not comprise a surfactant, such as DPPC, DPPG, DPPS, DSPC, DSPE, and POPC.

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 30%, less than 25%, less than 20%, less than 15%, less than 10%, or less than 5% humidity. The respirable dry powders and respirable dry particles can be packaged (e.g., in sealed capsules, blisters, vials) under these conditions.

In preferred embodiments, the respirable dry powders or respirable dry particles of the invention possess aerosol characteristics that permit effective delivery of the respirable dry particles to the respiratory system without the use of propellants.

The dry particles of the invention can be blended with an active ingredient or co-formulated with an active ingredient to maintain the characteristic high dispersibility of the dry particles and dry powders of the invention. Such blended or co-formulated preparations can be produced in a variety of ways. For example, respirable dry particles of the invention can be blended with an additional therapeutic agent or the components of Formulation I or Formulation II can be co-spray dried with an additional therapeutic agent, such as any one or combination of the additional therapeutic agents disclosed herein, to produce a dry powder. Blended dry powders contain particles of Formulation I and/or II and particles that contain an additional therapeutic agent. Preferred additional therapeutic agents are LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

Dry powders can be prepared by co-spray drying an additional therapeutic agent with the calcium lactate and sodium chloride components, and optionally all or a portion of the leucine component of Formulation I or Formulation II. When it is desirable to retain the relative proportions of calcium lactate, sodium chloride and leucine from Formulation I or II, the additional therapeutic agent can be added to a solution of Formulation I or Formulation II and the resulting solution spray dried to produce dry particles that contain the additional therapeutic agent. In such particles the amount of calcium lactate, sodium chloride and leucine in the dry particles will each be lower than the amounts in Formulation I or II, due to the addition of the additional therapeutic agent. In one example, the formulation can contain up to about 20% (w/w) additional therapeutic agent, and the amount of each of calcium lactate, sodium chloride and leucine are reduced proportionally, but the ratio of the amounts (wt %) of calcium lactate:sodium chloride:leucine is the same as in Formulation I or II. In another example, the formulation can contain up to about 6% (w/w) additional therapeutic agent. In a further example, the formulation can contain up to about 1% (w/w) additional therapeutic agent.

In exemplary embodiments, the dry particles are based on Formulation I and contain up to about 6% (w/w) of one or more additional therapeutic agents, about 70% to about 75% (w/w) calcium lactate, about 3% to about 5% (w/w) sodium chloride and about 17% to about 20% (w/w) leucine. In other exemplary embodiments, the dry particles are based on Formulation II and contain up to about 6% (w/w) of one or more additional therapeutic agent, about 45.0% to about 58.6% (w/w) calcium lactate, about 1.0% to about 3.9% (w/w) sodium chloride and about 27.5% to about 37.5% (w/w) leucine. In further exemplary embodiments, the dry particles are based on Formulation I and contain up to about 20% (w/w) of one or more additional therapeutic agents, about 60% to about 75% (w/w) calcium lactate, about 2% to about 5% (w/w) sodium chloride and about 15% to about 20% (w/w) leucine. In other exemplary embodiments, the dry particles are based on Formulation II and contain up to about 20% (w/w) of one or more additional therapeutic agent, about 54.6% to about 58.6% (w/w) calcium lactate, about 1.9% to about 3.9% (w/w) sodium chloride and about 34.5% to about 37.5% (w/w) leucine. When the additional therapeutic agent is potent, a small amount may be used such as 0.01% to about 1% (w/w), and the composition of the dry particles is substantially the same as Formulation I or II. The additional therapeutic agent can be any of the additional therapeutic agents described herein. Preferred additional therapeutic agents are LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof.

In some dry powder that contain an additional therapeutic agent, all or a portion of the leucine component in Formulation I or II is replaced with one or more additional therapeutic agents. This approach is particularly advantageous for additional therapeutic agents that require a higher effective dose, e.g., are not highly potent, and produces dry particles that deliver the beneficial effects of calcium cation in the respiratory tract and of the beneficial effects of the additional therapeutic agent(s). In exemplary embodiments, the dry particles are based on Formulation I and contain about 0.01% to about 20% (w/w) of one or more additional therapeutic agent, about 75% (w/w) calcium lactate, about 5% (w/w) sodium chloride and about 20% (w/w) or less leucine. In other exemplary embodiments, the dry particles are based on Formulation II and contain about 0.01% to about 37.5% (w/w) of one or more additional therapeutic agents, about 58.6% (w/w) calcium lactate, about 3.9% (w/w) sodium chloride and about 37.5% (w/w) or less leucine. The additional therapeutic agent can be any of the additional therapeutic agents described herein. Preferred additional therapeutic agent are LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof. Particular examples of dry powder of this type are disclosed herein as Formulations X through XX.

In one aspect, salts of divalent cations (e.g., calcium, magnesium) can be co-formulated with a non-calcium active agent, to make small, highly dispersible powders or large, porous particles. Optionally, these particles may include a monovalent cationic salt (e.g., sodium, potassium), and also optionally an excipient (e.g., leucine, maltodextrin, mannitol, lactose). The components can be mixed (e.g., mixed as one solution, static mixed as two solutions) together in order to produce a single particle after spray drying.

In another aspect, the dry particles of the invention are large, porous, and are dispersible. The size of the dry particles can be expressed in a variety of ways. The particles may have VMGD between 5 to 30 µm, or between 5 and 20 µm, with a tap density of less than 0.5 g/cc, preferably less than 0.4 g/cc.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, spray-freeze drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystallization, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. When hot air is used, the moisture in the air is at least partially removed before its use. When nitrogen is used, the nitrogen gas can be run "dry", meaning that no additional water vapor is combined with the gas. If desired the moisture level of the nitrogen or air can be set before the beginning of spry dry run at a fixed value above "dry" nitrogen. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. The nozzle can be a two-fluid nozzle, which is in an internal mixing setup or an external mixing setup. Alternatively, a rotary atomizer having a 4- or 24-vaned wheel may be used. Examples of suitable spray dryers that can be outfitted with either a rotary atomizer or a nozzle, include, a Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. Another preferable range is between 130° C. to about 200° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. Another preferable range is between 65° C. to about 110° C., preferably about 75° C. to about 100° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophillic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer. Alternatively, the atomizing step is performed on a bulk mixed solution.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The invention also relates to respirable dry powders or respirable dry particles produced by preparing a feedstock solution, emulsion or suspension and spray drying the feedstock according to the methods described herein, and to the methods described herein. The feedstock can be prepared using (a) calcium lactate in an amount of about 58.6% or 75% by weight (e.g., of total solutes used for preparing the feedstock) and (b) sodium chloride in an amount of at least about 3.9% or 5% by weight (e.g., of total solutes used for preparing the feedstock) and leucine in an amount of about 37.5% or 20% by weight (e.g., of total solutes used for preparing the feedstock). Any suitable form of calcium lactate can be used to prepare the feedstock, such as calcium lactate pentahydrate. All weight percentages are given on a dry (anhydrous) basis.

In an embodiment, the respirable dry powders or respirable dry particles of the invention can be obtained by (1) preparing a feedstock comprising (a) a dry solute containing in percent by weight of the total dry solute about 37.5% leucine, about 58.6% calcium lactate and about 3.9% sodium chloride and (b) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 20% leucine, about 75% calcium lactate and about 5% sodium chloride and (b) one or more suitable solvents for dissolution of the solute and formation of the feedstock, and (2) spray drying the feedstock. Various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents.

The diameter of the respirable dry particles, for example, their VMGD, can be measured using an electrical zone sensing instrument such as a Multisizer IIe, (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, Minn.) can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor and the multistage liquid impinger (MSLI) methods. The methods and instruments for measuring particle aerodynamic diameter are well known in the art.

Tap density is a measure of the envelope mass density characterizing a particle. Tap density is accepted in the field as an approximation of the envelope mass density of a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., 10$^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min The FPF(<5.6) has been demonstrated to correlate to the fraction of the powder that is able to make it into the lungs of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can be called the capsule emitted powder mass (CEPM) or sometimes termed "shot-weight".

A Multi-Stage Liquid Impinger (MSLI) is another device that can be used to measure fine particle fraction. The Multi-Stage Liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The geometric particle size distribution can be measured for the respirable dry powder after being emitted from a dry powder inhaler (DPI) by use of a laser diffraction instrument such as the Malvern Spraytec. With the inhaler adapter in the closed-bench configuration, an airtight seal is made to the DPI, causing the outlet aerosol to pass perpendicularly through the laser beam as an internal flow. In this way, known flow rates can be drawn through the DPI by vacuum pressure to empty the DPI. The resulting geometric particle size distribution of the aerosol is measured by the photodetectors with samples typically taken at 1000 Hz for the duration of the inhalation and the DV50, GSD, FPF<5.0 µm measured and averaged over the duration of the inhalation.

The invention also relates to a respirable dry powder or respirable dry particles produced using any of the methods described herein.

The respirable dry particles of the invention can also be characterized by the chemical stability of the salts or the excipients that the respirable dry particles comprise. The chemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period of time.

Therapeutic Use and Methods

The respirable dry powders and respirable dry particles of the present invention are suited for administration to the respiratory tract. The dry powders and dry particles of the invention can be administered to a subject in need thereof for the treatment of respiratory (e.g., pulmonary) diseases, such as asthma, airway hyperresponsiveness, seasonal allergic allergy, brochiectasis, chronic bronchitis, emphysema, chronic obstructive pulmonary disease, cystic fibrosis, pulmonary parenchyl inflammatory conditions and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like). Similarly, the respirable dry particles or dry powders can be administered to a subject in need thereof to prevent or treat chronic infections like bacterial colonization and biofilm formation that is often seen in those with chronic respiratory diseases like cystic fibrosis and chronic obstructive pulmonary disease. Without wishing to be bound by particular theory, it is believed that the respirable dry particles or dry powders described herein may activate cation-regulated ion channels like, for example, TRP channels (e.g., TRPV, TRPC, TRPM, TRPA channels) and mediate the eventual induction of antimicrobial defenses like, for example, the secrection of antimicrobial peptides (e.g., alpha-, beta-, theta-defensins), thereby preventing and/or treating microbial infections.

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP; health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like).

The respirable dry particles and dry powder can be administered to alter the biophysical and/or biological properties of the mucosal lining of the respiratory tract (e.g, the airway lining fluid) and underlying tissue (e.g., respiratory tract epithelium). These properties include, for example, gelation at the mucus surface, surface tension of the mucosal lining, surface elasticity and/or viscosity of the mucosal lining, and bulk elasticity and/or viscosity of the mucosal lining Without wishing to be bound by a particular theory, it is believed that the benefits produced by the respirable dry particles or dry powder and the methods described herein (e.g., therapeutic and prophylactic benefits), result from an increase in the amount of calcium cation ($Ca^{2+}$ provided by the calcium salts in the respirable dry particles or dry powder) in the respiratory tract (e.g., lung mucus or airway lining fluid) after administration of the respirable dry particles or dry powder.

The respirable dry powders and dry particles can be administered to increase the rate of mucociliary clearance. Clearance of microbes and inhaled particles is an important function of airways to prevent respiratory infection and exposure to or systemic absorption of potentially noxious agents. This is performed as an integrated function by epithelial, mucus-secreting, and immunologic response cells present at the airway surface. It prominently includes the cilia at the epithelial cell airway surface, whose function is to beat synchronously to transport the overlying liquid mucus blanket proximally (toward the mouth), where it exits the airway and is swallowed or expectorated.

The respirable dry powders and dry particles can be administered to assist in all of these functions. By increasing surface viscoelasticity, the respirable dry powders and dry particles retain microbes and particulates at the surface of the airway mucus blanket, where they do not gain systemic exposure to the host. Hypertonic dry powders and dry particles induce water/liquid transport out of the airway epithelial cells, making the periciliary liquid layer less viscous and rendering ciliary beating more effective in moving and clearing the overlying mucus blanket. Dry particles and dry powders that contain calcium salts as the pharmacologically active agent, also cause an increase in both ciliary beat frequency and the force or vigor of ciliary contractions, with resultant increase in clearance velocity of the overlying mucus stream.

Mucociliary clearance is measured by a well-established technique that measures the function and speed of clearance quantitatively using safe, inhaled radioisotope preparation (e.g., Technitium ($^{99m}$Tc)) in solution. The radioisotope is measured quantitatively by external scintigraphy. Serial measurements over minutes to several hours allow for the assessment of velocity of clearance and effect of a drug vs. baseline/control value.

In some aspects, the invention is a method for treating pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for treating and/or reducing the severity of pulmonary parenchyal inflammatory/fibrotic conditions, such as idiopathic pulmonary fibrosis, pulmonary interstitial inflammatory conditions (e.g., sarcoidosis, allergic interstitial pneumonitis (e.g., Farmer's Lung)), fibrogenic dust interstitial diseases (e.g., asbestosis, silicosis, beryliosis), eosinophilic granulomatosis/histiocytosis X, collagen vascular diseases (e.g., rheumatoid arthritis, scleroderma, lupus), Wegner's granulomatosis, and the like, comprising administering to the respiratory tract of a subject in need thereof an effective amount of respirable dry particles or dry powder, as described herein.

In other aspects, the invention is a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for treating, preventing and/or reducing contagion of an infectious disease of the respiratory tract, comprising administering to the respiratory tract of a subject in need thereof an effective amount of respirable dry particles or dry powder, as described herein.

In other aspects, the invention is a method for reducing inflammation comprising administering to the respiratory tract of a subject in need thereof an effective amount of respirable dry particles or dry powders as described herein. Thus, the respirable dry particles and dry powders can be used to broadly prevent or treat acute and/or chronic inflammation and, in particular, inflammation that characterizes a number of pulmonary diseases and conditions including, asthma, airway hyperresponsiveness, seasonal allergic allergy, bronchiectasis, chronic bronchitis, emphysema, chronic obstructive pulmonary disease (COPD), cystic fibrosis (CF), pulmonary parenchyal inflammatory diseases/conditions, and the like. The dry particles and dry powders can be administered to prevent or treat both the inflammation inherent to diseases like asthma, COPD and CF and the increased inflammation caused by acute exacerbations of the diseases, both of which play a primary role in the pathogenesis of those diseases.

In certain particular embodiments of the methods described herein, the respirable dry powder (e.g., Formulation I, Formulation II, and/or dry powder based on Formulation I or II that contains an additional therapeutic agent) is administered to a patient who has been pretreated with a bronchodilator, or is administered concurrently with a bronchodilator. When the patient is pretreated with a bronchodilator it is preferred that the respirable dry powder is administered at a time after the bronchodilator when the onset of bronchodilatory effect is evident or, more preferably, maximal. For example, a short acting beta$_2$ agonist such as albuterol, can be administered about 10 minutes to about 30 minutes, preferably, about 15 minutes, prior to administration of the respirable dry powder. Pretreatment with a short acting beta$_2$ agonist such as albuterol is particularly preferred for CF patients. Some patients may already be taking bronchodilators, such as LABAs (e.g., fomoterol). Patients with COPD frequently take LABAs to manage their disease. Patients that are taking LABAs already receive some degree of bronchorelaxation due to the effects of the LABAs, and therefore further bronchodilation (e.g., using a short acting beta$_2$ agonist) may not be required or desired. For these types of patients, respirable dry powder (e.g., Formulation I, Formulation II, and/or dry powder based on Formulation I or II that contains an additional therapeutic agent) can be administered at substantially the same time or concurrently with the LABA, for example, in a single formulation (e.g., the respirable dry powder of Formulation XIX).

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCapss® (Hovione, Loures, Portugal), Inhalators® (Boehringer-Ingelheim, Germany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The respirable dry particles or dry powders can be preferably delivered by inhalation to a desired area within the respiratory tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

In certain embodiments, a dry powder formulation is administered to the small airways. In these embodiments, the dry powder preferably contains respirable particles that have a VMDG and/or MMAD that is suitable for delivery to the small airways, such as a VMGD and/or MMAD of about 0.5 µm to about 3 µm, about 0.75 µm to about 2 µm, or about 1 µm to about 1.5 µm.

It is believed that when some dry powders that contain divalent metal salts as active ingredients are administered, there is a possibility that at least some of the respirable dry powder will deposit in the oral cavity and produce an unpleasant "salty mouth" sensation. It is envisioned that this sensation could lead patients to not comply with therapeutic instructions or to discontinue therapy. An advantage of the respirable dry powders of this invention is that they are small and highly dispersible, and therefore, deposition in the oral cavity is reduced and the occurrence of an unpleasant salty mouth sensation is reduced or prevented.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 μm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 μm, leading to enhanced oral cavity deposition.

Therefore, it is desirable to have a powder in which the particles are small (e.g., MMAD of 5 microns or less, e.g. between 1 to 5 microns), and are highly dispersible (e.g. ¼ bar or alternatively, $^{0.5}$/4 bar of 2.0, and preferably less than 1.5). More preferably, the respirable dry powder is comprised of respirable dry particles with an MMAD between 1 to 4 microns or 1 to 3 microns, and have a ¼ bar ratio of dispersion settings on the RODOS/HELOS of less than 1.4, or less than 1.3, and more preferably less than 1.2.

The absolute geometric diameter of the particles measured at 1 bar dispersion setting using the HELOS/RODOS system is not critical provided that the particle's envelope density is sufficient such that the MMAD is in one of the ranges listed above, wherein MMAD is VMGD times the square root of the envelope density (MMAD=VMGD*sqrt(envelope density)). If it is desired to deliver a high unit dose of salt using a fixed volume dosing container, then, particles of higher envelope density are desired. High envelope density allows for more mass of powder to be contained within the fixed volume dosing container. Preferable envelope densities are greater than 0.1 g/cc, greater than 0.25 g/cc, greater than 0.4 g/cc, greater than 0.5 g/cc, greater than 0.6 g/cc, greater than 0.7 g/cc, and greater than 0.8 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain another active agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The highly dispersible powders of this invention provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

As described herein, it is believed that the therapeutic and prophylactic effects of the respirable dry particles and dry powders are the result of an increased amount of calcium in the respiratory tract (e.g., lung) following administration of respirable dry particles and dry powders.

Generally, an effective amount of a pharmaceutical formulation will deliver a dose of about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body weight/dose, about 0.005 mg $Ca^{+2}$/kg body weight/dose, about 0.01 mg $Ca^{+2}$/kg body weight/dose, about 0.02 mg $Ca^{+2}$/kg body weight/dose, or about 0.5 mg $Ca^{+2}$/kg body weight/dose.

In some embodiments the amount of calcium delivered to the respiratory tract (e.g., lungs, respiratory airway) is about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body weight/dose, about 0.005 mg $Ca^{+2}$/kg body weight/dose, about 0.01 mg $Ca^{+2}$/kg body weight/dose, about 0.02 mg $Ca^{+2}$/kg body weight/dose, or about 0.5 mg $Ca^{+2}$/kg body weight/dose.

In other embodiments the amount of calcium delivered to the upper respiratory tract (e.g., nasal cavity) is of about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body Suitable intervals between doses that provide the desired therapeutic effect can be determined based on the severity of the condition (e.g., infection), overall well being of the subject and the subject's tolerance to respirable dry particles and dry powders and other considerations. Based on these and other considerations, a clinician can determine appropriate intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous, high salt compositions of the invention to take up water at elevated humidities can also be advantageous with respect to their deposition profiles in vivo. Due to their rapid water uptake at high humidities, these powder formulations can undergo hygroscopic growth due to the absorbance of water from the humid air in the respiratory tract as they transit into the lungs. This can result in an increase in their effective aerodynamic diameters during transit into the lungs, which will further facilitate their deposition in the airways.

EXEMPLIFICATION

Materials used in the following Examples and their sources are listed below. Calcium lactate pentahydrate, sodium chloride, and L-leucine were obtained from Sigma-Aldrich Co. (St. Louis, Mo.), Spectrum Chemicals (Gardena, Calif.), or Merck (Darmstadt, Germany). Ultrapure (Type II ASTM) water was from a water purification system (Millipore Corp., Billerica, Mass.), or equivalent.

Methods:

Geometric or Volume Diameter.

Volume median diameter (x50 or Dv50), which may also be referred to as volume median geometric diameter (VMGD), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the dispersion energy may be modulated by changing the regulator pressure from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method, geometric standard deviation (GSD) for the volume diameter was also determined.

Volume median diameter can also be measured using a method where the powder is emitted from a dry powder inhaler device. The equipment consisted of a Spraytec laser diffraction particle size system (Malvern, Worcestershire, UK), "Spraytec". Powder formulations were filled into size 3 HPMC capsules (Capsugel V-Caps) by hand with the fill weight measured gravimetrically using an analytical balance (Mettler Tolerdo XS205). A capsule based passive dry powder inhalers (RS-01 Model 7, High resistance Plastiape S.p.A.) was used which had specific resistance of 0.036 $kPa^{1/2}LPM^{-1}$. Flow rate and inhaled volume were set using a timer controlled solenoid valve with flow control valve (TPK2000, Copley Scientific). Capsules were placed in the dry powder inhaler, punctured and the inhaler sealed to the inlet of the laser diffraction particle sizer. The steady air flow rate through the system was initiated using the TPK2000 and the particle size distribution was measured via the Spraytec at 1 kHz for the durations at least 2 seconds and up to the total inhalation duration. Particle size distribution parameters calculated included the volume median diameter (Dv50) and the geometric standard deviation (GSD) and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration (capsule emitted powder mass or CEPM).

The previous description of the use of the Spraytec was for what is described as its "closed bench configuration". Alternatively, the Spraytec can be used in its "open bench configuration". In the open bench configuration, capsules were placed in the dry powder inhaler, punctured and the inhaler sealed inside a cylinder. The cylinder was connected to a positive pressure air source with steady air flow through the system again measured with a mass flow meter and its duration controlled with a timer controlled solenoid valve. The exit of the dry powder inhaler was exposed to room pressure and the resulting aerosol jet passed through the laser of the diffraction particle sizer (Spraytec) in its open bench configuration before being captured by a vacuum extractor. The steady air flow rate through the system was initiated using the solenoid valve and the particle size distribution was measured via the Spraytec at 1 kHz for the duration of the single inhalation maneuver with a minimum of 2 seconds, as in the closed bench configuration. When data are reported in the examples as being measured by the Spraytec, they are from the open bench configuration unless otherwise noted.

Fine Particle Fraction.

The aerodynamic properties of the powders dispersed from an inhaler device were assessed with an Mk-II 1 ACFM Andersen Cascade Impactor (Copley Scientific Limited, Nottingham, UK). The instrument was run in controlled environmental conditions of 18 to 25° C. and relative humidity (RH) between 20 and 40%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain, called the "final collection filter". Gravimetric and/or chemical analyses can then be performed to determine the particle size distribution. A short stack cascade impactor, also referred to as a collapsed cascade impactor, is also utilized to allow for reduced labor time to evaluate two aerodynamic particle size cut-points. With this collapsed cascade impactor, stages are eliminated except those required to establish fine and coarse particle fractions.

The impaction techniques utilized allowed for the collection of two or eight separate powder fractions. The capsules (HPMC, Size 3; Shionogi Qualicaps, Madrid, Spain or Capsugel Vcaps, Peapack, N.J.) were hand filled with powder to a specific weight and placed in a hand-held, breath-activated dry powder inhaler (DPI) device, the high resistance RS-01 DPI (Plastiape, Osnago, Italy). The capsule was punctured and the powder was drawn through the cascade impactor operated at a flow rate of 60.0 L/min for 2.0 s. At this flowrate, the calibrated cut-off diameters for the eight stages are 8.6, 6.5, 4.4, 3.3, 2.0, 1.1, 0.5 and 0.3 microns and for the two stages used with the short stack cascade impactor, the cut-off diameters are 5.6 microns and 3.4 microns. The fractions were collected by placing filters in the apparatus and determining the amount of powder that impinged on them by gravimetric measurements or chemical measurements on an HPLC, as labeled in the tables. The fine particle fraction of the total dose of powder ($FPF_{TD}$) less than or equal to an effective cut-off aerodynamic diameter was calculated by dividing the powder mass recovered from the desired stages of the impactor by the total particle mass in the capsule. Results are reported as the fine particle fraction of less than 5.6 microns ($FPF_{TD}$<5.6 microns) and the fine particle fraction of less than 3.4 microns ($FPF_{TD}$<3.4 microns). The fine particle fraction can alternatively be calculated relative to the recovered or emitted dose of powder by dividing the powder mass recovered from the desired stages of the impactor by the total powder mass recovered.

Aerodynamic Diameter.

Mass median aerodynamic diameter (MMAD) was determined using the information obtained by the Andersen Cascade Impactor. The cumulative mass under the stage cut-off diameter is calculated for each stage and normalized by the recovered dose of powder. The MMAD of the powder is then calculated by linear interpolation of the stage cut-off diameters that bracket the 50th percentile.

Fine Particle Dose.

The fine particle dose is determined using the information obtained by the ACI. The cumulative mass deposited on the final collection filter, and stages 6, 5, 4, 3, and 2 for a single dose of powder actuated into the ACI is equal to the fine particle dose less than 4.4 microns (FPD<4.4 μm).

Emitted Geometric or Volume Diameter.

The volume median diameter (Dv50) of the powder after it emitted from a dry powder inhaler, which may also be referred to as volume median geometric diameter (VMGD), was determined using a laser diffraction technique via the Spraytec diffractometer (Malvern, Inc.). Powder was filled into size 3 capsules (V-Caps, Capsugel) and placed in a capsule based dry powder inhaler (RS01 Model 7 High resistance, Plastiape, Italy), or DPI, which was connected airtightly to the inhaler adapter of the Spraytec. A steady air flow rate was drawn through the DPI typically at 60 L/min for a set duration, typically of 2 seconds controlled by a timer controlled solenoid (TPK2000, Copley, Scientific, UK). Alternatively, the air flow rate drawn through the DPI was sometimes run at 15 L/min, 20 L/min, or 30 L/min. The outlet aerosol then passed perpendicularly through the laser beam as an internal flow. The resulting geometric particle size distribution of the aerosol was calculated from the software based on the measured scatter pattern on the photodetectors with samples typically taken at 1000 Hz for the duration of the inhalation. The Dv50, GSD, FPF<5.0 μm measured were then averaged over the duration of the inhalation.

Capsule Emitted Powder Mass.

A measure of the emission properties of the powders was determined by using the information obtained from the Andersen Cascade Impactor tests or emitted geometric diameter by Spraytec. The filled capsule weight was recorded at the beginning of the run and the final capsule weight was recorded after the completion of the run. The difference in weight represented the amount of powder emitted from the capsule (CEPM or capsule emitted powder mass). The CEPM was reported as a mass of powder or as a percent by dividing the amount of powder emitted from the capsule by the total initial particle mass in the capsule. While the standard CEPM was measured at 60 L/min, it was also measured at 15 L/min, 20 L/min, or 30 L/min.

Tap Density.

Tap density was measured using a modified method requiring smaller powder quantities, following USP <616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder. Instruments for measuring tap density, known to those skilled in the art, include but are not limited to the Dual Platform Microprocessor Controlled Tap Density Tester (Vankel, Cary, N.C.) or a SOTAX Tap Density Tester model TD2 (Horsham, Pa.). Tap density is a standard, approximated measure of the envelope mass density. The envelope mass density of an isotropic particle is defined as the mass of the particle divided by the minimum spherical envelope volume within which it can be enclosed.

Bulk Density.

Bulk density was estimated prior to tap density measurement procedure by dividing the weight of the powder by the volume of the powder, as estimated using the volumetric measuring device.

Hausner Ratio.

This is dimensionless number which is calculated by dividing the tap density by the bulk density. It is a number that is correlated to the flowability of a powder.

Liquid Feedstock Preparation for Spray Drying.

Spray drying homogenous particles requires that the ingredients of interest be solubilized in solution or suspended in a uniform and stable suspension. Calcium lactate and sodium chloride are sufficiently water-soluble to prepare suitable spray drying solutions. The solubility for each of these two salts is listed in Table 1.

TABLE 1

Calcium Lactate and Sodium Chloride Solubility in Water
Salt Solubility in Water
(at 20-30° C., 1 bar)

| Salt | Water solubility (g/L) |
|---|---|
| Calcium lactate | 105[1] |
| Sodium chloride | 360[1] |

[1]Perry, Robert H., Don W. Green, and James O. Maloney. *Perry's Chemical Engineers' Handbook*. 7th ed. New York: McGraw-Hill, 1997. Print.

In addition, when preparing spray drying solutions, the water weight of the hydrated starting material should be accounted for. The ratios used for formulations were based on the molecular weight of the anhydrous salts. For certain salts, hydrated forms are more readily available than the anhydrous form. This required an adjustment in the ratios originally calculated, using a multiplier to correlate the molecular weight of the anhydrous salt with the molecular weight of the hydrate. An example of this calculation is included below. The weight percent of calcium ion in calcium lactate and calcium lactate pentahydrate is listed in Table 2.

TABLE 2

Weight Percent of $Ca^{2+}$ in Calcium Lactate

| Salt | Formula | MW | Weight % of $Ca^{2+}$ in molecule |
|---|---|---|---|
| Calcium lactate | $Ca(C_3H_5O_3)_2$ | 218.2 | 18.3 |
| Calcium lactate pentahydrate | $Ca(C_3H_5O_3)_2 \cdot 5H_2O$ | 308.2 | 13.0 |

Spray Drying Using Niro Spray Dryer.

Dry powders were produced by spray drying utilizing a Niro Mobile Minor spray dryer (GEA Process Engineering Inc., Columbia, Md.) with powder collection from a cyclone, a product filter or both. Atomization of the liquid feed was performed using a co-current two-fluid nozzle either from Niro (GEA Process Engineering Inc., Columbia, Md.) or a Spraying Systems (Carol Stream, Ill.) two-fluid nozzle with gas cap 67147 and fluid cap 2850SS, although other two-fluid nozzle setups are also possible. In some embodiments, the two-fluid nozzle can be in an internal mixing setup or an external mixing setup. Additional atomization techniques include rotary atomization or a pressure nozzle. The liquid feed was fed using gear pumps (Cole-Parmer Instrument Company, Vernon Hills, Ill.) directly into the two-fluid nozzle or into a static mixer (Charles Ross & Son Company, Hauppauge, N.Y.) immediately before introduction into the two-fluid nozzle. An additional liquid feed technique includes feeding from a pressurized vessel. Nitrogen or air may be used as the drying gas, provided that moisture in the air is at least partially removed before its use. Pressurized nitrogen or air can be used as the atomization gas feed to the two-fluid nozzle. The process gas inlet temperature can range from 70° C. to 300° C. and outlet temperature from 50° C. to 120° C. with a liquid feedstock rate of 10 mL/min to 100 mL/min. The gas supplying the two-fluid atomizer can vary depending on nozzle selection and for the Niro co-current two-fluid nozzle can range from 5 kg/hr to 50 kg/hr or for the Spraying Systems two-fluid nozzle with gas cap 67147 and fluid cap 2850SS can range from 30 g/min to 150 g/min. The atomizing gas rate can be set to achieve a certain gas to liquid mass ratio, which directly affects the droplet size created. The pressure inside the drying drum can range from +3"WC to −6"WC. Spray dried powders can be collected in a container at the outlet of the cyclone, onto a cartridge or baghouse filter, or from both a cyclone and a cartridge or baghouse filter.

Spray Drying Using Büchi Spray Dryer.

Dry powders were prepared by spray drying on a Büchi B-290 Mini Spray Dryer (BÜCHI Labortechnik AG, Flawil, Switzerland) with powder collection from either a standard or High Performance cyclone. The system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. Inlet temperature of the process gas can range from 100° C. to 220° C. and outlet temperature from 60° C. to 120° C. with a liquid feedstock flowrate of 3 mL/min to 10 mL/min. The two-fluid atomizing gas ranges from 25 mm to 45 mm (300 LPH to 530 LPH) and the aspirator rate from 70% to 100% (28 $m^3$/hr to 38 $m^3$/hr).

Table 3 provides feedstock formulations used in preparation of some dry powders described herein.

TABLE 3

Feedstock Formulations

| Formulation | Feedstock Composition (w/w) |
|---|---|
| I | 20.0% leucine, 75.0% calcium lactate, 5.0% sodium chloride |
| II | 37.5% leucine, 58.6% calcium lactate, 3.9% sodium chloride |
| III | 39.4% leucine, 58.6% calcium lactate, 2.0% sodium chloride |
| IV | 10.0% leucine, 58.6% calcium lactate, 31.4% sodium chloride |
| V | 30.0% leucine, 65.6% calcium lactate, 4.4% sodium chloride |
| VI | 20.0% leucine, 77.4% calcium lactate, 2.6% sodium chloride |
| VII | 20.0% leucine, 70.6% calcium lactate, 9.4% sodium chloride |
| VIII | 33.6% leucine, 58.6% calcium lactate, 7.9% sodium chloride |
| IX | 25.7% leucine, 58.6% calcium lactate, 15.8% sodium chloride |

Cation Contribution

| Formulation | % $Ca^{2+}$ (w/w) | % $Na^+$ (w/w) |
|---|---|---|
| I | 13.8 | 2.0 |
| II | 10.8 | 1.5 |
| III | 10.8 | 0.8 |
| IV | 10.8 | 12.4 |
| V | 12.0 | 1.7 |
| VI | 14.2 | 1.0 |
| VII | 13.0 | 3.7 |
| VIII | 10.8 | 3.1 |
| IX | 10.8 | 6.2 |

The dry powders exemplified herein are referred to by formulation number and have the chemical composition disclosed in Table 3. Dry powders produced using different solution preparations, equipment, or process parameters, but that have the same chemical composition, are referred to using differing capital letters. For example, Formulation I-A and I-B have the same chemical composition bUT were produced using different equipment and/or process parameters.

Description of Placebo Used for In Vivo Experiments

Placebo formulations comprising either 100 weight percent leucine (Placebo-A and Placebo-C) or 98 weight percent leucine with 2 weight percent sodium chloride (Placebo-B) were produced by spray drying. An aqueous phase was prepared for a batch process by dissolving leucine or leucine and sodium chloride in ultrapure water with constant agitation until the materials were completely dissolved in the water at room temperature. The solution was then spray dried using a Niro Mobile Minor spray dryer (GEA Process Engineering Inc., Columbia, Md.). The total liquid feedstock solids concentration was 15 g/L. Atomization of the liquid feed used a co-current two-fluid nozzle from Niro (GEA Process Engineering Inc., Columbia, Md.) for Placebo-A and a Spraying Systems (Carol Stream, Ill.) two-fluid nozzle with gas cap 67147 and fluid cap 2850SS for Placebo-B and Placebo-C. The liquid feed was fed using gear pumps (Cole-Parmer Instrument Company, Vernon Hills, Ill.) into a static mixer (Charles Ross & Son Company, Hauppauge, N.Y.) immediately before introduction into the two-fluid nozzle. Nitrogen was used as the drying gas. Process parameters are shown in Table 4, where the process gas inlet temperature, two-fluid atomization gas, process gas flowrate and liquid feedstock flowrate were controlled and the outlet temperature recorded. The pressure inside the drying chamber was controlled at −2"WC. Spray dried powders were collected from a product collection filter.

TABLE 4

Placebo Spray Drying Process Conditions

| | Formulation | |
|---|---|---|
| Process parameter | Placebo-A | Placebo-B,C |
| Process gas inlet temperature (° C.) | 282 | 264 |
| Process gas outlet temperature (° C.) | 98 | 99 |
| Process gas flowrate (kg/hr) | 85 | 80 |
| Atomization gas flowrate (g/min) | 242 | 80 |
| Liquid feedstock flowrate (mL/min) | 70 | 66 |

Example 1

Manufacturing of Liquid Feed into Dry Powder Comprised of Dry Particles

This example describes the preparation of dry powders using an aqueous feedstock, and the characteristics of the manufactured dry powder comprising dry particles.

The feedstock was prepared as a batch by dissolving leucine in ultrapure water, then sodium chloride, and finally calcium lactate pentahydrate. The solution was kept agitated throughout the process until the materials were completely dissolved in the water at room temperature. Details on a selection of the liquid feedstock preparation are shown in Table 5, where the total solids concentration is reported as the total of the dissolved anhydrous material weights. Formulations I-A, II-A, III-A, IV-A, IV-B, IV-C and VI-B were prepared with separate feedstocks utilizing a Niro spray dryer.

TABLE 5

Summary of liquid feedstock preparations of Formulations I-A and II-A.

| Formulation: | I-A | II-A |
|---|---|---|
| Liquid feedstock mixing | Batch mixed | Batch mixed |
| Total solids concentration | 20 g/L | 15 g/L |
| Total solids | 400 g | 300 g |
| Total volume water | 20.0 L | 20.0 L |
| Amount leucine in 1 L | 4.00 g | 5.625 g |
| Amount sodium chloride in 1 L | 1.00 g | 0.585 g |
| Amount calcium lactate pentahydrate in 1 L | 21.19 g | 12.420 g |

Formulation I-A, II-A, III-A, IV-A, IV-B, IV-C and VI-B dry powders were produced by spray drying on the Niro Mobile Minor spray dryer (GEA Process Engineering Inc., Columbia, Md.) with powder collection from a product filter. Atomization of the liquid feed used a Spraying Systems (Carol Stream, Ill.) two-fluid nozzle with gas cap 67147 and fluid cap 2850SS. The liquid feed was fed using gear pumps (Cole-Panner Instrument Company, Vernon Hills, Ill.) directly into the two-fluid nozzle. Nitrogen was used as the drying gas. No humidification of the nitrogren drying gas was performed. Process parameters are shown in Table 6, where the process gas inlet temperature, two-fluid atomization gas, process gas flowrate and liquid feedstock flowrate were controlled and the outlet temperature recorded. The pressure inside the drying chamber was controlled at −2"WC. Spray dried powders were collected from a product collection filter.

TABLE 6

Formulation Spray Drying Process Conditions

| Process Parameter | Formulation | | | | |
|---|---|---|---|---|---|
| | I-A | II-A | III-A | IV-A,B,C | VI-B |
| Liquid feedstock solids concentration: (g/L) | 20 | 15 | 15 | 15 | 15 |
| Process gas inlet temperature: (° C.) | 192 | 212 | 220 | 265 | 220 |
| Process gas outlet temperature: (° C.) | 89 | 100 | 99 | 99 | 99 |
| Process gas flowrate: (kg/hr) | 85 | 85 | 85 | 80 | 85 |
| Atomization gas flowrate: (g/min) | 47 | 48 | 45 | 80 | 45 |
| Liquid feedstock flowrate: (mL/min) | 38 | 40 | 45 | 66 | 45 |

Formulations I-B, II-B, IV-D, VI-A, VIII and IX dry powders were produced by spray drying on the Büchi B-290 Mini Spray Dryer (BÜCHI Labortechnik AG, Flawil, Switzerland) with powder collection in a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90%. Room air was used as the drying gas. For Formulation I-B, inlet temperature of the process gas was 180° C. and outlet temperature at approximately 88° C. with a liquid feedstock flow rate of approximately 4.9 mL/min. The liquid feedstock solids concentration was 10 g/L in ultrapure water. For Formulations II-B, IV-D, VI-A, VIII and IX, inlet temperature of the process gas was from 96° C. to 105° C. to target an outlet temperature of approximately 97° C. to 100° C. with a liquid feedstock flowrate of approximately 4.9 mL/min. The liquid feedstock solids concentration for all of these runs was 5 g/L.

Physical properties of the particles obtained for formulations I-A and II-A are summarized in Table 7. Values with ± indicates standard deviation of the value reported.

TABLE 7

Chemical, Physical, and Aerosol Properties of Powders and Particles

| | Formulation I-A | Formulation II-A |
|---|---|---|
| Chemical properties | | |
| Calcium content of dry powder: (mg calcium/mg of powder; i.e., %/100 w/w) | 0.13 ± 0.00 | 0.11 ± 0.00 |
| Sodium content of dry powder: (mg sodium/mg of powder; i.e., %/100 w/w) | 0.02 ± 0.00 | 0.02 ± 0.00 |
| Physical properties | | |
| Tap Density: (g/cc) | 0.85 ± 0.01 | 0.71 ± 0.03 |
| Bulk density: (g/cc) | 0.37 ± 0.19 | 0.29 ± 0.03 |
| Hausner Ratio | 2.3 | 2.4 |
| Water content by KF (Karl Fischer) coulometric titration with oven: (with standard deviation): (% water) | 2.4 ± 0.1 | 1.4 ± 0.0 |
| Aerosol properties | | |
| Emitted Dose: (percentage of dose emitting from inhaler/dose in capsule placed in inhaler): (%) | 93.8 | 93.8 |
| FPF (fine particle fraction) on ACI (Andersen Cascade Impactor) 2-stage: (% less than 3.4 μm) | 25.0 ± 0.4 | 26.0 ± 3.1 |
| $FPF_{TD}$ on ACI 2-stage: (% less than 5.6 μm) | 41.7 ± 0.9 | 44.8 ± 2.6 |
| MMAD (mass median aerodynamic diameter) on ACI 8-stage: (μm, with standard deviation) | 5.22 ± 0.21 | 6.29 ± 0.32 |
| GSD (geometric standard deviation) of MMAD on ACI 8-stage: | 2.05 ± 0.01 | 1.93 ± 0.03 |
| Dv50 (volume median geometric diameter) on Spraytec: (μm) | 3.3 ± 1.0 | 2.4 ± 0.0 |
| GSD of Dv50 on Spraytec: | 4.1 ± 0.2 | 2.8 ± 0.0 |
| Dv50 on HELOS/RODOS at 0.2 bar: (μm) | 2.54 | 2.70 |
| Dv50 on HELOS/RODOS at 0.5 bar: (μm) | 2.35 | 2.61 |
| Dv50 on HELOS/RODOS at 1.0 bar: (μm) | 2.35 | 2.38 |
| GSD on HELOS/RODOS at 1.0 bar: (μm) | 2.72 | 2.79 |
| Dv50 on HELOS/RODOS at 2.0 bar: (μm) | 2.32 | 2.31 |
| Dv50 on HELOS/RODOS at 4.0 bar: (μm) | 2.23 | 2.22 |
| Dispersibility on HELOS/RODOS at 1 bar/4 bar: | 1.05 | 1.07 |
| Dispersibility on HELOS/RODOS at 0.5 bar/4 bar: | 1.05 | 1.18 |

As shown in Table 7, Formulation I has a HELOS/RODOS dispersibility ratio at 1/4 bar and 0.5/4 bar dispersion energies of 1.05 each, while Formulation II has HELOS/RODOS dispersibility ratios at 1/4 bar and 0.5/4 bar dispersion energies of 1.07 and 1.18, respectively. Values that are close to 1.0, as these values are, are considered indicative that the powders are highly dispersible.

Example 2

Dispersibility: Emitted Mass and Particle Size of Formulations I, II, III, and IV as a Function of Inhaled Energy This example demonstrates the dispersibility of dry powder formulations comprising calcium lactate powders when delivered from a dry powder inhaler over a range of inhalation flow rate and volumes.

The dispersibility of various powder formulations was investigated by measuring the geometric particle size and the percentage of powder emitted from capsules when applying an inhalation maneuver to a dry powder inhaler with flow rates representative of patient use. The particle size distribution and weight change of the filled capsules were measured for multiple powder formulations as a function of flow rate and inhaled volume and fill weight in a passive dry powder inhaler.

Powder formulations were filled into size 3 HPMC capsules (Capsugel V-Caps) by hand with the fill weight measured gravimetrically using an analytical balance (Mettler Toledo XS205). Fill weights of 50 mg were filled for Formulations I-A, II-A, III-A, and IV-A. A capsule based passive dry powder inhaler (RS-01 Model 7, High Resistance, Plastiape S.p.A.) was used which had specific resistances of 0.036 $kPa^{1/2}LPM^{-1}$. Flow rate and inhaled volume were set using a timer controlled solenoid valve with flow control valve with an inline mass flow meter (TSI model 3063). Capsules were placed in the dry powder inhaler, punctured and the inhaler sealed inside a cylinder, exposing the outlet of the DPI to the laser diffraction particle sizer (Spraytec, Malvern), also referred to herein as the Spraytec laser diffraction system (SLDS), in its open bench configuration. The steady air flow rate through the system was initiated using the solenoid valve and the particle size distribution was measured via the Spraytec at 1 kHz for the duration of the single inhalation maneuver with a minimum of 2 seconds. Particle size distribution parameters calculated utilizing the laser diffraction particle sizer included the volume median diameter using the SLDS and called $Dv50_{SLDS}$ so as to avoid confusion with the HELOS/RODOS determined Dv50 and the geometric standard deviation, called $GSD_{SLDS}$ so as to avoid confusion with the GSD of the HELOS/RODOS Dv50 data, and the fine particle fraction of particles less than 5 micrometers in diameter, using the SLDS, and called $FPF_{SLDS}$ (<5.0 µm) so as to avoid confusion with the FPF as determined on the Andersen Cascade Impactor. At the completion of the inhalation duration, the dry powder inhaler was opened, the capsule removed and re-weighed to calculate the mass of powder that had been emitted from the capsule during the inhalation duration. At each testing condition, 5 replicate capsules were measured and the results of $Dv50_{SLDS}$ and $FPF_{SLDS}$, and capsule emitted powder mass (CEPM) were averaged.

In order to relate the dispersion of powder at different flow rates, volumes, and from inhalers of different resistances, the energy required to perform the inhalation maneuver was calculated and the particle size and dose emission data plotted against the inhalation energy. Inhalation energy was calculated as $E=R^2Q^2V$ where E is the inhalation energy in Joules, R is the inhaler resistance in $kPa^{1/2}/LPM$, Q is the steady flow rate in L/min and V is the inhaled air volume in L.

FIG. 1 shows the mass emitted from a capsule for Formulations I, II, III and IV (which are Formulations I-A, II-A, III-A, and IV-A) at a capsule fill weight of 50 mg using the high resistance RS-01 dry powder inhaler. For each powder, a 2 L inhalation was used at the high flow rate condition of 60 LPM, corresponding to the highest energy condition of 9.2 Joules. For the other three flow rates of 30, 20 and 15 LPM, an inhalation volume of 1 L was used. As can be seen from FIG. 1, the entire mass of powder filled into the capsule empties out of the capsule in a single inhalation for all 4 formulations at the highest energy condition tested. For Formulation IV-A greater than 80% of the fill weight empties for all tested inhalation conditions. For Formulations III-A and I-A, capsule dose emission drops below 80% of the fill weight at 0.29 Joules. For Formulation II-A, capsule dose emission drops below 80% of the fill weight at 0.51 Joules.

The particle size distributions of the emitted powder of Formulations I-A, II-A, III-A, and IV-A are listed in Table 8, characterized by the $Dv50_{SLDS}$ and $GSD_{SLDS}$ as a function of the applied flow rate and inhalation energy. Consistent values of $Dv50_{SLDS}$ at decreasing energy values indicate that the powder is well dispersed since additional energy does not result in additional deagglomeration of the emitted powder. The $Dv50_{SLDS}$ values are consistent for all 4 Formulations with the mean $DV50_{SLDS}$ increasing by less than 2 micrometers from the highest inhalation energy condition (and hence most dispersed state) down to inhalation energies of 0.29 Joules. For Formulation I-A, the mean $Dv50_{SLDS}$ did not increase from baseline by 2 micrometers over the whole tested range with the maximum increase of 1.4 micrometers (from 2.1 to 3.5 micrometers) for a decrease of inhalation energy from 9.2 Joules to 0.29 Joules. In these ranges, the $Dv50_{SLDS}$ is not significantly increased in size, which would be expected if the emitting powder contained a lot of agglomerates and was not well dispersed.

TABLE 8

$Dv50_{SLDS}$, $GSD_{SLDS}$ and $FPF_{SLDS}$ as a function of Inhaled Energy

| | | | | | |
|---|---|---|---|---|---|
| | Inhaled Energy (J), $E = R^2Q^2V$ | 9.2 | 1.1 | 0.5 | 0.3 |
| | Flow Rate (LPM) | 60 | 30 | 20 | 15 |
| Formulation IV-A | $Dv50_{SLDS}$ (µm) | 1 ± 0.1 | 1.4 ± 0.1 | 2.3 ± 0.2 | 3.1 ± 0.3 |
| | $GSD_{SLDS}$ | 6 ± 0.4 | 4.4 ± 0.3 | 3.7 ± 0.6 | 3.4 ± 0.7 |
| | $FPF_{SLDS}$ <5 µm | 85 ± 1.1 | 86 ± 0.7 | 78 ± 1.1 | 68 ± 1.9 |
| Formulation III-A | $Dv50_{SLDS}$ (µm) | 3.3 ± 0.2 | 4 ± 0.2 | 5.2 ± 0.2 | 6.2 ± 0.7 |
| | $GSD_{SLDS}$ | 5.5 ± 0.4 | 4.6 ± 0.5 | 4.4 ± 0.3 | 3.3 ± 0.2 |
| | $FPF_{SLDS}$ <5 µm | 61 ± 1.4 | 57 ± 1.4 | 49 ± 1.2 | 42 ± 4.2 |
| Formulation II-A | $Dv50_{SLDS}$ (µm) | 2 ± 0.2 | 3 ± 0.2 | 3.6 ± 0.1 | 5 ± 0.3 |
| | $GSD_{SLDS}$ | 5.6 ± 0.2 | 4.3 ± 1 | 3.7 ± 0.5 | 3.6 ± 0.2 |
| | $FPF_{SLDS}$ <5 µm | 70 ± 0.8 | 65 ± 2.3 | 62 ± 1.7 | 50 ± 2.3 |
| Formulation I-A | $Dv50_{SLDS}$ (µm) | 2.1 ± 0.4 | 2.1 ± 0.1 | 2.8 ± 0.1 | 3.5 ± 0.1 |
| | $GSD_{SLDS}$ | 5.2 ± 0.3 | 4.3 ± 0.2 | 3.3 ± 0.3 | 3.3 ± 0.3 |
| | $FPF_{SLDS}$ <5 µm | 74 ± 1.8 | 74 ± 0.5 | 71 ± 1.2 | 63 ± 0.8 |

Example 3

Emitted Dose for Formulations I, II, III, and IV

This example demonstrates that the emitted dose of dry powder formulations comprising calcium lactate powders when delivered from a dry powder inhaler is repeatable and emits from the capsule and the dry powder inhaler.

Figure 2:
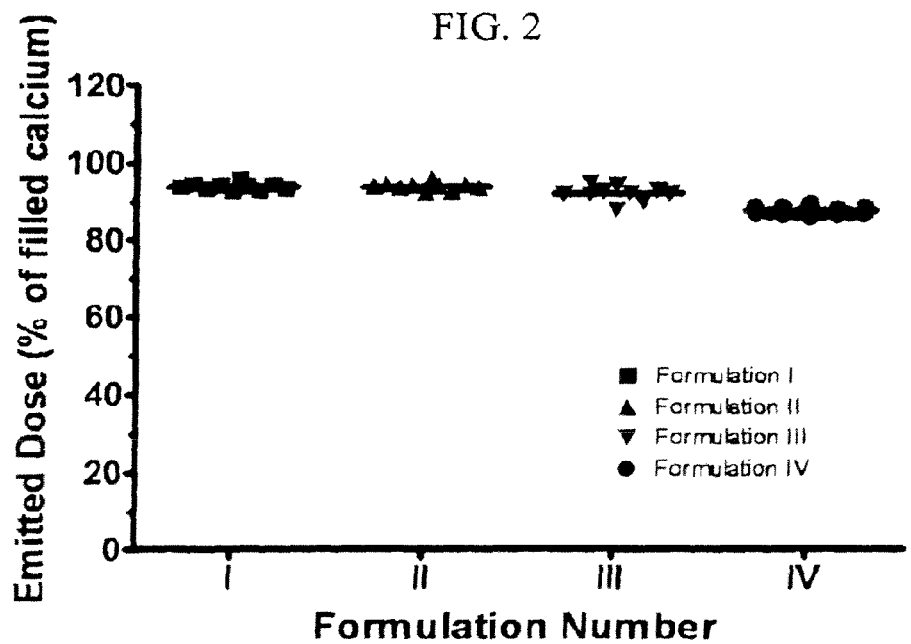
FIG. 2 is a graph showing average emitted dose for Formulations I, II, III and IV. The emitted doses for Formulations I, II, III, and IV were 93.8%, 93.8%, 92.0%, and 87.3%, respectively.

The uniformity of the emitted dose of four powder formulations was measured by determining the mass of calcium which exited the dry powder inhaler (DPI) and was collected in a cylindrical sampling tube. The sampling tube was 120 mm long and 35 mm in diameter based on that specified in the United States Pharmacopeia <601> and contained a 47 mm glass microfiber filter (1820-047, Whatman) at the end to collect the aerosolized powder. At the entrance of the sampling tube, a cylindrical cap, or mouthpiece adapter was connected to make an airtight seal to the DPI. Powder formulations were filled into size 3 HPMC capsules (V-Caps, Capsugel) by hand with the fill weight measured gravimetrically using an analytical balance (Mettler Toledo XS205). Fill weights of 50 mg were filled for Formulations IV-B, III-A, and II-A, and fill weights of 40 mg were filled for Formulation I-A. A reloadable, capsule based passive dry powder inhaler (RS-01 Model 7, High Resistance, Plastiape, Osnago, Italy) was used to disperse the powder into the sampling tube. Two capsules were used for each measurement, with two actuations of 2 L of air at 60 LPM drawn through the dry powder inhaler (DPI) for each capsule. The flow rate and inhaled volume were set using a timer controlled solenoid valve with flow control valve (TPK2000 Copley Scientific). Ten replicate emitted dose measurements were performed for Formulations I-A, II-A, and III-A and thirty replicates for Formulation IV-B. The inner surfaces of the sampling tube, mouthpiece adapter and 47 mm glass microfiber filter were rinsed with 75 mL of water and the rinse solutions assayed by HPLC for calcium ion concentration. The measured emitted calcium mass was divided by the calcium present in the filled capsules (calculated from the measured fill weight of the individual capsules and the known calcium content of the powder formulation) to give the emitted dose as a percentage. The individual replications and the average emitted dose for each of the four formulations tested are shown in FIG. 2 while the average emitted dose and standard deviation for each formulation is shown in Table 9. The nominal calcium content of the filled doses was 11 mg of calcium for all 4 formulations with Formulations II-A, III-A and IV-B having 2 capsules per dose with 50 mg of powder in each capsule and 10.8% calcium (w/w) in the formulations and Formulation I-A having 2 capsules per dose with 40 mg of powder in each capsule and 13.8% calcium (w/w) in the formulation.

TABLE 9

Average emitted doses for Formulations I, II, III, and IV.

|  | Formulation I-A (n = 10) | Formulation II-A (n = 10) | Formulation III-A (n = 10) | Formulation IV-B (n = 30) |
|---|---|---|---|---|
| Avg ED | 93.8% | 93.8% | 92.0% | 87.3% |
| Std | 0.84% | 1.0% | 2.0% | 0.97% |
| $Ca^{2+}$ Content | 13.8% | 10.8% | 10.8% | 10.8% |

All four formulations were found to have repeatable emitted doses as illustrated by the low standard deviations for all four formulations in Table 9 and the lack of individual outliers in FIG. 2. For dry powder formulations intended to be delivered by inhalation for drug delivery, the content uniformity of the emitted dose is an important test required by regulatory bodies such as the Food and Drug Association (FDA) for product approval. Current FDA guidelines require that at least 27 out of 30 replicates of emitted dose be within 80 to 120% of the expected delivered dose and all 30 be within 75% to 125% of the expected delivered dose. The maximum deviation from the average value for any of the replicates of the 4 formulations tested was only 4.6% below the average (i.e., 95.4% of the mean) and so all tested values are well within the required bounds for dry powder inhalation drug products. High emitted dose of powder formulations from a DPI is important for minimizing the amount of powder needed to load into a DPI, both for cost of goods concerns and for maximizing the number of doses that can be contained in a given inhaler. The minimum average emitted dose for the 4 formulations tested was 87.3% of the filled powder, which indicates that the powder is efficiently aerosolized and delivered out of the DPI with minimal residual powder being left in the DPI or capsule.

Example 4

Tap and Bulk Densities and Hausner Ratio for Formulations I, II, III, and IV

Bulk and tapped densities were determined using a SOTAX Tap Density Tester model TD2 (Horsham, Pa.). For any given run, the entire sample was introduced to a tared 0.3 cc section of a disposable serological polystyrene micropipette (Grenier Bio-One, Monroe, N.C.) using a funnel made with weighing paper (VWR International, West Chester, Pa.) and the pipette section was plugged with polyethylene caps (Kimble Chase, Vineland, N.J.) to hold the powder. The powder mass and initial volume ($V_0$) were recorded and the pipette was attached to the anvil and run according to the USP I method. For the first pass, the pippette was tapped using Tap Count 1 (500 taps) and the resulting volume $V_a$ was recorded. For the second pass, Tap Count 2 was used (750 taps) resulting in the new volume $V_{b1}$. If $V_{b1}$>98% of $V_a$, the test was complete, otherwise Tap Count 3 was used (1250 taps) iteratively until $V_{bn}$>98% of $V_{bn-1}$. Bulk density was estimated prior to tap density measurement by dividing the weight of the powder by the volume of the powder, as estimated using the volumetric measuring device. Calculations were made to determine the powder bulk density ($d_B$), tap density ($d_T$), and Hausner Ratio (H), which is the tap density divided by the bulk density.

Results for the density tests for Formulations I (I-A), II (II-A), III (III-A) and IV (IV-C) are shown in Table 10. The tap densities for all formulations are high, especially for formulation I. The bulk densities are such that the Hausner ratio is quite high for all formulations, particularly Formulations I, II and III. All four of the powders tested possess Hausner Ratios that are described in the art as being characteristic of powders with extremely poor flow properties (See, e.g., USP <1174>). USP <1174> notes that dry powders with a Hausner ratio greater than 1.35 are poor flowing powders. Flow properties and dispersibility are both negatively affected by particle agglomeration or aggregation. It is therefore unexpected that powders with Hasuner Ratios of 1.4 to 3.2 would be highly dispersible and possess good aerosolization properties.

TABLE 10

Densities and Hausner Ratio for Formulations I, II, III, and IV

| Formulation | Bulk p (g/cc) | | Tapped p (g/cc) | | Hausner Ratio |
|---|---|---|---|---|---|
|  | Ave | St Dev | Ave | St Dev |  |
| I-A | 0.37 | 0.19 | 0.85 | 0.01 | 2.3 |
| II-A | 0.29 | 0.03 | 0.71 | 0.03 | 2.4 |
| III-A | 0.23 | 0.04 | 0.74 | 0.02 | 3.2 |
| IV-C | 0.52 | 0.10 | 0.75 | 0.07 | 1.4 |

Example 5

Aerodyamic Particle Sizes for Formulations I, II, III, and IV

This example demonstrates that the aerodynamic size distribution of dry powder formulations comprising calcium lactate powders when delivered from a dry powder inhaler is in a range appropriate for deposition in the respiratory tract.

The aerodynamic particle size distributions of four powder formulations were measured by characterizing the powders with an eight stage Andersen cascade impactor (ACI). Powder formulations were filled into size 3 HPMC capsules (Capsugel V-Caps) by hand with the fill weight measured gravimetrically using an analytical balance (Mettler Toledo XS205). Fill weights of 50 mg were filled for Formulations IV-B, III-A, and II-A, and a fill weights of 40 mg were filled for Formulation I-A. A reloadable, capsule based passive dry powder inhaler (RS-01 Model 7, High Resistance, Plastiape, Osnago, Italy) was used to disperse the powder into the cascade impactor. Two capsules were used for each measurement, with two actuations of 2 L of air at 60 LPM drawn through the dry powder inhaler (DPI) for each capsule. The flow rate and inhaled volume were set using a timer controlled solenoid valve with flow control valve (TPK2000 Copley Scientific). Three replicate ACI measurements were performed for Formulations II-A and I-A and five replicates for Formulation III-A and eight replicates for Formulation IV-B. The impactor stages, induction port (IP), entrance cone (EC) and after filter (F) were rinsed with measured volumes of water and the rinse solutions assayed by HPLC for calcium ion concentration. For Formulation III, the entrance cone was not rinsed. The size distribution, MMAD, GSD and fine particle dose <4.4 micrometers (FPD<4.4 μm) of the emitted powder was averaged across the replicates and are tabulated in Table 11. For the Formulations IV-B, III-A and II-A, the dose filled was two capsules of 50 mg powder fill weight which corresponded to 10.8 mg of $Ca^{2+}$ filled into the capsules. For Formulation I-A, the two capsules of 40 mg of powder filled contained the same 10.8 mg of $Ca^{2+}$ due to that formulation's higher $Ca^{2+}$ content.

TABLE 11

Andersen Cascade Impactor Distributions, Fine Particle Dose, and Mass Median Aerodynamic Diameters for Formulations I, II, III, IV

| ACI Stage | | Formulation I-A | Formulation II-A | Formulation III-A | Formulation IV-B |
|---|---|---|---|---|---|
| IP (+EC) | (mg $Ca^{2+}$) | 2.64 ± 0.06 | 1.89 ± 0.17 | 2.35 ± 0.21 | 1.76 ± 0.12 |
| −1 | (mg $Ca^{2+}$) | 1.27 ± 0.14 | 2.06 ± 0.35 | 2.7 ± 0.2 | 0.4 ± 0.04 |
| 0 | (mg $Ca^{2+}$) | 1.31 ± 0.04 | 2.01 ± 0.1 | 1.85 ± 0.07 | 0.62 ± 0.07 |
| 1 | (mg $Ca^{2+}$) | 1.31 ± 0.07 | 1.66 ± 0.08 | 1.36 ± 0.1 | 1.17 ± 0.12 |
| 2 | (mg $Ca^{2+}$) | 0.88 ± 0.08 | 0.86 ± 0.01 | 0.71 ± 0.11 | 1.34 ± 0.1 |
| 3 | (mg $Ca^{2+}$) | 1.03 ± 0.09 | 0.86 ± 0.08 | 0.67 ± 0.07 | 1.98 ± 0.15 |
| 4 | (mg $Ca^{2+}$) | 0.56 ± 0.06 | 0.52 ± 0.03 | 0.37 ± 0.06 | 1.26 ± 0.14 |
| 5 | (mg $Ca^{2+}$) | 0.22 ± 0.01 | 0.27 ± 0.03 | 0.17 ± 0.02 | 0.49 ± 0.05 |
| 6 | (mg $Ca^{2+}$) | 0.09 ± 0.01 | 0.09 ± 0.01 | 0.02 ± 0.03 | 0.14 ± 0.03 |
| F | (mg $Ca^{2+}$) | 0.1 ± 0.03 | 0.14 ± 0.01 | 0.07 ± 0.01 | 0.22 ± 0.03 |
| FPD < 4.4 μm | (mg $Ca^{2+}$) | 2.88 ± 0.1 | 2.72 ± 0.08 | 2.01 ± 0.18 | 5.43 ± 0.29 |
| MMAD | (mm) | 5.22 ± 0.21 | 6.29 ± 0.32 | 7.17 ± 0.23 | 3.12 ± 0.11 |
| GSD | | 2.05 ± 0.01 | 1.93 ± 0.03 | 1.79 ± 0.02 | 2.13 ± 0.01 |

All four formulations were found to have repeatable size distributions as illustrated by the low standard deviations for all the tabulated values. All replicates of all four formulations had greater than 85% of the $Ca^{2+}$ which was filled into the two capsules recovered in the cascade impactor. This both shows that the dosing of the formulations from the DPI is consistent and has low and consistent powder retention in the capsules and DPI as well as shows that the measured size distributions are characteristic of the full dose delivered and not just a sample of the dose. All four formulations have respirable doses as indicated in this test by the fine particle dose <4.4 micrometers that are a significant portion of the filled dose, with fine particle doses ranging from 2.0 mg to 5.4 mg of the filled 10.8 mg of calcium. With a maximum GSD of 2.1 for the four formulations, the polydispersity of the size distributions is relatively small relative to typical dry powder formulations for inhalation.

Example 6

Solid State Testing

A. Spray Drying to Generate Formulations for Solid-State Analysis

Formulations I-C and II-C were produced in a Buchi Mini Spray-Dryer B-290. See Table 12 for two batches which were manufactured. Discussed in this section are the materials that were used, the solution preparation for each batch, the spray drying conditions that were used and also the post process characterization results that were obtained.

TABLE 12

Batches of Formulation I and II manufactured

| Formulation | Spray Drying Conditions | Leucine (% w/w) | Calcium lactate (% w/w) | Sodium chloride (% w/w) | $Ca^{2+}/Na^{+}$ ratio |
|---|---|---|---|---|---|
| I-C | A | 20.0 | 75.0 | 5.0 | 4:1 |
| II-C | A | 37.5 | 58.6 | 3.9 | 4:1 |

Materials.

For the solution preparation the following raw materials were used, see Table 13.

TABLE 13

Materials used in the solution preparation, and their sources

| Material | Supplier |
|---|---|
| Deionized water | Hovione |
| Calcium lactate | Merck |
| L-Leucine | Merck |
| Sodium chloride | Merck |

Solution Preparation.

For each of the formulations, the following excipients, and respective quantities were used (Table 14).

TABLE 14

Solution composition

| Formulation | I | II |
|---|---|---|
| Leucine (g) | 2 | 3.75 |
| Calcium lactate·$5H_2O$ (g) | 10.6 | 8.28 |
| Sodium chloride (g) | 0.5 | 0.39 |
| Added water (g) | 486.9 | 487.58 |

TABLE 14-continued

Solution composition

| Formulation | I | II |
|---|---|---|
| Total solid materials (g) * | 10 | 10 |
| Ca:Na ratio | 4:1 | 4:1 |
| Solids concentration (% w/w) | 2 | 2 |

* Considering the water from calcium lactate.

Spray Drying Conditions and Post Process Characterization.

The spray drying conditions and the post process results for all batches are also described in Table 15. The Dv50, also called Dv(50), was measured with a Malvern Mastersizer (Worcestershire, UK) which similar to the HELOS/RODOS, measures bulk powder without the need for an inhaler to disperse the powder.

TABLE 15

Summary tables of the Spray Drying conditions and the post process results for Formulation I

| Formulation | | I-A | II-A |
|---|---|---|---|
| Feed properties and spray drying parameters | | | |
| Components | | Leucine/Calcium Lactate/Sodium Chloride | |
| Excipients ratio (anhydrous) | %w/w | 20/75/5 | 37.5/58.6/3.9 |
| Solids (anhydrous) | g | 10.01 | 10.009 |
| Water | g | 487 | 488 |
| Solution | g | 500.11 | 500.42 |
| Spray-drying condition | | A | A |
| C_feed [1] | % w/w | 2.001 | 1.998 |
| Inlet temperature (T_in) | ° C. | 136 ± 1 | 144 ± 1 |
| Outlet temperature (T_out) | ° C. | 90 ± 1 | 90 ± 1 |
| Rotameter | mm | 44 | 44 |
| F_atomiz [2] | ml/min | 16 | 16 |
| Ffeed [3] | ml/min | 3.85 | 3.71 |
| Atomization ratio [4] | — | 4 | 4 |
| Drying time | min | 130 | 135 |
| Process throughput and yield | | | |
| F_solids [5] | g/min | 0.08 | 0.07 |
| Yield (1st cyclone) | g | 6.65 | 7.88 |
| Yield (1st cyclone) | % w/w | 66.43 | 78.73 |
| Yield (2nd cyclone) | g | 0.46 | not weighted |
| Yield (2nd cyclone) | % w/w | 75.9 | not weighted |
| Post-Process Results | | | |
| Dv(50) | μm | 1.7 | 1.7 |
| Water by KF | % w/w | 1.7 | 1.5 |
| Dv(50) (2nd cyclone) | μm | 0.7 | not enough product for sample |

(1) C_feed - concentration feed
(2) F_atomiz - atomization flow
(3) F_feed - Feed flow
(4) Atomization ratio = F_atomiz/F_feed
(5) F_solids - solids flow B. Modulated Differential Scanning calorimetry (mDSC):

mDSC experiments were performed utilizing a DSCQ200 System from TA Instruments Inc. Approximately 10 mg of samples were placed inside hermetically sealed pans. mDSC conditions were: equilibration at 0° C. and modulation with a heating rate of 2° C./min, amplitude of 0.32° C. and period of 60 s until 250° C. Glass transition temperatures were determined by the inflection point of the step change in the reversible heat flow versus temperature curve. Using this method, the $T_g$ of Formulation I-C was determined to be approximately 107° C. and Formulation II-C approximately 91° C. See FIG. 3 for plots of the experimental results.

C. X-Ray Powder Diffraction Data

Formulations I-C and II-C were analyzed for amorphous/crystalline content and polymorphic form using high resolution X-ray powder diffraction (XRPD). For XRPD, phase identification was performed to identify any crystalline phases observed in each XRPD pattern. XRPD patterns were collected using a PANalytical X'Pert Pro diffractometer (Almelo, The Netherlands). The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen. Scans were obtained over 3-60° with a step size of 0.017° and a step time of 70 s. As shown in FIG. 4, peaks at approximately 6, 19, 24, 31 and 33° characteristic of leucine (leucine scan not shown) can be seen in the diffractogram for Formulation II-C, indicating the presence of crystalline leucine in this powder (the peak at approximately 44° in each scan is due to the sample holder). No crystallinity peaks characteristic of either calcium lactate pentahydrate or sodium chloride were observed in the diffractograms for either Formulations I-C and II-C, indicating that these components are likely present in an amorphous form in these powders.

D. Scanning Electron Microscopy (SEM)

Figure 5:
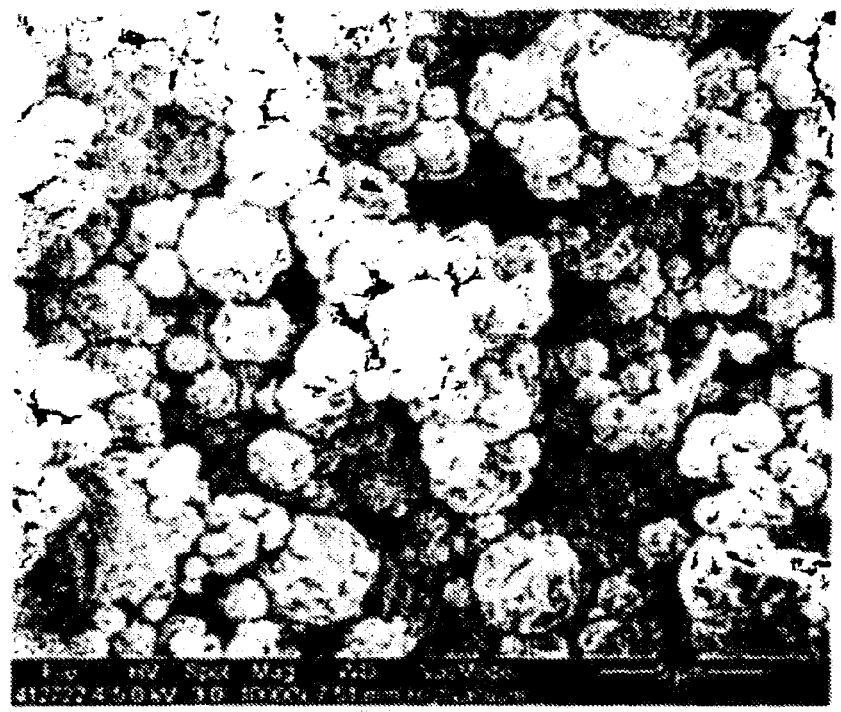
FIG. 5 shows an SEM image (10,000× magnification) of Formulation I.

SEM images were obtained of Formulation I-B. SEM was performed using a FEI Quanta 200 Scanning Electron Microscope equipped with an Everhart Thornley (ET) detector. Images were collected and analyzed using xTm (v. 2.01) and XT Docu (v. 3.2) software. The magnification was verified using a NIST traceable standard. The sample was prepared for analysis by placing a small amount of specimen on a carbon adhesive tab supported on an aluminum mount. The sample was then sputter coated twice with Au/Pd using a Cresington 108 auto Sputter Coater at approximately 20 mA and 0.13 mbar (Ar) for 75 seconds. The sample was observed under high vacuum using a beam voltage of 5 kV. Based on the observation of the SEM image shown in FIG. 5, Formulation I-B is composed of partially collapsed spherical particles with sizes ranging from approximately 0.5 to 5 μm.

Example 7

Efficacy of Formulations with Various Calcium to Sodium Ratios in a Mouse OVA Model of Allergic Asthma In this study, a mouse model of allergic asthma with ovalbumin (OVA) as an allergen was used to study the role of calcium and sodium formulations of the present invention in respiratory disease models in vivo.

Figure 6:
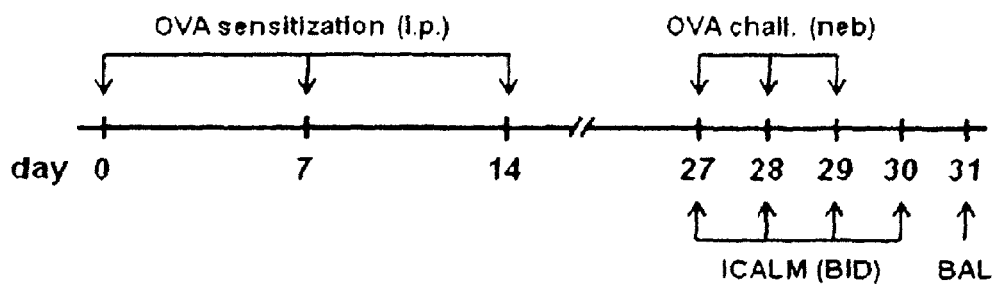
FIG. 6 is a schematic showing the protocol for sensitizing and treating mice in a Mouse OVA model of allergic asthma.

In this model, mice are sensitized to OVA over a period of two weeks and subsequently challenged via aerosol with OVA (FIG. 6). This challenge induces airway inflammation and causes changes in pulmonary function. The principle change in inflammation is an increase in the number of eosinophils in the lungs. Similar changes in lung inflammation and pulmonary function are observed in humans with asthma.

The goal of these studies was to evaluate the effect of calcium and sodium formulations and to assess whether these formulations would further exacerbate the changes in inflammation or could be safely administered. In the course of this work it was discovered that the dry powder formulations of the present invention in fact reduce airway inflammation and reduce the degree of eosinophilia. This result cannot be explained simply by the biophysical mechanism of action, since it was previously observed that soluble factors, such as Der p 1 or OVA, are uninhibited in their movement across mucus-like materials following calcium exposure. Thus, this discovery demonstrates that the salt formulations of the present invention have an unexpected anti-inflammatory property that can serve as a standalone therapy or be combined with other therapies for asthma or asthma-associated symptoms.

TABLE 16

Formulations used in Mouse OVA Allergic Asthma experiments

| Formulation | Ca:Na molar ratio | % excipient (w/w) | % calcium salt (w/w) | % sodium salt (w/w) | % $Ca^{2+}$ (w/w) | % $Na^+$ (w/w) |
|---|---|---|---|---|---|---|
| Placebo-A | N/A | 100 | N/A | N/A | N/A | N/A |
| III-A | 8:1 | 39.4 | 58.6 | 2.0 | 10.8 | 0.8 |
| II-B | 4:1 | 37.5 | 58.6 | 3.9 | 10.8 | 1.5 |
| VIII | 2:1 | 33.6 | 58.6 | 7.8 | 10.8 | 3.1 |
| IX | 1:1 | 25.7 | 58.6 | 15.7 | 10.8 | 6.2 |
| IV-D | 1:2 | 10.0 | 58.6 | 31.4 | 10.8 | 12.4 |

Note:
All formulations used leucine as the excipient, calcium lactate as the calcium salt, and sodium chloride as the sodium salt.

Methods

Mice were sensitized and challenged to OVA as outlined in FIG. 6. Sensitizations were performed by intraperotineal injection of OVA plus Alum. Challenges were performed by whole body exposure to nebulized 1% OVA solution for 20 minutes. Treatments with the dry powder Formulations II-B, III-A, IV-D, VIII, IX, or Placebo-A were 1 h before or 4 h after OVA challenge on days 27-29 and also performed twice on day 30. Treatments were made in a whole body exposure chamber using a capsule based dry powder inhaler system. Dose was varied by changing the number of capsules used for each exposure. On the final day of the study (day 31), mice were euthanized and bronchoalveolar lavages (BAL) were performed. The total number of cells per BAL was determined In addition, the percentage and total number of macrophages, polymorphonuclear cells (neutrophils), lymphocytes, and eosinophils were determined by differential staining.

Figure 7:
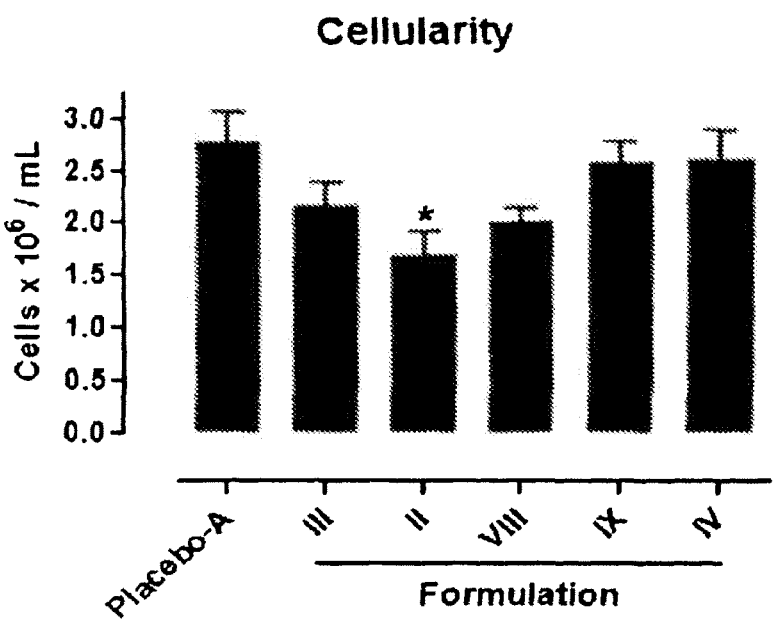
FIG. 7 is a graph showing that treatment with Formulations II, III, IV, VIII, and IX, each of which comprise different calcium to sodium ratios, had varying degrees of efficacy in reducing overall cell count in a Mouse OVA model of allergic asthma. Formulation II had the most profound effect at reducing overall cell count.
Figure 8:
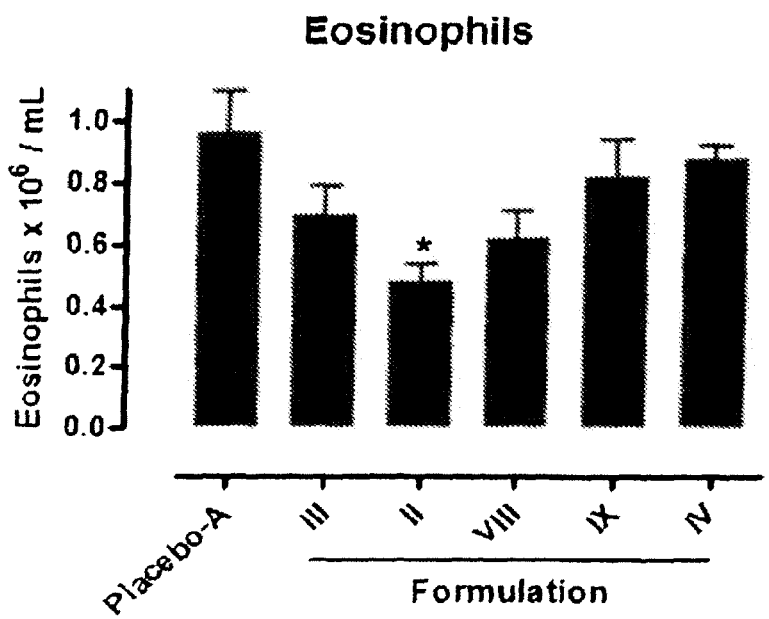
FIG. 8 is a graph showing that treatment with Formulations II, III, IV, VIII, and IX, each of which comprise different calcium to sodium ratios, had varying degrees of efficacy in reducing eosinophil cell count in a Mouse OVA model of allergic asthma. Formulation II had the most profound effect at reducing eosinophil cell count.

As shown in FIGS. 7 and 8, treatment of mice with ~0.48 mg $Ca^{2+}$/kg at calcium to sodium cation ratios of 8:1, 4:1, and 2:1 reduced total BAL cell counts and the same ratios reduced the number of eosinophils in the BAL compared to the control animals. From the formulations listed above, the 4:1 calcium to sodium ratio was significantly more efficacious than the other formulations and reduced cell counts to statistically significant levels ($p<0.05$; one-way ANOVA; Tukey's multiple comparison tests).

Figure 9:
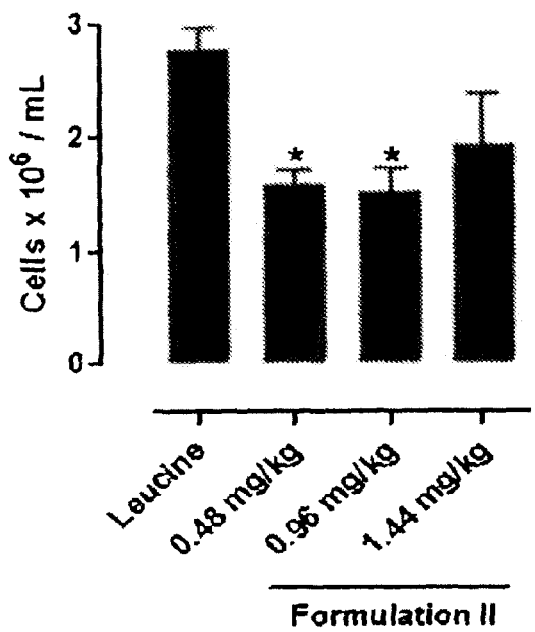
FIG. 9 is a graph showing that treatment with dose range of Formulation II in a Mouse OVA model of allergic asthma had a significant impact on reducing total cell counts.
Figure 10:
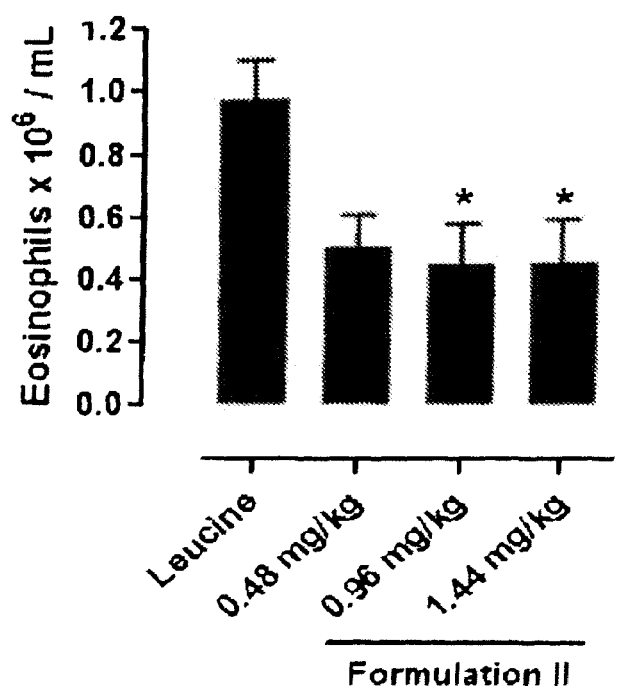
FIG. 10 is a graph showing that treatment with dose range of Formulation II in a Mouse OVA model of allergic asthma had a significant impact on reducing eosinophil cell counts.

In a subsequent study, a dose range of the 4:1 ratio was tested in the same model. Mice treated with increasing doses of 4:1 formulation (~0.48 to ~1.44 mg $Ca^{2+}$/kg) exhibited similar reductions in total inflammatory cell counts and eosinophil counts (FIGS. 9 and 10). Thus, treatment of mice with dry powder formulations comprised of calcium lactate and sodium chloride reduced airway inflammation when delivered at calcium doses of 0.48 mg $Ca^{2+}$/kg or greater.

Accordingly, this discovery provides that due to the anti-inflammatory properties of the salt formulations of the present invention, these formulations can be used in treating or preventing any type of asthma comprising allergic asthma, intermittent asthma, chronic asthma, intrinsic asthma, extrinsic asthma, atopic asthma, childhood asthma, late-onset asthma, cough-variant, and the symptoms associated with each type, or to treat or prevent a disease characterized by eosinophilic infiltrates.

Example 8

Efficacy of Calcium Dry Powder Formulations in Treating Ferret Influenza

This example demonstrates that dry powder formulations comprised of calcium salts and sodium chloride reduce the severity of influenza infection in ferrets. The formulations tested are shown in Table 17. Control ferrets were exposed to a powder comprised of 100% leucine under the same exposure conditions. In preliminary in vitro studies, this control powder had no effect on viral replication. Calcium powders and control (Formulation III-A, Formulation II-A, and Placebo-B) were aerosolized with a Palas Rotating Brush Generator 1000 solid particle disperser (RBG, Palas GmbH, Karlsruhe, Germany). Ferrets (n=8 per group) were exposed to a dose range of ~0.1, ~0.3, or ~0.9 mg $Ca^{2+}$/kg and the severity of infection was evaluated over time. Each formulation was dispersed in a nose-only exposure system 1 hour before infection, 4 hours after infection and then BID for 4 days (d1-4). The study was terminated on day 10. Body temperatures were determined twice a day beginning on day 0 of the study. Ferrets infected with influenza typically show increases in body temperature within 2 days of infection, drop body weight over the course of the study and show clinical signs of infection such as lethargy and sneezing. These changes coincide with an increase in influenza viral titers shed from the nasal cavity and increases in nasal inflammation.

TABLE 17

Formulations tested for efficacy in ferret model of influenza

| Formulation | Ca:Na molar ratio | % excipient salt (w/w) | % calcium salt (w/w) | % sodium (w/w) | % $Ca^{2+}$ (w/w) | % $Na^+$ (w/w) |
|---|---|---|---|---|---|---|
| Placebo-B | N/A | 98.0 | N/A | 2.0 | N/A | 0.8 |
| II-A | 4:1 | 37.5 | 58.6 | 3.9 | 10.8 | 1.5 |
| III-A | 8:1 | 39.4 | 58.6 | 2.0 | 10.8 | 0.8 |

Note:
All formulations used leucine as the excipient, calcium lactate as the calcium salt, and sodium chloride as the sodium salt.

Figure 11:
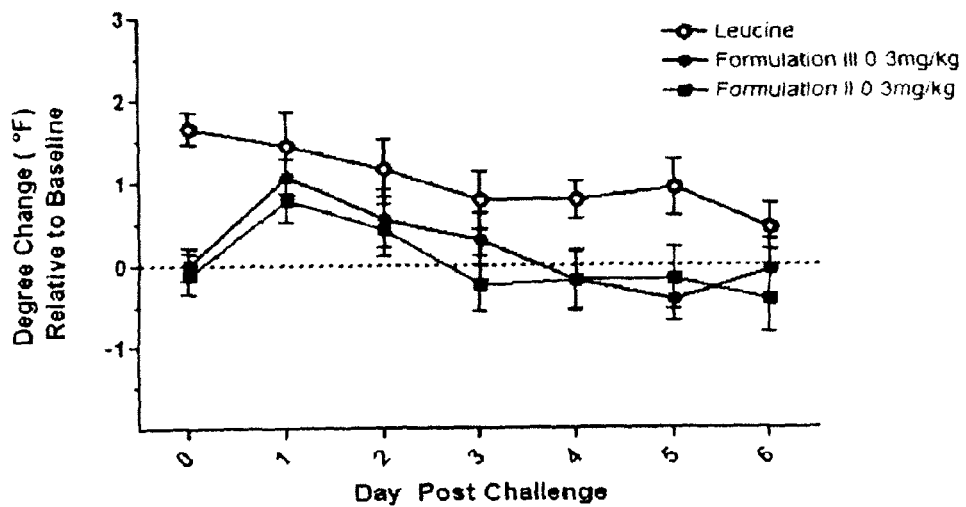
FIG. 11 is a graph showing that treatment with dry powder Formulations II and III had a significant impact on body temperature increases in a Ferret Model of Influenza.
Figure 12:
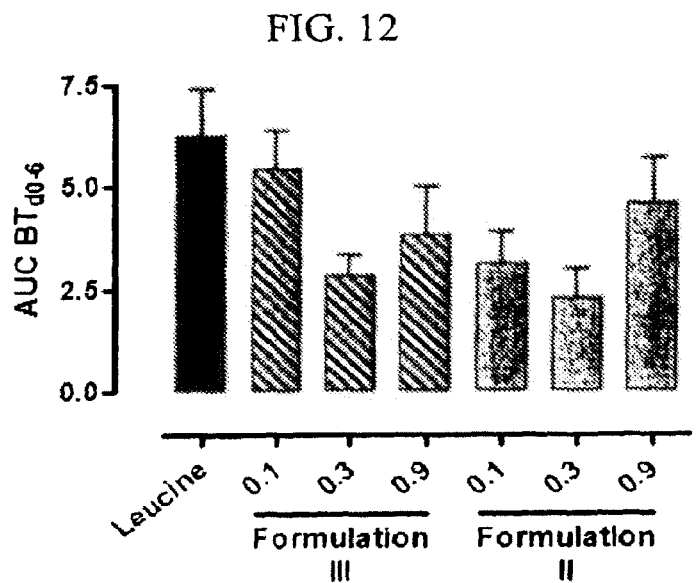
FIG. 12 is a graph showing that the area under the curve (AUC) measurements for all tested doses of Formulations II and III were lower than the placebo control with the maximum reduction seen for the 0.3 mg $Ca^{2+}$/kg doses of both Formulations II-A and III-A, which both were approximately 2.5 to 3-fold lower than the control.

On study day −4, ferrets were implanted with a microchip subcutaneously in the right rear flank and another in the shoulder for redundancy. The transponder chip (IPTT-300 Implantable Programmable Temperature and Identification Transponder; Bio Medic Data Systems, Inc, Seaford, Del. 19973) allows for ferret identification and provides subcutaneous body temperature data throughout the study using a BMDS electronic proximity reader wand (WRS-6007; Biomedic Data Systems Inc, Seaford, Del.). Subcutaneous body temperatures taken on day −3 to −1 were used as baseline temperatures and used to calculate the change from baseline for each animal over the course of the study. Treatment with dry powder Formulations II-A and III-A, both comprising leucine (excipient), Ca-lactate, and NaCl, had a significant impact on body temperature increases (FIG. 11). The mean body temperature changes at the preferred dose of 0.3 mg $Ca^{2+}$/kg body weight for ferrets treated with either formulation remained below measurements for the group treated with control over the course of the study. The area under the curve (AUC) measurements for all tested doses of Formulations II and III were lower than the placebo control with the maximum reduction seen for the 0.3 mg $Ca^{2+}$/kg doses of both Formulations II-A and III-A, which both were approximately 2.5 to 3-fold lower than the control. (See FIG. 12.)

As a second endpoint, the titer of influenza virus in the nasal wash samples of ferrets was determined Nasal wash samples were collected from anesthetized ferrets on d-5, d1, d2, d4, and d10 and viral titers were determined by a microplaque assay. Treatment of ferrets with Formulation II-A and III-A significantly reduced influenza titers on day 1 after infection (Table 18). This reduction was dose dependent and greater than a 1 $log_{10}$ reduction in viral titer at the highest dose of Formulation III tested.

TABLE 18

Plaque forming units (PFU) from nasal wash samples collected on day 1 post infection

|  | Leucine | Formulation II-A | | | Formulation III-A | | |
|---|---|---|---|---|---|---|---|
| mg $Ca^{2+}$/kg | 0 | 0.1 | 0.3 | 0.9 | 0.1 | 0.3 | 0.9 |
| Mean Log10 PFU/mL | 4.2 | 3.9 | 2.9* | 3.6 | 3.6 | 3.6 | 3.2* |

*$p < 0.05$, one-way ANOVA, Tukey's Multiple Comparison test

Example 9

Efficacy of Formulations I, II and IV on Inflammation in the TS Mouse, a Model of COPD Animal models of tobacco smoke (TS) exposure have been used to study the mechanisms of TS induced COPD. Chronic exposure models (up to 6 months) generally result in mild emphysema similar to the human disease. Shorter models have been established to facilitate the testing of novel therapeutics and to evaluate acute airway inflammation following TS exposure. (Fox, J. C., S. Bolton, et al. (2007). *Identification of Tobacco Smoke Models to Evaluate Acute Airway Inflammation Versus Airway Remodeling*. American Thoracic Society, San Francisco, Calif., Medicherla, S., M. F. Fitzgerald, et al. (2008). "p38alpha-selective mitogen-activated protein kinase inhibitor SD-282 reduces inflammation in a sub-chronic model of tobacco smoke-induced airway inflammation." J Pharmacol Exp Ther 324(3): 921-9.)

A. Formulations II and IV Reduce COPD-Associated Inflammation

Figure 13:
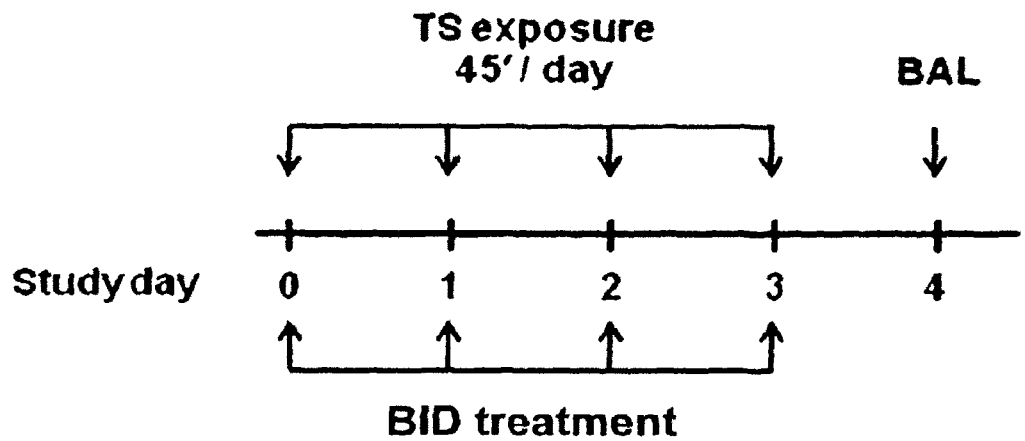
FIG. 13 is a schematic showing the protocol for treating mice in a Tobacco Smoking Mouse model of inflammation.

A study was performed to evaluate the efficacy of a dry powder Formulations II and IV on the pulmonary inflammation induced by TS exposure. A 4-day TS exposure model was used. Mice (C57BL6/J) were exposed to TS for up to 45 minutes per day on four successive days by whole body exposure. The formulations tested are shown in Table 19. On each day of TS exposure, mice were treated with Formulation II-A or Formulation IV-A 1 h before and 6 h after TS exposure. Formulations II-A and IV-A dosing was performed using a whole body exposure system and a capsule based delivery system. A Placebo dry powder of 100% leucine (Placebo-C) was used as a control powder. A schematic depiction of the study design and the estimated doses delivered are shown in FIG. 13. A p38 MAP kinase inhibitor ADS110836 was used as a reference agent (WO2009/098612 Example 11) and was administered by an intranasal route.

Different doses of calcium were delivered by increasing the number of capsules used. Doses were calculated by collecting samples from the pie cage system onto a glass fiber filter at 1 LPM. The aerosol collected onto the filter was recovered and the calcium concentration was determined by HPLC. This data was used to calculate the aerosol concentration ($E_c$) of calcium ion, which was subsequently used to determine the estimated dose level. The estimated dose level ($D_L$) is given by the equation:

$$D_L = E_c \cdot RMV \cdot T / BW$$

where RMV is the respiratory minute volume of the animal (0.21 LPM), T is the exposure time, and BW is the body weight of the animal in kg. The resulting estimated dose is then adjusted for the respirable fraction of the aerosol, which is determined based on the fine particle fraction (FPF; % mass less than 5.6 μm).

Animals were euthanized by intra-peritoneal barbiturate anaesthetic overdose 24 h after the final exposure to either air (sham) or TS on day 5. A bronchoalveolar lavage (BAL) was performed using 0.4 ml of phosphate buffered saline (PBS). Cells recovered from the BAL were enumerated and differential cell counts carried out using cytospin prepared slides.

TABLE 19

Formulations tested for efficacy in mouse model of COPD

| | Formulation composition | | | | | |
|---|---|---|---|---|---|---|
| Formulation | Ca:Na molar ratio | % excipient (w/w) | % calcium salt (w/w) | % sodium salt (w/w) | % $Ca^{2+}$ (w/w) | % $Na^+$ (w/w) |
| Placebo-C | N/A | 100 | N/A | N/A | N/A | N/A |
| II-A | 4:1 | 37.5 | 58.6 | 3.9 | 10.8 | 1.5 |
| IV-A | 1:2 | 10.0 | 58.6 | 31.4 | 10.8 | 12.4 |

Note:
All formulations used leucine as the excipient, calcium lactate as the calcium salt, and sodium chloride as the sodium salt.

Figure 14:
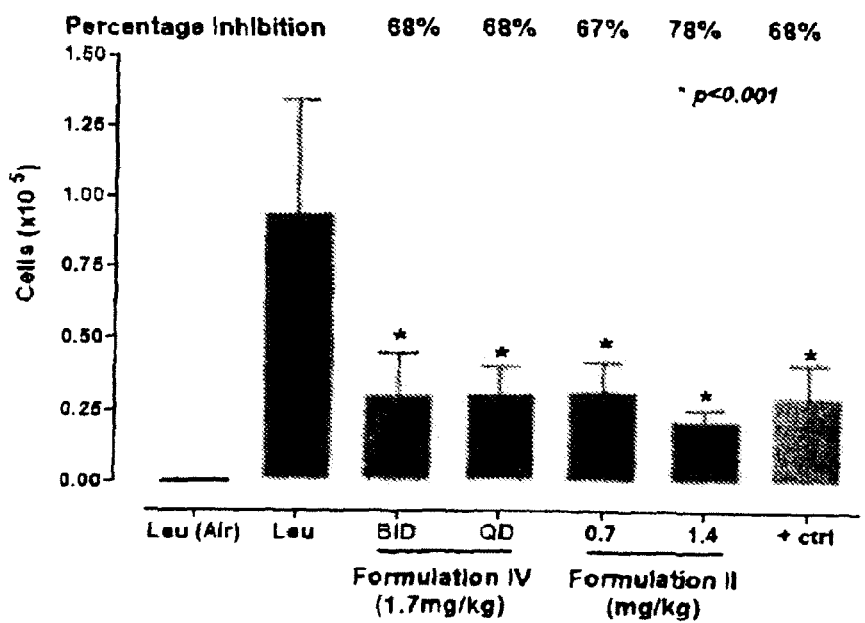
FIG. 14 is a graph showing that a significant reduction in neutrophil inflammation, as represented by cell counts, was seen when TS Mice were treated twice per day (B.I.D.) and once per day (Q.D.) with Formulation IV-A, at two different doses of Formulation II-A, and with a positive control.

Inflammatory cell counts in the BAL fluid of animals exposed to TS for 4 days were determined. TS exposed animals were exposed to Formulation II-A, Formulation IV-A, or a control dry powder of 100% leucine. The leucine treated animals exposed to TS exhibited a 10-fold increase in total cell counts compared to air treated animals that were also administered the control powder. The magnitude of this increase demonstrates the degree of inflammation observed after 4-days of TS exposure. Additional groups of animals were exposed to either Formulation II-A or Formulation IV-A. Formulation IV-A was given both once per day (q.d.) and twice per day (b.i.d.). Formulation II-A was given b.i.d. at two different doses (3 capsules of dry powder and 6 capsules of dry powder, where each capsule contained 150 mg of dry powder). The results are summarized in FIG. 14 and Table 20.

TABLE 20

Reduction of inflammation with treatment using Formulation IV-A, II-A, and a p38 Inhibitor as a positive control

| | Compound | | | | |
|---|---|---|---|---|---|
| | Formulation IV-A | | Formulation II-A | | |
| Treatment | 6 capsules dry powder exposure b.i.d. | 6 capsules dry powder exposure q.d. | 3 capsules dry powder exposure b.i.d. | 6 capsules dry powder exposure b.i.d. | p38 0.1 mg/kg i.n. q.d. |
| Inhibition | % | % | % | % | % |
| Total cells | 45 | 51 | 45 | 58 | 54 |
| Macrophages | 36 | 46 | 40 | 53 | 51 |
| Epithelial cells | 36 | 39 | 28 | 49 | 46 |
| Neutrophils | 68 | 68 | 67 | 78 | 68 |
| Eosinophils | Not significantly increased following TS-exposure | | | | |
| Lymphocytes | 78 | 80 | 64 | 74 | 70 |

All p values were <0.001 except for Formulation II, 3 capsules dry powder expsoure b.i.d. for the Epithelial cells, which had a p value of 0.01.

The data show a dose responsive result for Formulation II-A whereby doubling the dose from 3 capsules b.i.d. to 6 capsule b.i.d. causes an increased inhibition of total inflammatory cells, macrophages, epithelial cells, neutrophils, and lymphocytes. The data also show that q.d. treatment with Formulation IV-A achieves at least an equal reduction in inflammatory cell counts in all categories where a significant response was observed, (to the exclusion of Eosinophils).

B. Formulation I Reduces COPD-Associated Inflammation Both Prophylactically and Therapeutically.

Figure 15A:
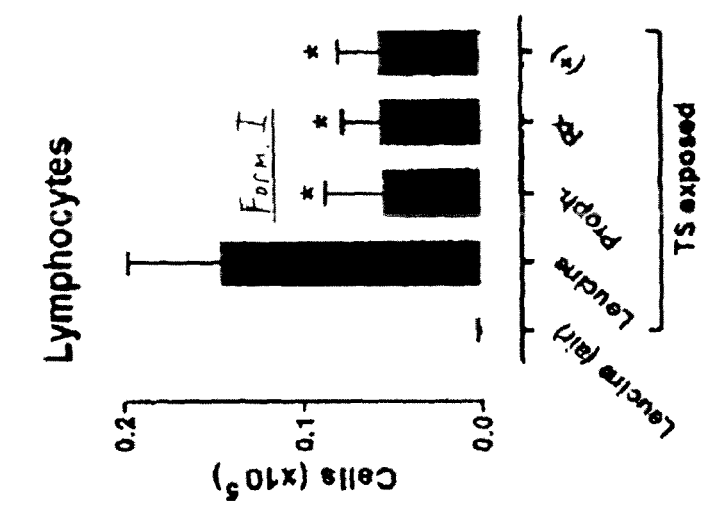
FIG. 15A, FIG. 15B, and FIG. 15C are graphs showing that a significant reduction in macrophage, neutrophil, and lymphocyte inflammation, as represented by cell counts, was seen when TS Mice were treated Q.D. with either prophylactic dosing on therapeutic dosing with Formulation I, and with a positive control.
Figure 15B:
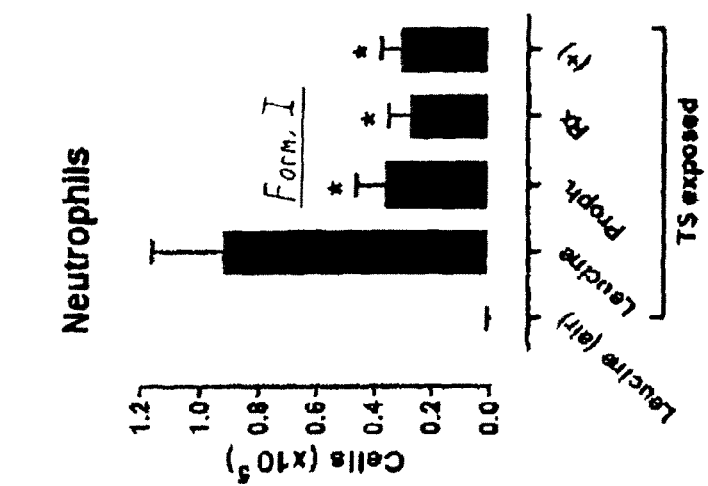
Figure 15C:
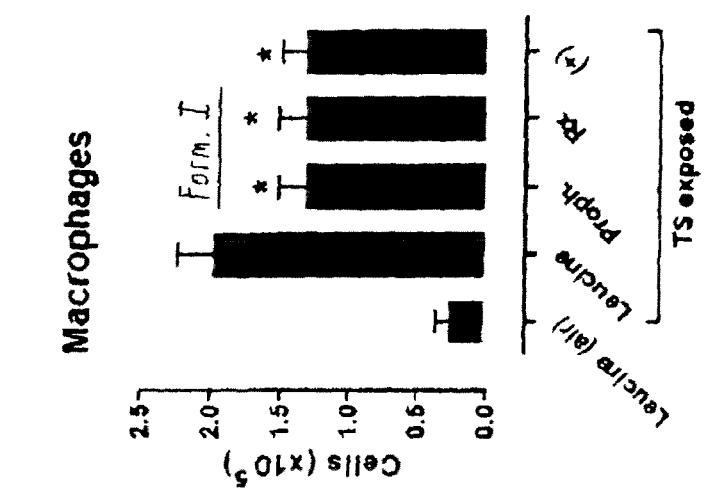

A study was also performed to evaluate the efficacy of Formulation I on inflammation caused by tobacco smoke when administered not only prophylactically, but also therapeutically. An 11 day TS exposure model was used in which mice (C57BL6/J) were exposed to TS by whole body exposure for up to 45 minutes per day. For prophylactic dosing, mice (n=10) were treated once daily with Formulation I (~1.6 mg Ca/kg) by whole body exposure 1 hour before TS exposure beginning on day 0 and continuing to day 11. For therapeutic dosing, mice (n=10) were treated as in the prophylactic regimen except that treatments were not started until day 5 (5 days after TS exposure) and continued until the end of the study (day 11). As a positive control, mice were administered a p38 MAPK inhibitor (+control; 100 µg/kg) intranasally once a day beginning on day 0. Control mice were treated with a dry powder comprised of 100% leucine. TS exposure significantly increased the number of macrophages, neutrophils and lymphocytes compared to air treated animals (FIG. 15A-C). Prophylactic or therapeutic dosing with Formulation I significantly reduced the number of all three cell types to statistically significant levels (FIG. 15A-C). Of note, Formulation I, when administered therapeutically (after the mice had already been exposed to TS for several days) was equally as effective at reducing macrophage, neutrophil and lymphocyte levels as the p38 MAPK inhibitor administered prophylactically from day 0.

Together, the data suggested that aerosol delivery of dry powder formulations comprised of calcium and sodium salts can effectively limit inflammation. The magnitude of the effect was comparable to other drugs that are known to be effective in the TS model and to the p38 MAP kinase inhibitor reference compound used in the studies. A combination therapy that includes a calcium and sodium dry powder formulation with the p38 MAPK inhibitor would likely provide enhanced efficacy and an even greater reduction in inflammation. Similarly, a combination of a calcium and sodium-containing dry powder with other drugs used for the treatment of respiratory diseases characterized by inflammation like COPD, asthma and CF would likely also provide an enhanced benefit. These other drugs include ICS, bronchodilators (LABA/LAMA), p38 MAPK inhibitors, PDE4 inhibitors, antibody therapies, NF-κB inhibitors, and others. (Barnes, P. J. (2008). "Future treatments for chronic obstructive pulmonary disease and its comorbidities." Proc µm Thorac Soc 5(8): 857-64.)

Example 10

Dry Powders Reduce the Expression of Inflammatory Chemokines/Cytokines

Figure 16A:
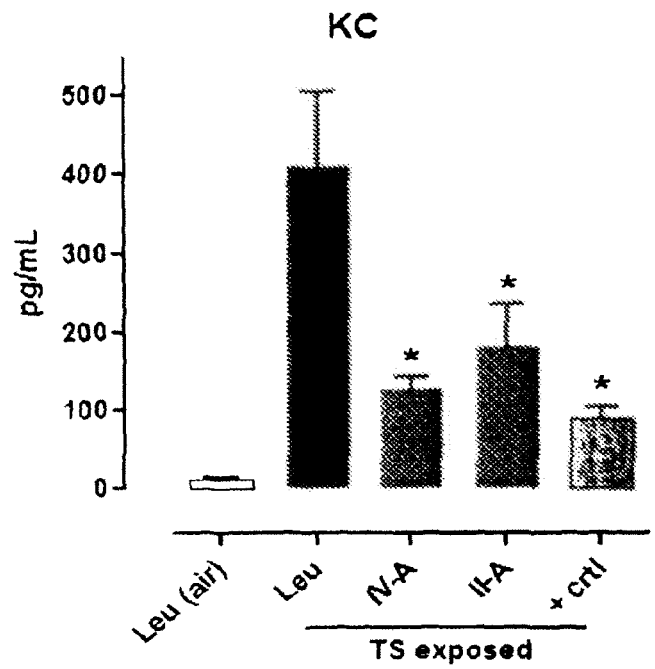
FIG. 16A and FIG. 16B are graphs showing that a significant reduction in KC and MIP2, two key neutrophil chemokines, was seen when TS Mice were treated q.d. with Formulations II-A and IV-A.
Figure 16B:
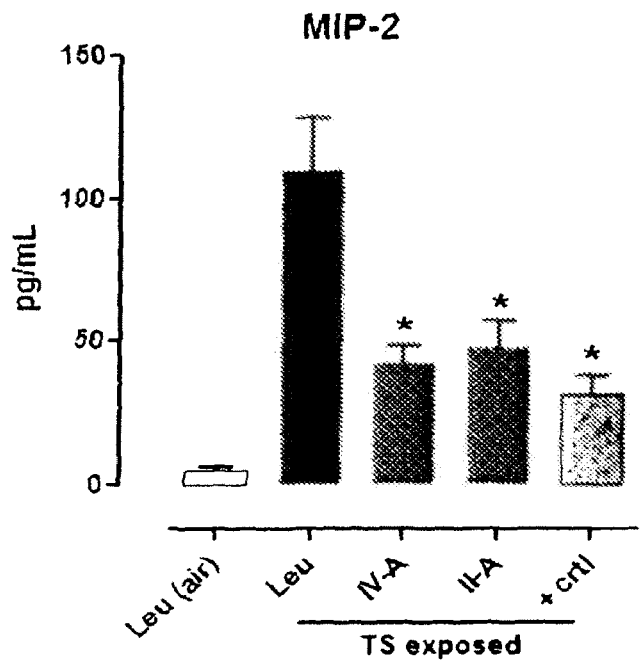

In diseases like allergic asthma and COPD, the influx of inflammatory cells like eosinophils, macrophages, and neutrophils into the airway lumen in response to environmental insult is due to cellular release of cytokines and/or chemokines. These cytokines/chemokines signal to induce the chemotaxis of inflammatory cells to the airway lumen. Using the previously described tobacco smoke (TS) mouse model of COPD, studies were undertaken to determine if the calcium-containing dry powders both reduced inflammation and modulated inflammatory cytokine/chemokine expression. Mice were exposed to TS for 4 consecutive days and treated with Formulation IV-A or Formulation II-A once daily 1 hour before TS exposure. Control animals were exposed to a dry powder formulation of 100% leucine and a second control group was treated with leucine, but not exposed to TS. A p38 MAP kinase inhibitor ADS110836 was used as a reference agent (WO2009/098612 Example 11) and was administered by an intranasal route. At euthanasia, bronchoalveolar lavages (BAL) were performed and BAL samples were assayed for a panel of 13 different cytokines and chemokines that have a role in the inflammation. Protein levels were assessed in a multiplex assay using Luminex technology and concentrations of each protein were determined from standard curves. Data were analyzed by one-way ANOVA and the p values are shown below each group relative to the vehicle group * $p<0.05$. KC and MIP2 represent two key neutrophil chemokines and perform a function analogous to IL-8 in humans. KC and MIP2 expression is upregulated by exposure to TS (see FIGS. 16A-B, Leu Air versus Leu bars). Treatment with either Formulation IV-A or II-A reduced the BAL levels of KC (FIG. 16A) and MIP2 (FIG. 16B) compared to leucine treated animals. The data were similar to the effects of these same formulations on neutrophil chemotaxis to the lung in the same animals and suggested that one mechanism by which the formulations reduce neutrophilic inflammation is through the reduction of chemokine levels that recruit these cells to the lung. These data further suggest that treatment with calcium-containing formulations modulates the biochemical and biological response of the airway epithelium and airway macrophages.

Example 11

Efficacy of Formulation I in a Mouse Model of Bacterial Pneumonia for Both Prophylaxis and Treatment A mouse model of bacterial pneumonia was used to evaluate the efficacy of Ca lactate dry powder formulations in vivo. Bacteria (*Streptococcus pneumoniae*) were prepared by growing cultures on tryptic soy agar (TSA) blood plates overnight at 37° C. plus 5% $CO_2$. Single colonies were re-suspended in sterile PBS to an optical density at 600 nm ($OD_{600}$)

of 0.3 in sterile PBS and subsequently diluted 1:2 in sterile PBS [~4×10⁷ Colony forming units (CFU)/μl]. Mice were infected with 50 μL of bacterial suspension (~2×10⁶ CFU) by intratracheal instillation while under anesthesia.

C57BL6 mice were treated with either Placebo-C (100% Leucine) dry powder or Formulation I-B for in a whole-body exposure system. (See Table 21.) Dry powder aerosol was generated using a capsule based system connected to a top-loading pie chamber cage that individually holds up to 11 animals. All dry powder treatments were delivered at 10 psi and 7 scfh 2.8 L/min) Treatments were performed either 2 h before infection with Serotype 3 *S. pneumoniae* or 4 hours after infections. Twenty-four hours after infection mice were euthanized by pentobarbital injection and lungs were collected and homogenized in sterile PBS. Lung homogenate samples were serially diluted in sterile PBS and plated on TSA blood agar plates. Agar plates were incubated overnight at 37° C. and CFU were enumerated the following day for quantification of bacterial burden in lungs.

TABLE 21

Formulation used in Mouse Pneumonia testing

| | | Formulation composition | | | | |
|---|---|---|---|---|---|---|
| Formulation | Ca:Na molar ratio | % excipient (w/w) | % calcium salt (w/w) | % sodium salt (w/w) | % Ca²⁺ (w/w) | % Na⁺ (w/w) |
| Placebo-C | N/A | 100 | N/A | N/A | N/A | N/A |
| I-B | 4:1 | 20.0 | 75.0 | 5.0 | 13.8 | 2.0 |

Note:
Formulation I used leucine as the excipient, calcium lactate as the calcium salt, and sodium chloride as the sodium salt.

Mice treated with Formulation I-B using either dosing regimen had reduced bacterial counts in lung homogenate samples compared to animals treated with a control dry powder (Table 22). This suggests that such formulations may be beneficial as both a preventative treatment prior to pathogen exposure or alternatively as a therapeutic after the onset of infection.

TABLE 22

Prophylaxis and Treatment with Formulation I in Mouse Pneumonia Model

| | Prophylaxis | | Treatment | |
|---|---|---|---|---|
| | Placebo-C | Formulation I-B | Placebo-C | Formulation I-B |
| Mean Log10 CFU/lung | 7.41 | 6.98** | 7.25 | 6.80* |

N = 5/group. Data were analyzed by Student t- test; *p < 0.05, **p < 0.01.

Example 12

Dry Powders Treat a Pathogen-Induced Acute Exacerbation of Mouse Allergic Asthma Acute exacerbations in asthmatics and COPD patients are a significant cause of lung function decline, morbidity and mortality. Rhinovirus infection is associated with a significant number of acute exacerbations in both patient populations. Calcium-containing dry powder formulations reduced rhinovirus infection in cultured epithelial cells (see WO2010111680, incorporated herein by reference). Preclinical models of rhinovirus in mice have been hampered by the fact that major strains of rhinovirus do not bind to mouse ICAM-1 and therefore do not infect mouse cells. Recently, a mouse model of rhinovirus infection using a minor strain (RV1B) has been described (Bartlett N W et al. Nat Med. 2008 February; 14(2):199-204). Bartlett et al. describe both rhinovirus infection of naïve mice and rhinovirus infection of ovalbumin-challenged mice as a model of acute exacerbations. Using these models, the efficacy of a calcium-sodium dry powder against rhinovirus infection and inflammation was evaluated. The rhinovirus exacerbation model is shown below.

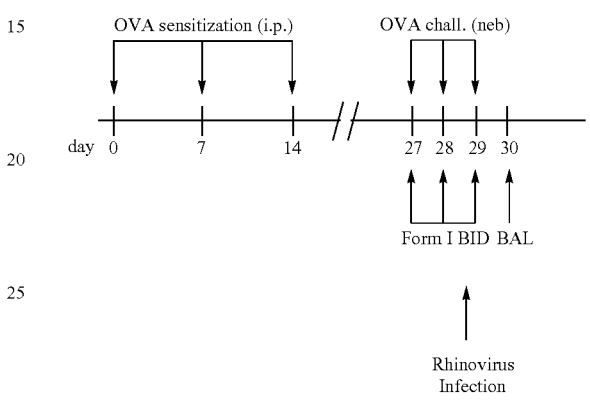

Figure 17A:
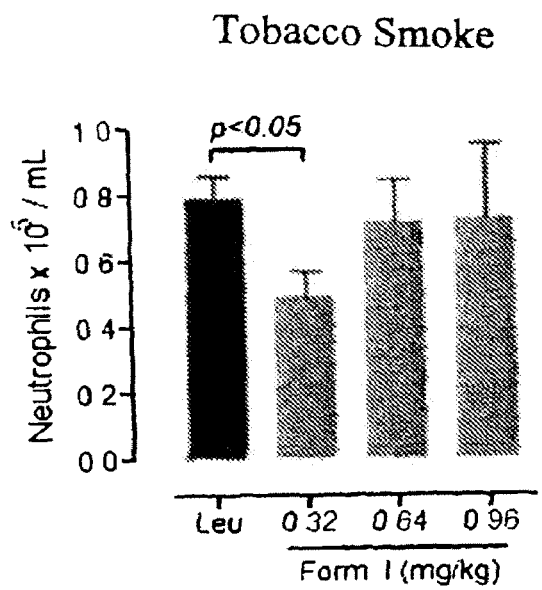
FIG. 17A is a graph showing that a significant reduction in neutrophil inflammation, as represented by cell counts, was seen at the lowest dose tested, when TS Mice were treated b.i.d. with Formulation I.
Figure 17B:
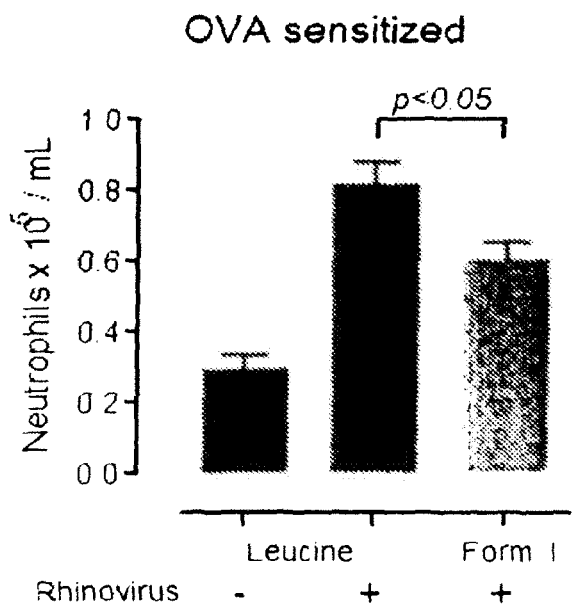
FIG. 17B is a graph showing that a significant reduction in neutrophil inflammation, as represented by cell counts, was seen when OVA sensitized mice were treated with Formation I and then infected with rhinovirus.

BALB/c mice (n=5) were treated with different doses of Formulation I BID for three days before intranasal infection with RV1B. On the day of infection, mice were treated 1 hour before and 4 hours after infection. Twenty-four hours after infection, lung inflammation was assessed by total and differential cell counts in bronchoalveolar lavage samples. At the lowest dose tested, Formulation I significantly reduced the number of total inflammatory cells and neutrophils compared to leucine control treated animals (FIG. 17A). To extend these findings to an exacerbation-like model, mice were sensitized to OVA by standard protocol (see FIG. 6) and dosed BID on each day of OVA challenge. One hour after the final OVA challenge, mice were infected with RV1B. Twenty-four hours after infection, lung inflammation was assessed by total and differential cell counts in bronchoalveolar lavage samples. Rhinovirus infection was associated with increased neutrophilic inflammation compared to uninfected control animals (FIG. 17B). Formulation I reduced that neutrophilic inflammation compared to leucine control treated animals (one-way ANOVA; Tukey's multiple comparison test) (FIG. 17B). Together, these data suggested that an inhaled calcium dry powder could reduce the frequency and severity of acute exacerbations in patients with respiratory disease, in part, by diminishing the inflammation associated with infection.

Example 13

Calcium-Containing Dry Powders do not Cause Airway Hyperreactivity

In respiratory diseases and conditions, the inhalation of foreign particles can often have adverse effects on the small airway of the lung. This can result in airway constriction leading to increased airway resistance, work of breathing and, in extreme cases, a considerable risk to the health of a patient. Thus, it is vital that inhaled therapies, particularly in the setting of inflamed or hyper-reactive airways, do not result in any unintended consequences such as bronchoconstriction. Accordingly, a study was undertaken to determine whether a calcium-sodium formulation (Formulation I) would have an adverse effect on airway bronchoconstriction. Airway resistance was assessed utilizing dual chamber plethysmography. Briefly, mice were constrained in a conical restrainer and placed in a device that consists of two sealed chambers; one encompassing the head and the other encompassing the body with an airtight seal between the two. Pneumotachs measured airflow in each individual chamber and specific airway resistance (sRaw), a direct measure of airway caliber, was calculated as a function of the time delay between flow signals. In order to precisely determine the influence of Fomulation I on sRaw, 5 minutes of baseline sRaw measurements were obtained and the mice were subsequently exposed to a high dose of Formulation I (0.90 mg $Ca^{2+}$/kg). Exposure of the mice to the dry powder was accomplished through the use of a whole body exposure chamber using a capsule-based dry powder inhaler system. Following treatment, 5 minutes of post-treatment sRaw measurements were obtained. Mice were then exposed to escalating doses of methacholine chloride (MCh) in 0.9% sodium chloride for inhalation via nebulization into the head chamber for 10 seconds. The experimental procedure is shown below.

```
           Remove      12.5        50
           Treat   0   6.25 mg/ml  25 mg/ml
    In           mg/ml mg/ml MCh  mg/ml MCh
  Chamber        MCh   MCh        MCh        End
    ↓       ↓    ↓     ↓    ↓     ↓     ↓
    |-------|----|-----|----|-----|-----|
    0       5    10    15   20    25    30    35

Time (min)
```

After each subsequent dose of MCh (0, 6.25, 12.5 25, and 50 mg/ml) the head chamber was cleared and an additional 5 minutes of sRaw was taken. The average sRaw for each 5 minute period was calculated for each animal and normalized to baseline sRaw. This was repeated for two additional groups of mice, whereby the first group was treated with 100% leucine dry power in place of Formulation I, and the second group received a sham treatment consisting of dry air only.

Figure 18:
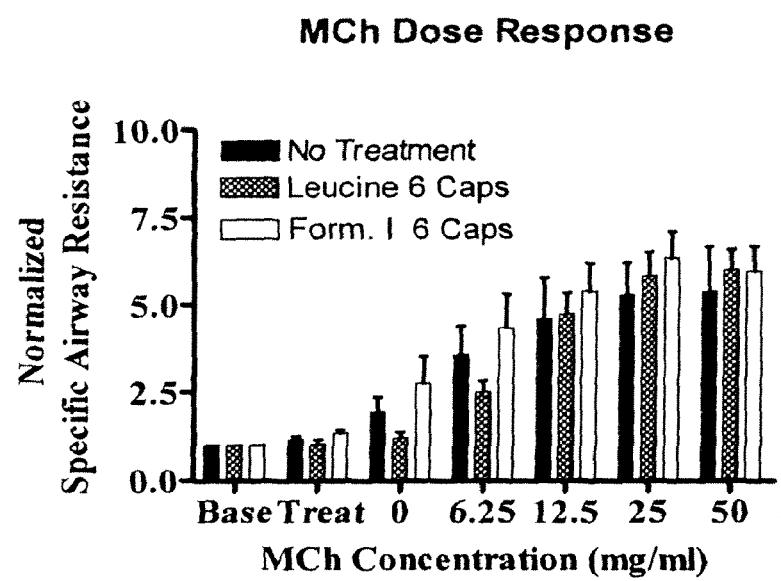
FIG. 18 is a graph showing that no significant increase in airway resistance was observed when mice were treated with Formulation I and then challenged with methacholine chloride (MCh) as compared to when the sham treatment group was challenged with MCh.

Surprisingly, treatment with Formulation I (and leucine) resulted in little change in sRaw and, instead, was statistically indistinguishable from the sham treatment (FIG. 18). In fact, when the animals were exposed to nebulized saline for inhalation (0 mg/ml MCh), the magnitude increase in sRaw was higher than that which was seen during dry powder treatment. In each group, sRaw increased with escalating MCh dose; however, at no point was there a significant difference in sRaw between treatment groups.

Overall, the data demonstrated that calcium dry powder treatment had little influence on sRaw in healthy non-challenged airways and that a calcium dry powder does not adversely influence airway response during periods of bronchoconstriction. Unexpectedly, 0.9% sodium chloride solution for inhalation, a widely utilized diluent for inhaled drug therapies, resulted in a larger magnitude increase in sRaw than did Formulation I. (Results are not shown.) These results clearly demonstrated that calcium-containing dry powders are not likely to inadvertently constrict small airways like some currently accepted therapies (e.g., mannitol inhalation therapy for cystic fibrosis) and could serve as a safe and effective therapy for conditions like COPD, asthma and CF.

Example 14

Calcium-Containing Formulations Enhance Mucociliary Clearance In Vivo

A liquid and a dry powder formulation were evaluated in an established sheep mucociliary clearance (MCC) model. MCC was evaluated in four healthy sheep by measurement of the clearance of pulmonary Tc99m-labeled sulfur colloid aerosols that were delivered by inhalation Immediately following the treatment aerosol exposures, the radiolabeled sulfur colloid aerosol was delivered to each of the sheep via the same aerosol delivery system and MCC determined via the collection of serial images.

A Pari LC jet nebulizer operating with a single sheep exposure system was used to deliver Formulation 14-A (which is 9.4% $CaCl_2$ (w/v), 0.62% NaCl (w/v) in water, at a concentration resulting in a tonicity factor of 8 times isotonic). The nebulizer was connected to a dosimeter system consisting of a solenoid valve and a source of compressed air (20 psi). The output of the nebulizer is connected to a T-piece, with one end attached to a respirator (Harvard Apparatus Inc., Holliston, Mass.). The system was activated for 1 second at the onset of the inspiratory cycle of the respirator, which was set at an inspiratory/expiratory ratio of 1:1 and a rate of 20 breaths/minute. A tidal volume of 300 ml was used to deliver the nebulized formulation. The nebulizer was filled with 4 mL of Formulation 14-A and run to dryness. A dry powder, Formulation I, was delivered with a similar exposure system but with a rotating brush generator (RBG1000, Palas) used to generate the dry powder aerosol instead of the nebulizer. A 15 minute dose of the dry powder Formulation I was delivered with the aerosol continuously generated by the RBG.

The same aerosol exposure system as the liquid treatment was used to deliver aerosolized technetium labeled sulfur colloid (99mTC-SC) immediately after treatment. Animals were conscious, supported in a mobile restraint, intubated with a cuffed endotracheal tube and maintained conscious for the duration of the study.

After 99mTC-SC nebulization, the animals were immediately extubated and positioned in their natural upright position underneath a gamma camera (Dyna Cam, Picker Corp., Nothford, Conn.) so that the field of image was perpendicular to the animals' spinal cord. After acquisition of a baseline image, serial images were obtained at 5 min intervals for the first hour. All images were obtained and stored in the computer for analysis. An area of interest was traced over the image corresponding to the right lung of the animals, and counts were recorded. The left lung was excluded from analysis because its corresponding image was superimposed over the stomach and counts could be affected by swallowed radiolabeled mucus. The counts were corrected for decay and clearance expressed as the percentage reduction of radioactivity present from the baseline image.

The dose delivered for both formulations was measured in-vitro with a breathing simulator system drawing the inspiratory flow through filter samples collected at the distal end of a tracheal tube. For the Formulation I dry powder, 10 filter samples of 1.5 minutes each were assayed for deposited calcium by HPLC and the average rate of calcium deposition was determined From this the dose delivered in 15 minutes to a 50 kg sheep was calculated to be 0.5 mg $Ca^{2+}$/kg. For the liquid Formulation 14-A, 1.5 minute filter samples were again assayed for calcium content by HPLC and the dose delivered when running the 4 mL solution to dryness was calculated for a 50 kg sheep to be 0.5 mg $Ca^{2+}$/kg. These measured doses correspond to the dose delivered from the distal end of the tracheal tube to the sheep during treatment.

Each formulation was tested on 4 different sheep. The sheep mucociliary clearance model is a well established model with vehicle clearance typically measuring approximately 5-10% at 60 minutes after delivery of the radioactive aerosol (see for example Coote et al, 2009, JEPT 329:769-774). It is known in the art that average clearance measurements greater than about 10% at 60 minutes post baseline indicate enhanced clearance in the model. Both the dry powder Formulation I and the liquid Formulation 14-A show enhanced mucociliary clearance in the sheep model, with average clearances ±standard error at 60 minutes post baseline of 16.7%±2.7% and 18.9%±1.2% of baseline radioactivity respectively.

Figure 19:
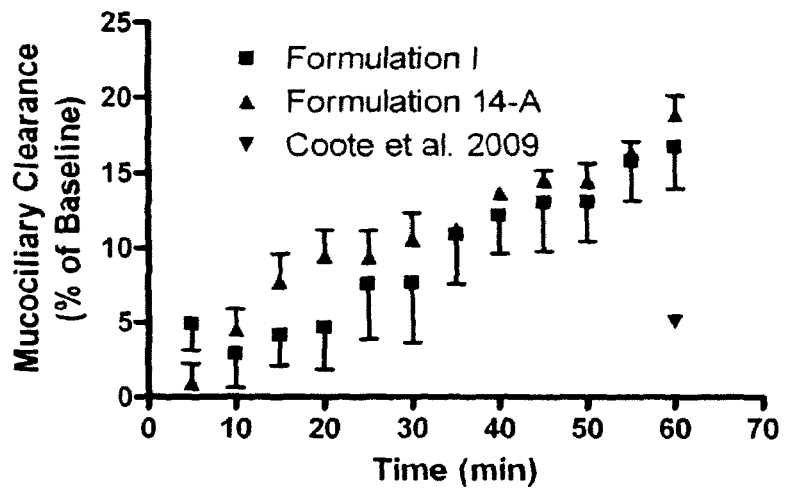
FIG. 19 is a graph showing that a significant increase in mucociliary clearance was seen when sheep were treated with Formulations I and 14-A.

The rate of mucociliary clearance was found to increase over the 60 minute period post dosing. The timecourse of clearance observed for the Formulations I and 14-A are shown in FIG. 19 for n=4 sheep for each data point. Data points indicate average values of clearance from baseline at each 5 minute interval for the four sheep per group (Mean±SEM). Mucociliary clearance was generally increasing throughout the 60 minute interval for both formulations with clearance at 20 minutes of 4.6±2.8% of baseline and 9.4±1.8% of baseline, and clearance at 40 minutes of 12.1±2.5% of baseline and 13.6±0.1% of baseline for Formulations I and 14-A respectively.

The data presented herein show that calcium salt based dry powder and hypertonic liquid formulations can be used to increase mucociliary clearance.

Example 15

Calcium-Containing Dry Powders that Also Contain Additional Therapeutic Agents

A. Powder Preparation.

Feedstock solutions were prepared and used to manufacture dry powders comprised of neat, dry particles containing calcium lactate, sodium chloride, optionally leucine, and other therapeutic agents. Table 23 lists the components of the feedstock formulations used in preparation of the dry powders comprised of dry particles. Weight percentages are given on a dry basis.

TABLE 23

Feedstock compositions of calcium-salt with other therapeutic agents

| Formulation | Feedstock Composition (w/w) |
| --- | --- |
| X | 75.0% calcium lactate, 5.0% sodium chloride, 18.96% leucine, 0.91% fluticasone propionate (FP), 0.13% salmeterol xinafoate (SX) |
| XI | 75.0% calcium lactate, 5.0% sodium chloride, 15.42% leucine, 4.0% fluticasone propionate, 0.58% salmeterol xinafoate |
| XII | 75.0% calcium lactate, 5.0% sodium chloride, 15.31% leucine, 4.0% fluticasone propionate, 0.58% salmeterol xinafoate, 0.113% tiotropium bromide (TioB) |

TABLE 23-continued

Feedstock compositions of calcium-salt with other therapeutic agents

| Formulation | Feedstock Composition (w/w) |
| --- | --- |
| XIII | 75.0% calcium lactate, 5.0% sodium chloride, 18.85% leucine, 0.91% fluticasone propionate, 0.13% salmeterol xinafoate, 0.113% tiotropium bromide |
| XIV | 75.0% calcium lactate, 5.0% sodium chloride, 19.89% leucine, 0.113% tiotropium bromide |
| XV | 75.0% calcium lactate, 5.0% sodium chloride, 16.0% leucine, 4.0% fluticasone propionate |
| XVI | 75.0% calcium lactate, 5.0% sodium chloride, 15.89% leucine, 0.91% fluticasone propionate, 0.113% tiotropium bromide |
| XVII | 75.0% calcium lactate, 5.0% sodium chloride, 20% levofloxacin (Levo) |
| XVIII | 75.0% calcium lactate, 5.0% sodium chloride, 17.5% leucine, 2.5% Immunoglobulin G (IgG) |
| XIX | 75.0% calcium lactate, 5.0% sodium chloride, 19.9% leucine, 0.1% formoterol fumarate (FF) |
| XX | 75.0% calcium lactate, 5.0% sodium chloride, 18.92% leucine, 1.08% albuterol sulfate (AS) |

The feedstock solutions were made according to the parameters in Table 24.

TABLE 24

Formulation Conditions

| Formulation: | X | XI | XII | XIII | XIV | XV | XVI | XVII | XVIII | XIX | XX |
| --- | --- | --- | --- | --- | --- | --- | --- | --- | --- | --- | --- |
| Total solids (g) | 4 | 5 | 4 | 4 | 3 | 4 | 4 | 5 | 5 | 4 | 4 |
| Total volume water (L) | 0.4 | 0.5 | 0.4 | 0.4 | 0.3 | 0.4 | 0.4 | 0.5 | 0.5 | 0.4 | 0.4 |
| Amount leucine in 1 L (g) | 1.9 | 1.541 | 1.53 | 1.89 | 1.99 | 1.6 | 1.59 | 0 | 1.75 | 1.99 | 1.892 |
| Amount FP in 1 L (g) | 0.091 | 0.4 | 0.4 | 0 | 0 | 0.4 | 0.091 | 0 | 0 | 0 | 0 |
| Amount SX in 1 L (g) | 0.013 | 0.058 | 0.058 | 0 | 0 | 0 | 0 | 0 | 0 | 0 | 0 |
| Amount TioB in 1 L (g) | 0 | 0 | 0.0113 | 0.0113 | 0.0113 | 0 | 0.0113 | 0 | 0 | 0 | 0 |
| Amount Levo in 1 L (g) | 0 | 0 | 0 | 0 | 0 | 0 | 0 | 2 | 0 | 0 | 0 |
| Amount IgG in 1 L (g) | 0 | 0 | 0 | 0 | 0 | 0 | 0 | 0 | 0.25 | 0 | 0 |
| Amount FF in 1 L (g) | 0 | 0 | 0 | 0 | 0 | 0 | 0 | 0 | 0 | 0.01 | 0 |
| Amount AS in 1 L (g) | 0 | 0 | 0 | 0 | 0 | 0 | 0 | 0 | 0 | 0 | 0.108 |

For all formulations, the liquid feedstock was batch mixed, the total solids concentration was 10 g/L, the amount of sodium chloride in 1 liter was 0.5 g, and the amount of calcium lactate pentahydrate in 1 liter was 10.6 g.

Formulation X through XX dry powders were produced by spray drying on the Büchi B-290 Mini Spray Dryer (BÜCHI Labortechnik AG, Flawil, Switzerland) with powder collection on a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90%. Air was used as the drying gas and the atomization gas. Table 25 below includes details about the spray drying conditions.

TABLE 25

Spray Drying Process Conditions

| Process Parameters | Formulation | | | | | | | | | | |
|---|---|---|---|---|---|---|---|---|---|---|---|
| | X | XI | XII | XIII | XIV | XV | XVI | XVII | XVIII | XIX | XX |
| Liquid feedstock solids concentration (g/L) | 10 | 10 | 10 | 10 | 10 | 10 | 10 | 10 | 10 | 10 | 10 |
| Process gas inlet temperature (° C.) | 180 | 180 | 180 | 180 | 180 | 180 | 180 | 179-180 | 100 | 180 | 180 |
| Process gas outlet temperature (° C.) | 87-90 | 73-75 | 73-75 | 74-75 | 84-93 | 76-79 | 76-80 | 91-95 | 55-57 | 80 | 74-78 |
| Process gas flowrate (liter/hr, LPH) | 667 | 667 | 667 | 667 | 667 | 667 | 667 | 667 | 667 | 667 | 667 |
| Atomization gas flowrate (meters$^3$/hr) | 35 | 28 | 28 | 28 | 28 | 28 | 28 | 35 | 32 | 28 | 28 |
| Liquid feedstock flowrate (mL/min) | 9.5 | 10 | 10 | 10 | 5.2 | 10 | 9.8 | 5.7 | 2.7 | 5.7 | 5.7 |

B. Powder Characterization.

Powder physical and aerosol properties are summarized in Tables 26, 27, 28, and 29 below. Values with ± indicates standard deviation of the value reported. Table 26 shows that all formulations had an FPFTD<3.4 µm greater than 18%. Formulations X, XI, XIV, XV, XVI, XVII, XVIII, and XIX each had an FPFTD<3.4 µm greater than 25%. Formulations X, XI, XV, and XVI each had FPFTD<3.4 µm greater than 30%. All formulations had an FPFTD<5.6 µm greater than 40%. Formulations X, XI, XIV, XV, XVI, XVII, XVIII, and XIX had an FPFTD<5.6 µm greater than 50%. Formulation XV had an FPFTD<5.6 µm greater than 60%. All formulations had a tapped density greater than 0.45 g/cc. Formulations X, XII, XIII, XIV, XV, XVII, XVIII, XIX, and XX each had tapped densities greater than 0.5 g/cc. Formulations X, XIII, XIV, XVII, XVIII, XIX, and XX each had tapped densities greater than 0.65 g/cc. All formulations had a Hausner Ratio greater than 1.8. Formulations XII, XIV, XV, XVI, XVIII, and XIX each had a Hausner Ratio greater than 2.0. Formulations XV, XVI, and XIX each had a Hausner Ratio equal to or greater than 2.4.

TABLE 26

Aerodynamic and density properties

| | ACI-2 | | Density | | |
|---|---|---|---|---|---|
| Form. | FPF$_{TD}$ < 3.4 µm % | FPF$_{TD}$ < 5.6 µm % | Bulk g/cc | Tapped g/cc | H.R. |
| X | 30.48% ± 0.66% | 56.85% ± 0.17% | 0.34 ± 0.01 | 0.66 ± 0.03 | 1.93 |
| XI | 30.77% ± 0.54% | 56.37% ± 0.24% | N/A ± N/A | N/A ± N/A | N/A |
| XII | 18.64% ± 0.79% | 45.30% ± 0.29% | 0.25 ± 0.09 | 0.51 ± 0.02 | 2.05 |
| XIII | 18.37% ± 0.65% | 41.29% ± 1.14% | 0.36 ± 0.01 | 0.69 ± 0.01 | 1.93 |
| XIV | 28.25% ± 1.01% | 53.19% ± 0.23% | 0.36 ± 0.01 | 0.86 ± 0.03 | 2.38 |
| XV | 36.15% ± 0.55% | 62.62% ± 1.83% | 0.23 ± 0.02 | 0.58 ± 0.04 | 2.46 |
| XVI | 31.34% ± 0.37% | 59.34% ± 0.21% | 0.18 ± 0.01 | 0.48 ± 0.03 | 2.65 |
| XVII | 25.16% ± 1.02% | 52.17% ± 1.14% | 0.34 ± 0.08 | 0.68 ± 0.02 | 1.98 |
| XVIII | 27.18% ± 1.31% | 52.38% ± 1.47% | 0.36 ± 0.01 | 0.77 ± 0.02 | 2.15 |
| XIX | 27.84% ± 9.09% | 52.59% ± 8.34% | 0.37 ± 0.00 | 0.90 ± 0.09 | 2.40 |
| XX | 23.78% ± 0.92% | 47.71% ± 0.60% | 0.40 ± 0.07 | 0.79 ± 0.02 | 1.99 |

Form. = Formulation; H.R. = Hausner Ratio

Table 27 shows that all formulations had geometric diameters (Dv50) of less than 3.5 µm at a dry powder inhaler flowrate of 60 LPM. Formulations X, XIII, XIV, XV, XVI, XVII, XVIII, XIX, and XX had Dv50 of less than 2.5 µm at 60 LPM. All formulations had a Dv50 of less than 6.0 µm at 15 LPM. Formulations X, XIII, XIV, XV, XVII, XVIII, XIX, and XX had Dv50 of less than 4.6 µm at 15 LPM. Formulations XIV, XV, XVII, XVIII, XIX, and XX had a Dv50 of less than 4.0 µm at 15 LPM.

TABLE 27

Dispersibility properties (Spraytec geometric diameters)

| | Dispersibility - Spraytec | | | |
|---|---|---|---|---|
| | @ 60 LPM | | @ 15 LPM | |
| Formulation | Dv50 (µm) | GSD | Dv50 (µm) | GSD |
| X | 2.10 ± 0.08 | 4.15 ± 0.45 | 4.38 ± 0.15 | 3.88 ± 0.24 |
| XI | 2.76 ± 0.11 | 4.18 ± 0.50 | 4.93 ± 0.14 | 2.49 ± 0.50 |
| XII | 3.09 ± 0.32 | 4.68 ± 0.16 | 5.95 ± 0.31 | 3.39 ± 0.15 |
| XIII | 2.23 ± 0.11 | 4.15 ± 0.40 | 4.58 ± 0.12 | 4.19 ± 0.18 |
| XIV | 1.92 ± 0.17 | 6.04 ± 0.42 | 2.51 ± 0.11 | 3.07 ± 0.40 |
| XV | 1.95 ± 0.06 | 5.47 ± 0.24 | 3.78 ± 0.08 | 3.25 ± 0.16 |
| XVI | 2.18 ± 0.08 | 5.24 ± 0.47 | 4.72 ± 0.14 | 3.00 ± 0.19 |
| XVII | 2.01 ± 0.13 | 6.12 ± 0.45 | 2.83 ± 0.24 | 2.61 ± 0.42 |
| XVIII | 1.80 ± 0.11 | 6.07 ± 0.22 | 2.23 ± 0.21 | 3.16 ± 0.55 |
| XIX | 2.11 ± 0.12 | 5.38 ± 0.67 | 2.60 ± 0.05 | 3.04 ± 0.19 |
| XX | 2.13 ± 0.08 | 5.83 ± 0.20 | 2.56 ± 0.04 | 3.22 ± 0.20 |

Table 28 shows that all formulations had a capsule emitted particle mass (CEPM) of greater than 94% at 60 LPM. Formulations X, XI, XII, XIV, XV, XVI, XVII, XVIII, XIX and XX each had a CEPM of greater than 97% at 60 LPM. All formulations had a CEPM of greater than 80% at 15 LPM, except XI. Formulations XII, XIV, XV, XVI, XVIII, XIX, and XX each had a CEPM of greater than 90% at 15 LPM.

TABLE 28

Dispersitibilty properties (CEPM)

| | Dispersibility - CEPM | |
|---|---|---|
| Formulation | @ 60 LPM CEPM | @ 15 LPM CEPM |
| X | 97.48% ± 0.49% | 80.33% ± 4.27% |
| XI | 99.09% ± 0.24% | 59.92% ± 27.96% |
| XII | 97.19% ± 0.25% | 93.15% ± 3.90% |
| XIII | 94.80% ± 1.53% | 82.46% ± 4.61% |
| XIV | 97.83% ± 0.45% | 95.99% ± 0.32% |
| XV | 98.05% ± 0.39% | 92.22% ± 3.48% |
| XVI | 103.32% ± 2.01% | 101.23% ± 2.07% |
| XVII | 99.57% ± 0.00% | 80.41% ± 0.32% |
| XVIII | 99.71% ± 0.16% | 98.08% ± 0.57% |
| XIX | 100.22% ± 0.22% | 98.06% ± 0.47% |
| XX | 99.87% ± 0.22% | 98.10% ± 0.21% |

Table 29 shows that all measured formulations had a Dv50 using the RODOS at its 1.0 bar setting of less than 2.5 µm. Formulations X, XIII, XIV, XV, XVI, XVII, and XVIII each had a Dv50 of less than 2.2 µm. Formulations X, XIII, XV, XVI, and XVII each had a Dv50 of less than 2.0 μm. All measured formulations had a RODOS Ratio for 0.5/4 bar of less than 1.2. All measured formulations had a RODOS Ratio for 1/4 bar of less than 1.1.

TABLE 29

Dispersitibilty properties (Geometric diameter using RODOS)

| | RODOS | | | | | | | |
|---|---|---|---|---|---|---|---|---|
| | 0.5 bar | | 1.0 bar | | 4.0 bar | | | |
| Formulation | Dv50 (μm) | GSD | Dv50 (μm) | GSD | Dv50 (μm) | GSD | 0.5/4 bar | 1/4 bar |
| X | 1.92 | 2.15 | 1.78 | 2.12 | 1.67 | 2.04 | 1.15 | 1.07 |
| XI | N/A | N/A | N/A | N/A | N/A | N/A | N/A | N/A |
| XII | 2.64 | 2.21 | 2.40 | 2.15 | 2.24 | 2.17 | 1.18 | 1.07 |
| XIII | 1.87 | 2.12 | 1.95 | 2.17 | 2.36 | 2.13 | 0.79 | 0.83 |
| XIV | 2.01 | 2.16 | 2.12 | 2.22 | 1.99 | 2.19 | 1.01 | 1.07 |
| XV | 2.12 | 2.16 | 1.84 | 2.15 | 1.92 | 2.16 | 1.10 | 0.96 |
| XVI | 2.13 | 2.15 | 1.83 | 2.14 | 1.87 | 2.18 | 1.14 | 0.98 |
| XVII | 1.93 | 2.23 | 1.83 | 2.24 | 1.69 | 2.17 | 1.14 | 1.08 |
| XVIII | 2.08 | 2.12 | 2.03 | 2.09 | 1.95 | 2.15 | 1.07 | 1.04 |
| XIX | 2.13 | 2.14 | 2.26 | 2.20 | 2.15 | 2.25 | 0.99 | 1.05 |
| XX | 2.24 | 2.14 | 2.22 | 2.19 | 2.23 | 2.22 | 1.00 | 1.00 |

C. Anti-Inflammatory Efficacy of a Co-Formulation of a Calcium Salt with Fluticasone Propionate and Salmeterol Xinafoate (Formulation XI) in an OVA Mouse Model of Allergic Asthma Formulation XI evaluated in a mouse model of allergic asthma using ovalbumin (OVA) as an allergen. The model has been described in Example 7, and the dosing protocol was shown pictorially in FIG. 6.

In this model, mice were sensitized to OVA over a period of two weeks and subsequently challenged, via a liquid aerosol, with OVA (FIG. 6). This challenge induced lung inflammation and increased airway hyperreactivity in response to an airway challenge. The principle change in inflammation was an increase in the number of eosinophils in the lungs. Similar changes in lung inflammation and pulmonary function have been observed in humans with asthma.

Balb/c mice were sensitized and challenged to OVA, as per the sensitization protocol described in Example 7 and shown in FIG. 6. Mice were treated with Placebo-B dry powder (98% leucine, 2% NaCl, w/w on a dry basis), Formulation 15-A (30% leucine, 65.4% NaCl, 4.0% fluticasone propionate and 0.13% salmeterol xinafoate, w/w on a dry basis), and Formulation XI (75.0% calcium lactate, 15.31% leucine, 5.0% NaCl, 4.0% fluticasone propionate and 0.58% salmeterol xinafoate, w/w on a dry basis). Treatments were made in a whole body exposure chamber using a capsule based dry powder inhaler system. On the final day of the study (day 31), mice were euthanized and bronchoalveolar lavages (BAL) were performed. The total number of cells per BAL was determined. In addition, the percentage and total number of eosinophils, neutrophils, macrophages, and lymphocytes were determined by differential staining.

The effect of Formulation XI on inflammation was assessed. Based on the literature, such as, (Ohta, S. et al. (2010) "Effect of tiotropium bromide on airway inflammation and remodeling in a mouse model of asthma", Clinical and Experimental Allergy 40:1266-1275), and Riesenfeld, E. P. (2010). "Inhaled salmeterol and/or fluticasone alters structure/function in a murine model of allergic airways disease", Respiratory Research, 11:22)), fluticasone propionate is known to reduce eosinophilic cells and total cellularity in the mouse OVA model.

What was unknown in the art was the effect of co-formulating FP with a calcium salt formulation. Therefore, Formulation XI was tested. The results in Table 30 show that for a similar dose (mg FP/kg mouse body weight), Formulation XI was equally as efficacious in reducing eosinophilic cells and total cellularity as when the FP was formulated without the calcium salt (Formulation 15-A).

TABLE 30

Formulation XI reduces eosinophilic and total cellular inflammation in a murin model of allergic asthma

| | Placebo-B | | Formulation 15-A | | Formulation XI | |
|---|---|---|---|---|---|---|
| | cells * $10^6$/ml | Std Dev | cells * $10^6$/ml | Std Dev | cells * $10^6$/ml | Std Dev |
| Eosinophils | 0.55 | 0.27 | 0.11 | 0.10 | 0.11 | 0.09 |
| Total cells (Cellularity) | 1.38 | .50 | 0.49 | 0.20 | 0.71 | 0.91 |

D. Effect of Co-Formulations of a Calcium Salt and Salmeterol Xinafoate and Tiotropium Bromide (Formulations XI and XVII, Respectively) on Specific Airway Resistance in a Mouse OVA Model The sensitization of mice with OVA and subsequent challenging of mice with OVA was achieved, as described in Example 7 and shown in FIG. 6. In addition to changes in inflammation, mice sensitized and challenged with OVA exhibit increased airway hyperreactivity, which can be measured as changes in airway resistance following bronchoprovocation. Pulmonary function testing was conducted one hour following treatment on day 30. This involved measuring the specific airway resistance (sRaw) in the mice. Baseline sRaw measurements were taken for 5 minutes. The mice subsequently underwent a methacholine (MCh) challenge for assessing pulmonary function with escalating concentrations of MCh delivered via nebulization in a head chamber using doses of MCh of 0 mg/ml, 50 mg/ml or 100 mg/ml.

The mice were challenged to test their pulmonary function according to the methods described in Example 13. It was known from the literature, for example, (Schutz, N. (2004) "Prevention of bronchoconstriction in sensitized guinea pigs: efficacy of common prophylactic drugs", Respir Physiol Neurobiol 141(2): 167-178), and Ohta, S. et al. (2010), "Effect of tiotropium bromide on airway inflammation and remodeling in a mouse model of asthma", Clinical and Experimental Allergy 40:1266-1275), that both salmeterol xinafoate (SX) and tiotropium bromide (TioB) enhanced pulmonary function, resulting in lower sRaw values, for animals and humans challenged with inhaled methacholine chloride (MCh) in 0.9% sodium chloride.

Figure 20:
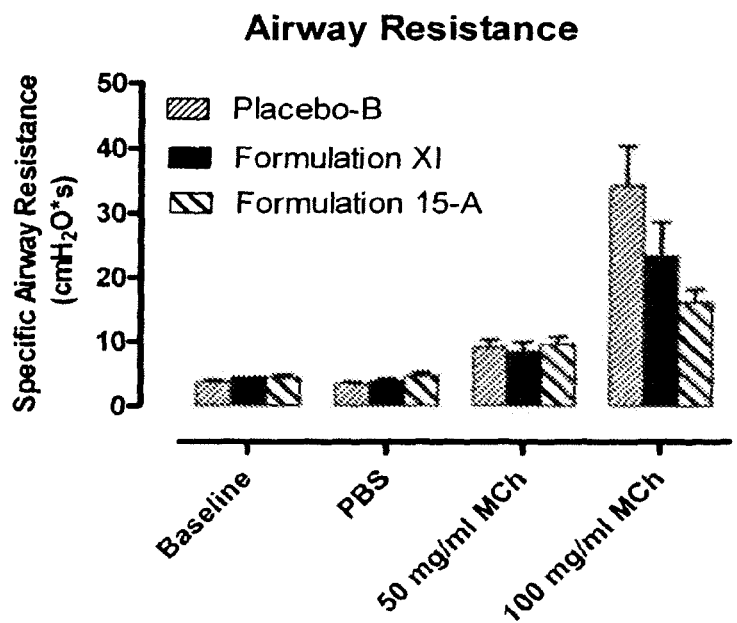
FIG. 20 is a graph showing a decrease in airway resistance was observed when mice were treated with Formulation XI and 15-A and then challenged with methacholine chloride (MCh) as compared to when the sham (Placebo-B) treatment group was challenged with MCh.
Figure 21:
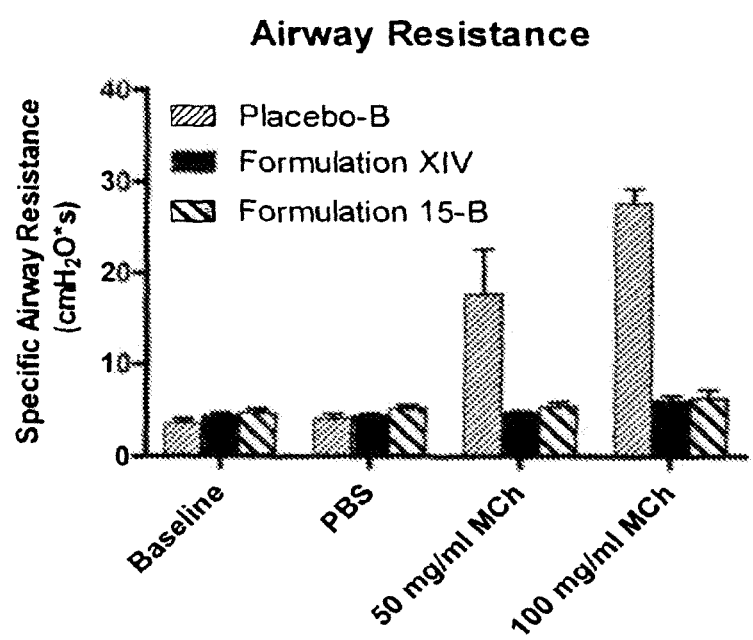
FIG. 21 is a graph showing a decrease in airway resistance was observed when mice were treated with Formulation XIV and 15-B and then challenged with methacholine chloride (MCh) as compared to when the sham (Placebo-B) treatment group was challenged with MCh.

While the effects of SX and TioB on sRaw were known from the literature, the effect of co-formulating SX and TioB formulations with a calcium salt were unknown. Formulations XI (75.0% calcium lactate, 15.31% leucine, 5.0% NaCl, 4.0% fluticasone propionate and 0.58% salmeterol xinafoate, w/w on a dry basis), XIV (75.0% calcium lactate, 19.89% leucine, 5.0% NaCl, and 0.113% tiotropium bromide, w/w on a dry basis), 15-A (30% leucine, 65.4% NaCl 4.0% fluticasone propionate and 0.13% salmeterol xinafoate, w/w on a dry basis), and 15-B (34.47% leucine, 65.42% NaCl and 0.113% tiotropium bromide, w/w on a dry basis) were tested. Non-calcium containing Formulations 15-A and 15-B were tested in order to contrast the efficacies of the calcium-containing Formulations XI and XIV, respectively. Results from pulmonary function testing are shown in FIG. 20 and FIG. 21 for Formulations XI and XIV, respectively. These data show that calcium-containing Formulation XIV matched the positive control, Formulation 15-B, and completely eliminates airway hyperreactivity in response to methacholine challenge in an OVA model of allergic asthma. Treatment with Formulation XI did not match the reduction in sRaw that Formulation 15-A achieved, however, the variability within the group treated with Formulation XI overlapped that of Formulation 15-A and the mean reduction was lower than that observed with Placebo-B.

E. Efficacy of Co-Formulations of a Calcium Salt with Fluticasone Propionate and Salmeterol Xinafoate (Formulation I) in an LPS Mouse Model of Acute Lung Injury A mouse model of acute lung injury was used to study the effects of calcium and sodium formulations combined with other therpautics on pulmonary inflammation. Mice were exposed to aerosolized lipopolysaccharide (LPS) isolated from *Pseudomonas aeruginosa*. This challenge resulted in lung inflammation and caused changes in pulmonary function. The principle change in inflammation was an increase in the number of neutrophils in the lungs. Similar changes in lung inflammation and pulmonary function were observed in humans suffering from acute lung injury.

Mice were exposed to whole body exposure with nebulized LPS, 1.12 mg/ml, for 30 minutes. Treatment with dry powder Formulation XI (75.0% calcium lactate, 15.31% leucine, 5.0% NaCl, 4.0% fluticasone propionate and 0.58% salmeterol xinafoate, w/w/ on a dry bases) was performed 1 hour following LPS exposure using a whole body exposure chamber using a capsule based dry powder inhaler system. Animals were treated with 2, 90 mg capsules corresponding to approximately 0.32 mg $Ca^{2+}$/kg delivered to the lung. To compare the influence of formulations with and without calcium salt, an additional group of animals was exposed to an equivalent amount (i.e. mg of fluticasone/kg of body mass) of an additional powder consisting of Formulation 15-A (30% leucine, 65.4% NaCl, 4.0% fluticasone propionate and 0.13% salmeterol xinafoate). A separate group of animals was treated with 2, 30 mg capsules of Placebo-B control powder (98% leucine, 2% NaCl). Three hours following dry powder treatment all mice were euthanized and underwent whole lung lavage for determination of total and differential cell counts.

As shown in Table 31, treatment of mice with Formulation XI significantly reduced total cell counts and neutrophils in the BAL fluid when compared with animals exposed to Placebo-B and reduced inflammatory cells to a greater extent than the calcium-free Formulation 15-A. Thus, treatment of mice with Formulation XI significantly reduced lung inflammation in an LPS model of acute lung injury.

TABLE 31

Formulation XI reduces inflammation in a rodent model of acute lung injury

| | Placebo-B | | Formulation 15-A | | Formulation XI | |
|---|---|---|---|---|---|---|
| | cells * $10^6$/ml | Std Dev | cells * $10^6$/ml | Std Dev | cells * $10^6$/ml | Std Dev |
| Neutrophils | 1.80 | 0.69 | 1.27 | 0.47 | 1.01 | 0.46 |
| Total cells (Cellularity) | 1.94 | 0.71 | 1.37 | 0.52 | 1.12 | 0.47 |

F. Anti-Bacterial Efficacy of Co-Formulations of a Calcium Salt and Levofloxacin in a *Pseudomonas aeruginosa* Mouse Model A mouse model of bacterial infection was used to evaluate the efficacy of Formulation XVII in vivo. Neutropenia was induced by injection of cyclophosphamide (100 mg/Kg) on days −4 and −1. Bacteria (*Pseudomonas aeruginosa*) were grown overnight in 2 ml of Luria Bertani broth at 37° C. and approximately 5000 CFU were delivered per mouse via intranasal administration in 50 μl of PBS. Four hours following infection the animals were treated with Placebo-B powder (98% leucine, 2% NaCl), Formulation 15-C (27% leucine, 52% NaCl and 20% levofloxacin), and Formulation XVII (75.0% calcium lactate, 5.0% NaCl, 20% levofloxacin) using a whole body exposure chamber using a capsule based dry powder inhaler system. The next day, animals were euthanized and the lungs and the spleen were harvested and homogenized to determine lung bacterial load and systemic bacterial load, respectively. Homogenates were serially diluted on tryptin-soyagar plates and allowed to incubate overnight at 37° C. The following day, colony forming units were counted and CFU/ml for each the lung and the spleen was calculated.

The results are shown in Table 32. It was seen that Formulations XVII and 15-C significantly reduced bacterial burden in the lung by more than 5 $\log_{10}$ CFU and in the spleen by almost 100-fold compared to the Placebo-B treated animals. Thus, treatment of mice with Formulation XVII significantly reduced lung and systemic bacterial burden during *Pseudomonas aeruginosa* infection. It was observed from these data that the presence of calcium in levofloxacin dry powder formulations did not have a deleterious effect on the efficacy of levofloxacin. This is a surprising result given the literature which says that magnesium and calcium based antacids deleteriously affect the bioavailability of levofloxacin taken through the gastrointestinal tract. (Flor, S. et al. (1990), "Effects of Magnesium-Aluminum Hydroxide and Calcium Carbonate Antacids on Bioavailability of Ofloxacin", Antimicrobial Agents and Chemotherapy 34(12): 2436-2438), and Pai, M P. et al. (2006), "Altered steady state pharmacokinteics of levofloxacin in adult cystic fibrosis patients receiving calcium carbonate", J. Cyst. Fibros., August; 5(3): 153-7). (Ofloxacin is a racemic mixture, which consists of 50% levofloxacin, which is known to be biologically active, and 50% of its enantiomer.)

TABLE 32

Formulation XII reduces bacterial burden during *Pseudomonas aeruginosa* infection

| | Placebo | | Formulation 15-C | | Formulation XVII | |
|---|---|---|---|---|---|---|
| | CFU/ml | Std Dev | CFU/ml | Std Dev | CFU/ml | Std Dev |
| Lung | 2.85 × $10^8$ | 2.88 × $10^8$ | 2.08 × $10^4$ | 3.87 × $10^4$ | 9.22 × $10^3$ | 1.78 × $10^3$ |
| Spleen | 1.57 × $10^5$ | 1.78 × $10^5$ | 2.16 × $10^3$ | 6.81 × $10^2$ | 2.53 × $10^3$ | 2.41 × $10^3$ |

G. Co-Formation of a Calcium Salt and a Protein (Formulation XVIII) Provides for Delivery of the Protein Both Locally in the Lungs and Systemically In this study Formulation XVIII (75.0% calcium lactate, 17.5% leucine, 5.0% sodium chloride, 2.5% bovine immunoglobulin G (IgG), w/w on a dry basis) was used to determine if calcium containing dry powder formulations can be used to deliver proteins to the lung and if this dry powder can be used to deliver proteins systemically.

In this study, mice were treated with Formulation XVIII using a whole body exposure chamber using a capsule based dry powder inhaler system. Animals were then treated with 2, 4 or 6 capsules of Formulation XVIII and with another group of animals were treated with 6 capsules of Placebo-B control powder (98% leucine, 2% NaCl). The placebo controls were run to ensure that there was no cross reactivity with the bovine IgG assay and native mouse proteins in either the serum or the broncho-alveolar lavage (BAL). Immediately following DP treatment the animals were euthanized, underwent BAL and serum collected. Lavage fluid and serum were then assayed for bovine IgG using a commercially available ELISA kit.

The results are shown in Table 33. Placebo-B (n=3 animals, data not reported in table) was below the detectable range of the assay, which was indicative that there was no cross reactivity between the bovine IgG and the native mouse protein in either the serum or the BAL. It can be seen that IgG delivered to the lung increases stepwise with increasing number of capsules delivered to the animals. Furthermore, while treatment with 2 or 4 capsules of Formulation XVIII resulted in slight increases in serum IgG content that were in the range of the detection limit of the ELISA kit, treatment with 6 capsules IgG resulted in an increase to approximately 100 ng/ml IgG. Assuming an approximate serum volume of 2 ml, this would suggest that, on average, 200 ng of IgG was delivered systemically with 6 capsules of Formulation XVII treatment. This demonstrated that calcium-containing dry powders can be utilized to deliver proteins systemically.

TABLE 33

Calcium containing, inhaled dry powders can be utilized to deliver proteins to the lungs and systemically

|  | Lung IgG | | Serum IgG | |
| --- | --- | --- | --- | --- |
|  | IgG (ng) | Std Dev | IgG (ng/ml) | Std Dev |
| Form. XVIII (2 capsules) | 100.61 | 39.45 | 3.68 | 6.05 |
| Form. XVIII (4 capsules) | 148.32 | 28.90 | 6.63 | 10.58 |
| Form. XVIII (6 capsules) | 274.73 | 72.52 | 107.41 | 49.41 | n = 6 animals each for the 2, 4, and 6 capsule groups

The content of each of the patents, patent applications, patent publications and published articles cited in this specification are herein incorporated by reference in their entirety.

The invention claimed is:

1. A respirable dry powder, comprising:
respirable dry particles that comprise calcium lactate, sodium chloride, leucine, and one or more additional therapeutic agents;
wherein the ratio of calcium cation to sodium cation is about 4:1 (mole:mole); and,
wherein the calcium lactate is about 58.6% (w/w) to about 75% (w/w), and the sodium chloride is about 3.9% (w/w) to about 5% (w/w), and the leucine is about 20% (w/w) to about 37.5% (w/w), where all weights are on a dry basis.

2. The respirable dry powder of claim 1, wherein the one or more additional therapeutic agents are selected from group consisting of corticosteroids and bronchodilators, and wherein said bronchodilators are one or more bronchodilators selected from the group consisting of long-acting beta$_2$ agonists and long-acting muscarinic anagonists.

3. The respirable dry powder of claim 2, wherein said long-acting beta$_2$ agonists are selected from the group consisting of salmeterol, formoterol, arformoterol, clenbuterol, tulobuterol, vilanterol, indacaterol, carmoterol, isoproterenol, procaterol, bambuterol, and milveterol.

4. The respirable dry powder of claim 2, wherein the long-acting muscarinic anagonists are selected from the group consisting of tiotroprium, trospium chloride, glycopyrrolate, aclidinium, and ipratropium.

5. The respirable dry powder of claim 2, wherein the corticosteroids are selected from the group consisting of budesonide, fluticasone, flunisolide, triamcinolone, beclomethasone, mometasone, ciclesonide, and dexamethasone.

6. The respirable dry powder of claim 1, wherein the one or more additional therapeutic agents is selected from the group consisting of bronchodilators, corticosteroids, and anti-inflammatory agents.

7. The respirable dry powder of claim 1, wherein the one or more additional therapeutic agents is selected from the group consisting of mucoactive or mucolytic agents, surfactants, antibiotics, antivirals, antihistamines, cough suppressants, vaccines, adjuvants, and expectorants.

8. The respirable dry powder of claim 1, wherein the one or more additional therapeutic agents is one or more macromolecules selected from the group consisting of proteins, large peptides, polysaccharides, oligosaccharides, DNA nucleic acid molecules and their analogs, and RNA nucleic acid molecules and their analogs.

9. The respirable dry powder of claim 8, wherein the proteins are one or more antibodies.

10. The respirable dry powder of claim 9, wherein the one or more antibodies are one or more monoclonal antibodies.

11. The respirable dry powder of claim 8, wherein the macromolecule has a molecular weight of at least 800 Da.

12. The respirable dry powder of claim 1, wherein said respirable dry particles have a volumetric median geometric diameter between 0.5 microns and 10 microns and a mass median aerodynamic diameter between 0.5 microns and 10 microns.

13. The respirable dry powder of claim 1, wherein said respirable dry particles have a volumetric median geometric diameter between 1 micron and 5 microns and a mass median aerodynamic diameter between 1 micron and 5 microns.

14. The respirable dry powder of claim 13, wherein said respirable dry powder is suitable for administration to a respiratory tract using a dry powder inhaler.

15. The respirable dry powder of claim 1, wherein said respirable dry particles have a volumetric median geometric diameter of 5 microns or less and a mass median aerodynamic diameter of 5 microns or less.

16. The respirable dry powder of claim 12, wherein said respirable dry powder is suitable for administration to a respiratory tract using a metered dose inhaler.

17. A method for treating a respiratory disease comprising administering to a respiratory tract of a patient in need thereof an effective amount of the respirable dry powder of claim 1.

18. A method for treating or preventing an acute exacerbation of a respiratory disease comprising administering to a respiratory tract of a patient in need thereof an effective amount of the respirable dry powder of claim 1.

19. A method for treating or preventing an infectious disease in a respiratory tract comprising administering to a respiratory tract of a patient in need thereof an effective amount of the respirable dry powder of claim 1.

* * * * *